(12) United States Patent
Ricciardi et al.

(10) Patent No.: US 8,062,590 B1
(45) Date of Patent: Nov. 22, 2011

(54) METHODS AND APPARATUSES FOR APPLYING AGENT TO OBJECTS

(76) Inventors: Jonathan J. Ricciardi, Kennewick, WA (US); Carl L. Ricciardi, Tomahawk, WI (US); Howard J. Swidler, Bethlehem, PA (US)

( * ) Notice: Subject to any disclaimer, the term of this patent is extended or adjusted under 35 U.S.C. 154(b) by 0 days.

(21) Appl. No.: 13/052,199

(22) Filed: Mar. 21, 2011

(51) Int. Cl.
*A61L 2/20* (2006.01)
*B08B 3/00* (2006.01)

(52) U.S. Cl. .......................... 422/33; 134/131
(58) Field of Classification Search ............. 134/131; 422/33
See application file for complete search history.

(56) References Cited

U.S. PATENT DOCUMENTS

| | | | |
|---|---|---|---|
| 4,366,125 A | 12/1982 | Kodera et al. | |
| 4,512,951 A | 4/1985 | Koubek | |
| 4,952,370 A | 8/1990 | Cummings et al. | |
| 5,425,815 A | 6/1995 | Parker et al. | |
| 5,878,355 A | 3/1999 | Berg et al. | |
| 6,102,992 A | 8/2000 | Berg et al. | |
| 6,379,616 B1 | 4/2002 | Sheiman | |
| 7,582,257 B2* | 9/2009 | Bedard et al. | 422/27 |
| 2005/0042130 A1 | 2/2005 | Lin et al. | |
| 2005/0201889 A1* | 9/2005 | Watanabe et al. | 422/3 |
| 2008/0063574 A1* | 3/2008 | Centanni | 422/108 |
| 2010/0316527 A1* | 12/2010 | McLaren et al. | 422/22 |

FOREIGN PATENT DOCUMENTS

GB 1128245 9/1968

OTHER PUBLICATIONS

William C. Hinds, Aerosol Technology Properties, Behavior and Measurement of Airborne Particles, John Wiley & Sons, Inc. 1999, pp. 428-434.

* cited by examiner

*Primary Examiner* — Walter D Griffin
*Assistant Examiner* — Christopher Vandeusen
(74) *Attorney, Agent, or Firm* — Donald J. Ersler

(57) ABSTRACT

Methods and apparatus for the sanitization, detoxification, disinfection, high level disinfection, or sterilization of both the interior and exterior surfaces of at least one object, including interior lumens, channels and cavities within the object. A coupler and interface may be secured to an object to disinfect the inner channels or cavities therein. An object support device may be used to support the object. The pair of support devices may include outlets for deploying aerosols for the application of applied agent. The applied agent may be in the form of any gas, vapor, plasma, aerosol, or other form. The temperature of the object may be lowered to condensate applied agent thereupon. The object may also be washed. Complete sanitization, disinfection, or sterilization of objects in a simple chamber, or in more complex configurations that include, glove box units, processors with built in interfaces for specialty applications, and other application specific designs.

35 Claims, 25 Drawing Sheets

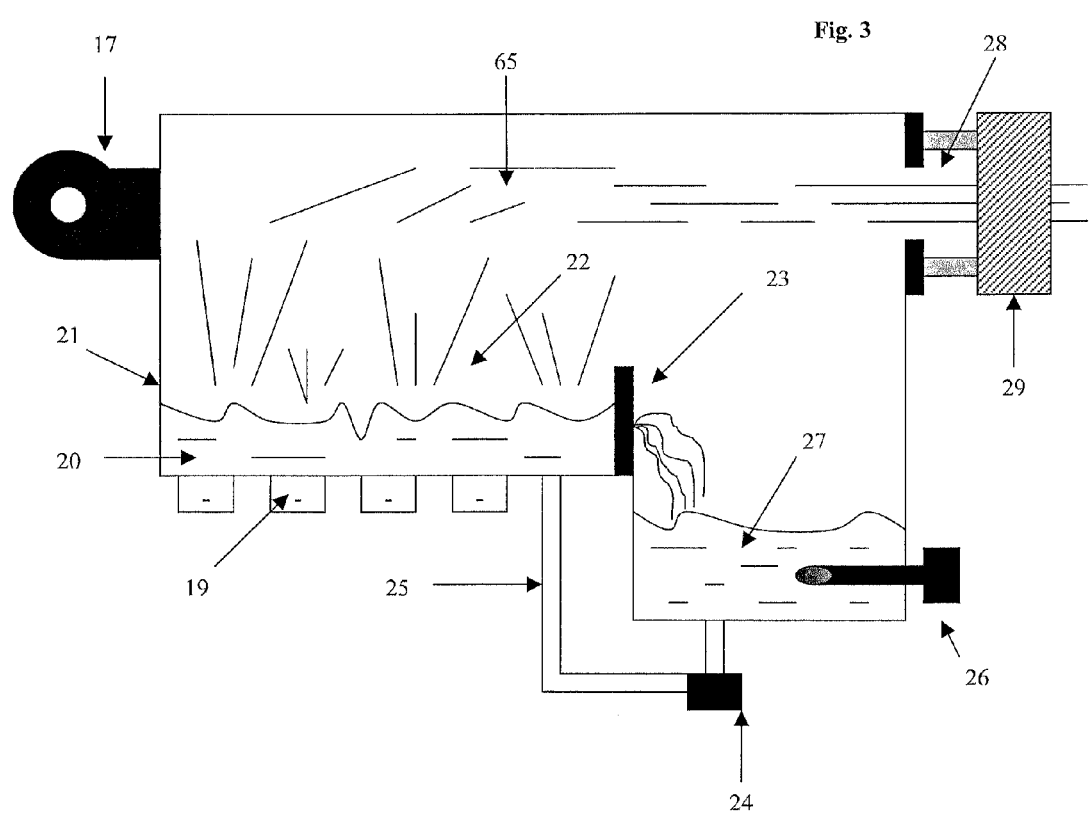

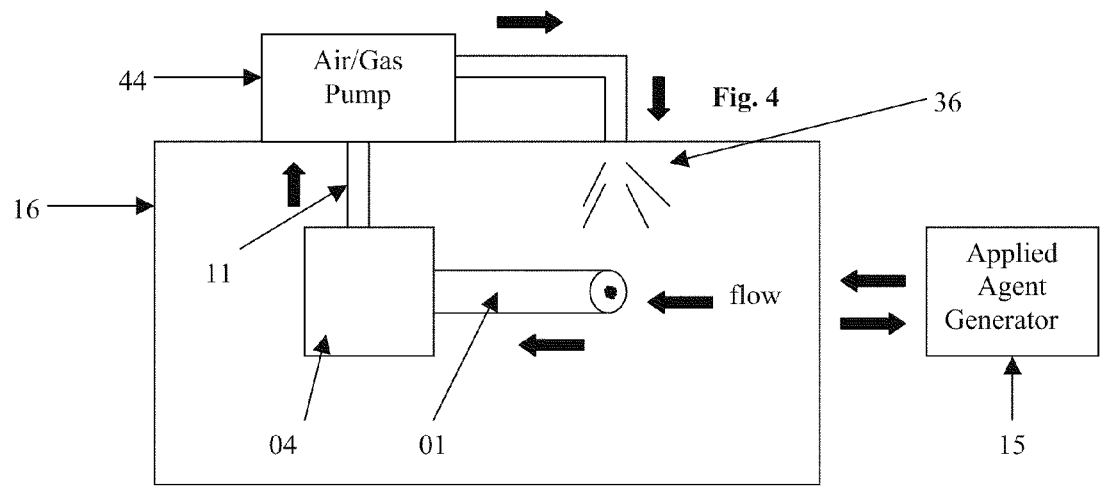
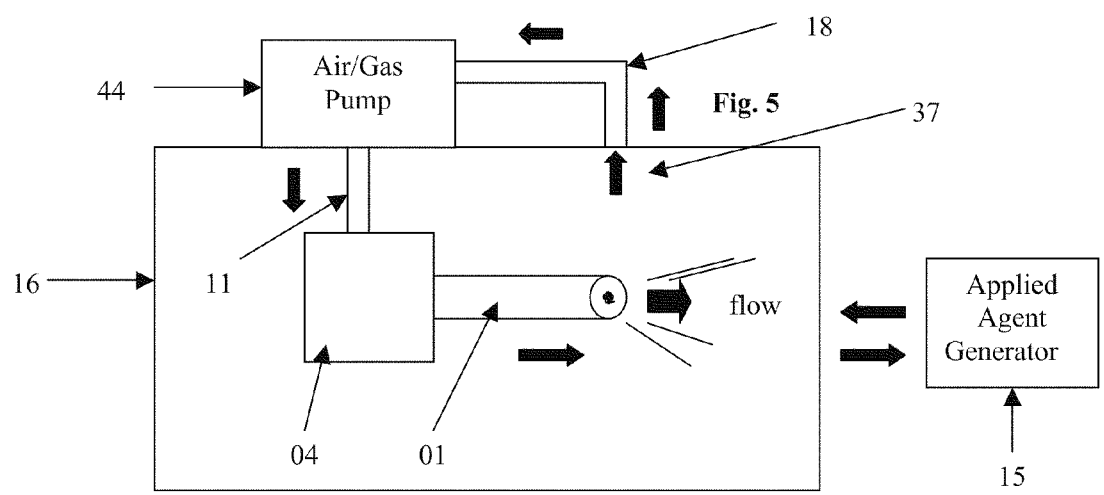

Fig. 13

- 39 → ← 35
- Exhaust Filter(s) ← 54
- 15 — Applied Agent Generator →
- 35
- 16 — Sterilization Chamber*
- 60
- 35
- 52
- 51 → Fan / Blower
- 53 → HEPA Filter(s)
- 35 → ← 38

METHODS AND APPARATUSES FOR APPLYING AGENT TO OBJECTS

CROSS-REFERENCE TO RELATED APPLICATIONS

This application claims priority from U.S. Non-Provisional application Ser. No. 12/567,428, filed on Sep. 25, 2009, which claims priority from U.S. Provisional Application Ser. No. 61/100,029, filed on Sep. 25, 2008, and expressly incorporated by reference herein in its entirety.

TECHNICAL FIELD OF THE INVENTION

The present invention relates to improved disinfection apparatuses and methods for use of those apparatuses, including but not limited to the simultaneous or non-simultaneous, sanitization, disinfection, high-level disinfection, or sterilization of one or more internal and exterior surfaces, or areas, of objects or spaces, as well as the airborne delivery of various types of agents, for various purposes, to an area, and without limitation, their surfaces. These areas may include one or more surfaces that are interfaced or articulated.

BACKGROUND OF THE INVENTION

The complete and assured sanitization, disinfection, high-level disinfection, or sterilization of devices, tools and other objects in industries such as but not limited to the health care industry, has always been a challenge in terms of processing time, cost, engineering tradeoffs, toxicity, safety, and overall effectiveness. Currently, the available choices are liquid disinfection, typically referred to as a "wet" method, and various airborne methods, typically referred to as a "dry" method. The dry method can include, but is not limited to, gases, aerosols, and processes that use steam as a carrier gas for the disinfecting composition or solution. All processes that do not include liquid immersion are generally considered to constitute a dry method even if the agent used has a liquid phase.

Immersion of an object in liquids known in the art for sterilization or disinfection is a relatively simple method that is cost effective, and offers fast cycle times that are typically measured in hours. However, it also presents problems related to reproducibility and quality assurance due to the potential for bubbles to form on the inner surfaces of complex instruments, including endoscopes, which prevent cleaning solution contact with interior surfaces, such as lumens or channels. Another method for cleaning devices such as endoscopes is known to those skilled in the art, but generally involves several sequential steps or activities such as, but not limited to, wiping the device to remove any unwanted debris or contaminants and then placing the endoscope in a washer and interfacing it with a hose, or other means known to those skilled in the art (herein called "supply tube"). The supply tube enables various liquids including but not limited to, surfactant, high purity rinse water, and disinfectant/sterilant, to be moved through the various channels and lumens of the endoscope at various stages of the cleaning process. The outside of the endoscope is also exposed, preferably simultaneously, to these same liquids at various stages of the cleaning process. After the final rinse stage, the endoscope is dried in a manner known to those skilled in the art including, but not limited to, being dried within the processing chamber, or removed from the washer and dried outside of the processing chamber.

The current art can be improved in various ways including, but not limited to: (1) decreasing the time required to achieve the desired anti-pathogen/toxin/fungal/sporicidal effect on both the internal and external surfaces as well as any interfacing/articulating surfaces of an object or endoscope (2) reducing the risk that "air bubbles" will prevent full contact of the disinfectant/sterilant solution with all inner surfaces of an object or endoscope (3) reducing the drying time for an object or endoscope, and (4) reducing or eliminating the deleterious effect of the disinfectant solution and/or disinfecting process on the materials that are used to construct the object or endoscope. The methods and apparatuses of the present invention address these needs by decreasing the time to efficaciously complete the essential steps while achieving a satisfactory result.

In general, liquid disinfection/sterilization creates a major corresponding drawback in that the finished product remains wet, and therefore unsuitable for packaging and/or storage. The deployed or applied disinfecting agent(s) or substance(s) must have limited toxicity, be reasonably safe as well as compatible with those materials comprising the instruments and devices to be disinfected/sterilized.

Gaseous agents used in the prior art for sterilization are very limited in terms of medical applicability. Steam or dry heat sterilization is effective, but many medical devices and instruments are incompatible with the degree of heat required for this process. So-called "cold sterilization" is an alternative, but the only currently available cold sterilization agents in use in hospitals are ethylene oxide and hydrogen peroxide in various forms that include, but are not limited to plasma. U.S. Pat. No. 4,512,951 (Koubek, 1983), which is incorporated herein by reference in its entirety, including any references cited therein, teaches using hydrogen peroxide to sterilize medical articles by causing hydrogen peroxide-water vapors to deposit a film of liquid on the medical devices. The liquid film is then caused to be evaporated. Hydrogen peroxide vapor is susceptible to humidity that can reduce the efficacy of the process.

Ethylene oxide (EtO) is carcinogenic, toxic and dangerous and, although effective, is only used as a last resort for instruments and devices that cannot be subjected to other modalities. In addition, after being exposed to EtO, items cannot be used for long periods to allow "off-gassing" or aeration of the EtO. According to the UNC School of Dentistry, the complete EtO cycle, including aeration, can last as long as 24 hours. The newer technology utilizing hydrogen peroxide plasma is an alternative, however, it is very expensive, and the technology requirements have translated to only small size sterilization chambers. To date, it has not been capable of sterilizing certain instruments including, but not limited to, endoscopes. Endoscopes generally contain small lumens and/or channels and the hydrogen peroxide plasma has difficulty in maintaining its effectiveness throughout the length of the lumen.

Without being limited to a mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) to kill the bacteria, virus, fungus, spores, neutralize a toxins, or render a virus, or protein structure incapable of replication or to otherwise interfere with the target's cellular physiology, or to destroy or neutralize the toxin. These chemically reactive liquids may be provided as an aerosol.

Prior art has taught that relatively quick disinfection and sterilization of objects can be achieved by their exposure to an aerosol of a disinfectant/sterilizing agent created by ultrasonic nebulization. U.S. Pat. No. 4,366,125 (Kodera et al., 1980), which is incorporated herein by reference in its entirety, including any references cited therein, teaches that an aerosol, created by ultrasonic transducers and consisting of hydrogen peroxide, can contact surfaces targeted for sterilization. Ultraviolet-ray lamps are then synergistically used in concert with the applied aerosol to achieve sterilization of the targeted surfaces. Generally, the prior art also describes apparatuses and methods where the aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are typically made from lead-zirconate-titanate-four (PZT-4) or other piezoelectric materials. This material is coated with a conductive coating (i.e., an electrode material) that enables an electrical signal to energize the transducer and causes it to emit high frequency pressure (energy).

G.B. Patent No. 1,128,245, (Rosdahl et al., 1968) which is incorporated herein by reference in its entirety, including any references cited therein, describes a device for disinfecting apparatuses and instruments, including medical instruments. This apparatus also generates a mist of disinfectant, including hydrogen peroxide, by means of an ultrasonic aerosol generator. According to Rosdahl et al., this patent was "primarily adapted for the disinfection of small medical instruments such as scalpels, tongs, syringes, or the like, positioned on a grid in a container" (pg 3 col. 23-30). However, another separate intended use for a second described apparatus was for disinfecting interior surfaces of objects such as the interior of tubing used for "breathing apparatuses" and "heart lung machines" (pg 1 ln 30-36 and pg 2 ln 95-101).

Rosdahl et al. is clearly distinguished from the present invention in that it is silent with respect to simultaneously disinfecting both the interior and exterior surfaces of an object. Rosdahl et al. also does not teach a method for simultaneously sterilizing/disinfecting and drying the outside and interior surfaces/lumen of an object. Most importantly, Rosdahl et al. does not teach how the apparatus could effectively and efficaciously be "connected" to the object (pg 2 ln 95-101) in a way that enables all of the interfaced/articulated surfaces to be sanitized, disinfected, high level disinfected, or sterilized. The pressurized air in Rosdahl et al. is supplied by way of a fan etc. or carrier gas, (pg 2 ln 48-49) and is used to both move the generated aerosol to perform the disinfection function, and to dry the objects placed within the enclosed area of their described apparatus after disinfection. Rosdahl et al. incorporated "a heating element to dry the air in the flow path of the carrier gas, to increase drying efficiency" (pg 3 ln. 123-127). The use of a heating element in the flow path of a gas stream taught in U.S. Pat. No. 6,379,616 (Sheiman, 1999), is incorporated herein by reference in its entirety, including any references cited therein. Sheiman also teaches the use of ultrasonic transducers to generate aerosol. The heater is located about the inlet conduit of the apparatus and is designed to heat the aerosol, which encourages its condensation on or within the article. It is important to note that Sheiman is silent regarding the use of the apparatus or a secondary apparatus to interface and sanitize, disinfect, high-level disinfect, or sterilize, the interior of an object or device, as well as the simultaneous or non-simultaneous cleaning of both the interior and exterior of objects.

Ultrasonic nebulizers have a unique advantage in that they can create small aerosol droplets less than 5 microns in size. The size of the droplets enables them to penetrate small cracks and crevices and to behave like a gas due to Brownian movement and diffusion. In addition, the cloud is able to form a very thin coating, deposition, or film over various surfaces that are inherent to this technology and method. The thin coating, film, or deposition of sterilant or disinfectant is able to dry much faster than coatings created by aerosol containing droplets that are much larger in diameter. It is also theorized that the vapor component resulting from the evaporation of the droplets, contributes to the overall efficacy of the process.

U.S. Pat. No. 4,366,125, (Kodera et al., 1980), which is incorporated herein by reference in its entirety, including any references cited therein, teaches that heated H2O2 is more efficacious than H2O2 used at room temperature (col. 1, line 19-25). In other words, (Kodera et al., 1980) teaches that the efficacious nature of a liquid agent can be increased as it is heated to temperatures higher than ambient temperature. This is desired, without limitation, in the present invention. The text entitled, "Aerosol Technology" by William C. Hinds (1982), which is incorporated herein by reference in its entirety, including any references cited therein, also taught that the size of the aerosol particles produced by ultrasounic means are not only affected by the frequency of the transducer operation, but also by the surface tension and density of the liquid.

It is commonly known that heating a liquid to a temperature less than its boiling point will reduce its surface tension. William C. Hinds (1982) established that the higher the temperature of the liquid, the lower the liquid's surface tension, resulting in smaller sized aerosol particles. This principle is incorporated without limitation, in the present invention. In the same text he also taught that smaller diameter particles demonstrate characteristics such as but not limited to, a lower settling velocity, a higher diffusion coefficient, and a higher Brownian displacement (movement), which is desired, without limitation, in the present invention. Hinds further taught that ultrasonic aerosol generating transducers can heat the surrounding liquid (page 382). This is also desired, without limitation, in the present invention.

It has been difficult and time consuming applying current devices and methods to disinfect or sterilize both the exterior and interior surfaces of tools or equipment, e.g., endoscopes, in a single cleaning cycle or process due to their complex construction including narrow lumens of various lengths. The limitations of the prior art are further indicated by the failure or problems, which various anti-pathogen/toxin/fungal/ sporicidal agents or substances have in contacting, and/or rapidly achieving an efficacious result on the surfaces of the endoscope or object that are interfaced/articulated with any coupling(s) or other device.

"Flash" sterilization is also needed in industries such as, but not limited to the health care industry. It is commonly used for quick sterilization and turn around of various objects immediately needed for or during surgery. Flash sterilization methods that include the use of steam under pressure at recommended temperatures of approximately 270 degree Fahrenheit for approximately three to ten (3 to 10) minutes, are generally representative of the current art. The object that is flash sterilized must then cool down before it is used, taking valuable time. A need exists in the industry to further reduce the total amount of time it takes to clean, sterilize or disinfect, and deliver a surgical tool on demand within a reasonable period of time. The present invention can, without limitation, decrease the total cycle time needed for rapid sterilization of medical devices by providing a means to quickly sterilize or disinfect objects whose construction materials are thermally sensitive and cannot be flash sterilized by current means.

The methods and apparatuses of the present invention address the need for a quick and effective way to fully sanitize, detoxify, disinfect, high level disinfect, or sterilize both the interior and exterior of medical devices, and objects. In addition, this may without limitation, be accomplished while still enabling all surfaces of the object or endoscope to have contact with the anti-pathogen/toxin/fungal/sporicidal agent(s) or substance(s) including surfaces of the object or endoscope that are interfaced/articulated with any coupling(s) or other device.

There is a continued need to increase both the efficacy and effectiveness of a system that offers shortened cycle times. The present invention addresses these issues. One such means in the present invention utilizes thermal forces by cooling or decreasing the temperature of the objects themselves, the atmosphere in which they reside, or the targeted area for the administration of an aerosol as well any surfaces in that area, prior to the administration of the aerosol.

Prior art has taught the step of cooling an enclosed area and its surfaces before the administration of a hydrogen peroxide disinfectant, however the hydrogen peroxide was first vaporized into a gaseous state before its administration, and the cooling step was intended to condense the vaporized hydrogen peroxide onto the intended surfaces, as taught in U.S. Pat. No. 4,512,951 (Koubek et al., 1983), which is incorporated herein by reference in its entirety, including any references cited therein. More specifically, Koubek et al., teaches a method of sterilization where a liquid of aqueous hydrogen peroxide is vaporized, and the vapors are delivered into an evacuated sterilizer chamber. The articles to be sterilized are cooled prior to the introduction of the vapor (or are cooled by the evacuation of air from the sterilizing zone) to a temperature below the dew point of the entering vapors. The condensing vapor deposits a film of liquid on all such cool surfaces (col 2, line 40-51). Koubek et al., also mentions in Claim 2 that the result of vaporization was a mixed "gaseous vapor" consisting of hydrogen peroxide and water vapor free of solid contaminants.

U.S. Pat. No. 4,952,370 (Cummings et al., 1988), which is incorporated herein by reference in its entirety, including any references cited therein, teaches a similar method of sterilization where a liquid of aqueous hydrogen peroxide is also vaporized into a gaseous state before its administration into an evacuated sterilizer chamber. However, Cummings et al., teaches improvements to the art where the hydrogen peroxide-water vapor is applied under vacuum to surfaces that are below 10 degree centigrade, or surfaces in an environment that are both below 10 degree centigrade and above 10 degree centigrade. The cold surfaces mentioned in Cummings et al., were not cooled to accentuate or enhance the process, but were surfaces of components that were inherently cold for their own operational purposes. This is mentioned in sections such as (col 2, line 4-9), (col 2, line 29-33), and (col 4, line 67 to col 5, line 2).

U.S. Patent Application No. 2005/0042130 A1 (Lin et al., 2003), which is incorporated herein by reference in its entirety, including any references cited therein, claims the use of an applied vacuum to move an ultrasonically derived aerosol, consisting of a sterilant, throughout the area of an enclosed chamber. The use of vacuum pressures below atmospheric pressure was also mentioned as well as the possibility that vacuum pressures lower than 5 tons lower than atmospheric pressure would likely "enhance the results", and that using a vacuum pressure low enough to vaporize the sterilant generally enhances sterilization (pg. 2, paragraph 28). However, Lin et al, was silent with respect to how the lower vacuum pressures would "enhance the results" other than any enhancement that vaporization of the aerosol might bring. Lin et al, was also silent with respect to the amount of time that is needed to elapse between lowering the pressure within the enclosed chamber and the application of an aerosol, in order to obtain the needed or desired level of efficacy. (Lin et al., 2003) was silent with respect to cooling any surfaces within the sterilization chamber or applying the aerosol to any cooled surfaces.

It is important to note that Lin et al, did not mention any process or method to heat the liquid of the aerosol or cool the surfaces in the sterilization chamber before or during the delivery of the aerosol, or any means to encourage condensation if the liquid was vaporized. In fact, the 5 torr negative pressure that was used by Lin et al. to generate their findings was reported to be sufficient enough to disperse the mist within the sterilization chamber (pg. 2, paragraph 28), but was never mentioned to have cooled the surfaces within the sterilization chamber or to have that intended effect.

In addition, it is important to note that the cooling of a targeted environment(s) and/or the surfaces contained therein addressed by the present invention is intended, without limitation, for a completely different application and purpose. The present invention utilizes the principals of aerosol behavior to increase the performance of the process of the present invention, and not the condensation of a gas as taught in the prior art. This is further addressed in the present invention.

By comparison, the current invention utilizes, without limitation, the cooling of the targeted environment(s) and its surfaces to enhance the performance and efficacy of the aerosol administration process and not to condense a gas as taught by the prior art.

SUMMARY OF THE INVENTION

The present invention generally relates to a combination of various apparatuses and methods for the sanitization, detoxification, disinfection, high level disinfection, or sterilization of both the interior and exterior surfaces of an object or medical device, including any articulating surfaces of interest, or plurality of objects within one or more closed space(s), closed system of space(s), or chamber(s), of any space, size, shape, configuration, or construction, that is either sealed or unsealed (hereinafter called "sterilization chamber"). In order to accomplish this, anti-pathogen/toxin/fungal/sporicidal agent(s) or substance(s) are first created, generated, and/or administered in or into the sterilization chamber. It is preferred without limitation, that the objects, e.g., endoscopes, are washed according to the manufacturer's recommendations or methods common to the industry, before being placed inside of the sterilization chamber. However, the washing and cleaning activities can also take place within the sterilization chamber prior to the application of the anti-pathogen/toxin/fungal/sporicidal agents(s) or substance(s).

According to an embodiment, any anti-pathogen/toxin/fungal/sporicidal agent(s) or substance(s) to be applied or used (hereinafter "applied agent"), may be in the form of a gas, vapor, plasma, or aerosol. It is preferred in the present invention that the "applied agent" is an aerosol, including, but not limited to, any acidic oxidizer, generated by one or more ultrasonic nebulizer(s). Transducers of any design, frequency, or construction may be used. The aerosol may be created by any means and may be of any concentration, number, size, or density, however it is preferred, without limitation, that the aerosol generally includes droplets whose size is five microns or less. It is preferred without limitation that the aerosol has a higher rather than lower mass concentration or density of droplets. In addition, any substance may be applied to neutralize any chemical residue on the interior or exterior of an object and/or device.

As previously discussed, the prior art is limited because of the difficulty that an "applied agent" has in reaching the interior surfaces of objects, lumen or channels found in an endoscope in a short period of time. Quicker turn-around times may be accomplished by improving the current art by means including, but not limited to: decreasing the processing time or exposure time to the "applied agent", and decreasing the drying time of the object.

The prior art is further limited because of the difficulty of the "applied agent" or substance to reach surfaces that are interfaced/articulated with a coupling(s) or other devices or components.

The present invention addresses the failure of the prior art to treat the articulating surfaces of an endoscope and coupling by incorporating an innovative porous and/or permeable interface between the endoscope and coupling. This innovative porous and/or permeable interface assures that the "applied agent" is able to reach the entirety of the internal spaces and surfaces, including endoscope lumens, channels, internal and external spaces and surfaces. One of the critical features of this solution is the design of the interface between the supply of negative or positive air/gas pressure used to bring the "applied agent"(s) and the surfaces of the endoscope. The porous and/or permeable interface of the present invention not only provides the necessary positive or negative air/gas pressure, but more importantly, it is able to do so while still insuring that all of the surfaces including the interface have sufficient exposure to the "applied agent". While this innovative system and method could be applied to other forced air sterilization systems/"applied agent(s)", it is preferred in the present invention that transducer based ultrasonic nebulization is utilized. It is also important to note that this particular aspect of the present invention could easily be adapted for use with any "applied agent" that can be applied to any surfaces of a device or endoscope in liquid form such as, but not limited to, a jet or stream of disinfecting or sterilizing liquid or mixture of liquids as taught by U.S. Pat. No. 5,425,815, (Parker et al., 1995) incorporated herein by reference in its entirety.

These advantages include, but are not limited to: 1) the ability to offer large chambers in which the devices to be disinfected can be positioned and treated without the technical challenges and costs associated with EtO and plasma; 2) the ability to build simple glass or plastic see-through chambers; 3) the ability to incorporate the addition of one or more polymer glove(s) or finger(s), built into the wall(s) of the closed space or sterilization chamber (similar in purpose and design to what is found in common laboratory or industrial glove boxes); 4) a very rapid processing times associated with the ultrasonically-generated aerosols, and 5) the ability to utilize a wide range of liquid disinfection or sterilization agents or mixtures of agents.

The aerosol created by the ultrasonic nebulizer(s) is generated by one or more ultrasonic transducers located below the surface of a liquid agent. The transducer(s) energy output is focused to either a point and/or an area near the surface of the liquid causing a surface disturbance, which results in the formation of an aerosol of the agent. Each transducer used in this apparatus is made from lead-zirconate-titanate-four (PZT-4), or other piezoelectric materials. The transducer(s) are operated in the frequency range of 0.001 to 10.0 MHz. The resultant aerosol is then evacuated from the reservoir and/or chamber in which it is generated, by a blower or other source of pressurized air, and moved into the designated or targeted space or closed area or chamber (hereinafter "sterilization chamber"). After its utilization in disinfecting or sterilizing a tool/device, the aerosol can then be circulated back to the aerosol generation chamber. This is taught in U.S. Pat. No. 4,366,125 Kodera et al. and Sheiman, U.S. Pat. No. 6,379,616. Recirculation can also be applied to any gas, plasma, vapor, aerosol, or other form of an "applied agent" or substance. The aersolized agent within the sterilization chamber may be moved within the chamber by a blower, fan, or other source of pressurized air.

U.S. Pat. No. 4,366,125, (Kodera et al., 1980), which is incorporated herein by reference in its entirety, including any references cited therein, describes an improved method and device involving ultrasonic nebulization that includes a means to heat the liquid which is nebulized. Kodera et al. teaches that heated H2O2 was more efficacious than H2O2 used at room temperature (col. 1, line 19-25). In other words, the efficacious nature of a liquid agent can be increased as it is heated to temperatures higher than ambient temperature. It is preferred, without limitation, that this advancement in the art is incorporated into the present invention.

Sheiman, U.S. Pat. No. 6,379,616 also improves upon the art by incorporating a heating element operatively coupled to the inlet of the closed area or sterilization chamber. According to Sheiman, the purpose of the heating element is to provide a means for effecting condensation of the aerosol within or on the article. This could also be incorporated into the present invention as described.

An embodiment of the present invention includes, without limitation, a possible means for radiating heat that is either operatively coupled to and/or about the outlet(s) of the closed area or sterilization chamber, or anywhere past the said outlet(s) and along the path of the air and aerosol as it is recirculated from the closed space or sterilization chamber back into the aerosol generation chamber(s). The purpose of this embodiment is to further diminish the diameter of the aerosol droplets before they reach the interior of the aerosol generation chamber(s). Heating, or other means to encourage rapid evaporation of the aerosol droplet will reduce the possibility of coalescence.

Another embodiment of the present invention includes, without limitation, the possible addition of a means to heat the floor within the closed space or sterilization chamber. A heated plate(s) could also be placed in this location. The purpose of having a heated surface at the bottom of the closed space or sterilization chamber is to repel the downward trajectory of the aerosol droplets as a result of gravity or thermal forces. In addition, droplets that contact the heated surface(s) may be re-energized or transformed into a vapor. This will contribute to the efficacious nature of the overall process and further decrease aggregate settling velocity. It is important to note that care should be taken in the placement of this heated surface so that an item(s) placed in the chamber is not itself heated. Increased heat of an object or device will cause the droplets to be repelled and will correspondently reduce the efficacy of the process.

An apparatus and method of another embodiment of the present invention comprises placing one or more endoscope(s), tool(s) or object(s), in a closed space or sterilization chamber with the addition of a means to enable the sanitization, detoxification, disinfection, high level disinfection, or sterilization of the interior area or surfaces, lumen(s), and/or channel(s) of the endoscope(s) or object(s). This means is able to interface or connect positive air/gas pressure or negative air/gas pressure (vacuum) line(s) with an object or endoscope inside of the sterilization chamber, and move "applied agent"(s) or substance(s) through the entire object or endoscope with sufficient volume and velocity without compromising the ability to treat contaminated areas or surfaces under or between that interface or connection and the medical device. It is preferred, without limitation, that the aforementioned object be washed, cleaned, or rinsed, prior to being placed into the sterilization chamber.

This particular embodiment utilizes an innovative pressure interface assembly including a coupling and interface or interface material combination that is unique for this application. This assembly is interfaced/articulated with the open end of the object or the distal end of the endoscope where the lumen/ports/working channels exit.

The pressure interface assembly has a number of components that include, without limitation, a porous and/or permeable interface or interface material (hereinafter called "interface") and a coupling. The coupling may be constructed from various materials such as but not limited to stainless steel, glass, cellulose, polyolefin, paper, polymer, natural or manufactured fibers or materials, that may be coated or uncoated, or constructed with combinations of these materials, or other materials known in the art. The coupling may be rigid, semirigid, or flexible. The coupling may have one or more ports or other means for attaching tubes, hose, pipes, duct, tunnels, conduit etc. (hereinafter called "delivery pipe") that supply air, gas, or the "applied agent" to the various spaces and surfaces of the pressure interface assembly and endoscope, including without limitation their internal spaces and surfaces, under positive or negative pressure.

The interface assembly may be used, without limitation, to dry the endoscope or to push or pull the "applied agent"(s) or substance(s) through any of its internal spaces, lumen or channels. The coupling can be designed so that one end is able to fit over an end of the endoscope and the other end of the coupling is designed to interface or connect with the delivery pipe. The coupling may also have various opening sizes on one end and various opening sizes on the other. The end of the coupling that is designed to fit over an end of an endoscope can also have one or more openings of various shapes and geometries. This opening can control the negative or positive air/gas flow or pressure in or out of the coupling. The internal dimensions of the coupling are designed to allow it to fit over the end of the endoscope and interface/articulate with the interface that is positioned between the coupling and the endoscope. The thickness of the coupling as well as the material(s) from which it is constructed, may also contribute to the efficacious performance of the interrelationship between the coupling, interface and endoscope, and their surfaces.

The interface is designed so that its internal dimensions provide a sufficiently tight fit with the outside dimensions of the endoscope or object. Attributes such as, but not limited to the width, thickness, porosity and/or permeability, flow of "applied agent" or gas, absorbency, as well as other chemical, mechanical, and physical (including durometer) properties of the interface may also contribute to an effective interface. The interface is either slipped over the end of the endoscope or at least a portion is mounted inside of the coupling, or combinations thereof. The coupling is then fitted over the end of the endoscope so that the endoscope interfaces sufficiently with the interface material and the interface material interfaces sufficiently with the coupling. The coupling is designed so that its internal dimensions provide a sufficient fit with both the contacted interface material and the endoscope. In certain situations, the thickness of the coupling material may also contribute to a sufficiently sealed or interfaced system.

Attributes such as but not limited to the interface material utilized, porosity and/or permeability of the interface, absorbency of the interface, as well as other chemical, mechanical, and physical (including durometer) properties, the interface thickness and width, the fit of the interface to the endoscope or object, the pressure exerted by the fit of the coupling to the interface and endoscope or object, and the distance the coupling overlaps on the interface material, control the rate of air/gas flow through the interface which then directly impacts the air/gas pressure differential between the inside and outside of the coupling.

It is important that the air/gas pressure differential be controlled so that a sufficient air/gas pressure differential exists to achieve an anti-pathogen/toxin/fungal/sporicidal effect on both the area and surfaces under the interface and the internal surfaces inside of the endoscope. These variables can be optimized for each object or endoscope configuration and coupling configuration based on, but not limited to, its external and interior dimensions, choice of permeable and/or porous material, internal area, and number, size and length of their interior areas.

There are two main components or features of an effective interface in this assembly. First, the interface must be porous or permeable. This allows the "applied agent" to pass through it. The air/gas, as well as the "applied agent" (if applicable) may also, without limitation, pass through the interface at a controlled and/or limited, but effectual rate. The passage of the "applied agent" through the interface material allows the area and surfaces under the interface material to be exposed to, and acted upon, by the "applied agent" in order to achieve the desired level of sanitization, detoxification, disinfection, high level disinfection, or sterilization. The interface may have absorbent characteristics to improve its efficacy. The composition of the interface material is not limited to but could be as simple as cotton gauze or some other substrate made of natural or manufactured fibers. The interface may also be constructed from one or more layers of various materials or combinations of materials such as but not limited to, cloth, gauze, manufactured fibers, synthetic fibers, natural fibers or materials, cellulose, polyolefin, polymer, or other materials known in the art, in order to control attributes such as, but not limited to, absorbency, and the flow rate or passage of the "applied agent" through the interface material as desired.

The limitation and/or control of the rate of flow of air/gas and/or "applied agent" allows the present invention to create an effective negative or positive air/gas pressure to move the "applied agent" through the interior space, lumens, and/or channels of the endoscope, as well as through the interface. For instance, if a vacuum is applied to the coupling interfaced/articulated with the interface material, the "applied agent" will be pulled through both the interface material and/or the areas of articulation as well through the interior space and/or lumens or channels with sufficient velocity to assure anti-pathogen/toxin/fungal/sporicidal activity on the surfaces throughout the length of the interior area, lumen, or working channels of the object or endoscope and in the area and on the surfaces under the interface.

The second feature of an effective interface involves the application and/or control of an effective pressure exerted on the interface as it contacts the object or endoscope. This assures a sufficient flow of "applied agent" through all areas of the interface and results in obtaining the desired level of sanitization, detoxification, disinfection, high level disinfection, or sterilization of the entire area and surfaces under the interface. It is preferred without limitation that the pressure exerted on the interface is evenly distributed.

According to another embodiment, the applied pressure is effectual and efficacious. The exerted pressure on the interface can result from the interface/articulation of the coupling and interface material with the endoscope. The effectiveness of the interface/articulation may also be augmented or optimized by the application, bonding, or interposition of one or more layers of various materials or combinations of materials such as but not limited to, cloth, gauze, manufactured fibers, synthetic fibers, natural fibers or materials, cellulose, polyolefin, polymer, or other materials known in the art. The exerted pressure on the interface material can result from, or be further controlled or optimized, by the interface/articulation of the coupling and interface material with the object or endoscope. It may be further controlled or optimized by the use of an inflatable pillow, balloon, bladder, reservoir, or other inflatable or expandable means or material (hereinafter called "balloon") between the coupling and interface material, between the endoscope and the interface material, between the endoscope and the coupling, on the internal surface of the interface, and/or around the coupling. The balloon can be constructed of and/or have its outermost layer constructed of this interface material and function as the interface layer. In either case involving the balloon, varying the amount of pressure inside of the balloon controls the pressure exerted on the interface. Additional means may be used to exert pressure on the coupling, interface material, and endoscope in order to create at least a minimum working interface. For example, a clamp that fits over and is used to apply pressure to the coupling, interface material and endoscope may be used to create a sufficient working interface. In another example, a ring of material can be incorporated into the coupling and the ring in a manner to exert evenly distributed pressure on the interface material.

It is also possible to exclude the interface component of the pressure interface assembly, and cause the coupling to function as an interface to the endoscope; this feature represents an embodiment of the pressure interface assembly in its simplest form. In this alternative, the entire coupling, part of the coupling, or the end of the coupling that interfaces with the object or endoscope, is constructed from, or is laminated, glued, cemented, adhered, or otherwise attached, to the interface. Effective and preferably evenly distributed pressure can be exerted on the interface material by means previously discussed, and can include, but not limited to the exertion of pressure by the inflation of an inflatable pillow, balloon, bladder, reservoir, or other inflatable or expandable means or material (balloon) either between the interface layer and the coupling, inside of the coupling walls, or on the exterior surfaces of the coupling. Everything previously discussed pertaining to the coupling and seal material applies to this embodiment. In general, the coupling is designed, constructed, treated, or processed, so that a pressure differential is able to be established that results in the effective flow of an applied agent or substance through both the interior space of the endoscope and the interface that is in contact with the endoscope, resulting in an anti-pathogen/toxin/fungal/sporicidal effect on areas and surfaces that include, but are not limited to, the areas and surfaces surrounding and under the seal material.

Another embodiment of the present invention includes the supply of air/gas, that is under either negative or positive pressure, to the pressure interface assembly by using a means such as, but not limited to, a vacuum pump, air/gas pump, pressurized air source, fan, or blower. This air pressure serves several functions. First, the positive and/or negative air/gas pressure can be applied to the pressure interface assembly at the beginning and/or end of the treatment, sanitization, detoxification, disinfection, high level disinfection, or sterilization cycle, or at any time during the entire cycle, in order to move air/gas or dry and/or heated air/gas through the interior space, lumens, and/or channels of the endoscope. This will remove any moisture present in these areas. One or more heating element(s) placed in the air stream before the pressure interface assembly can also, without limitation, provide heated air (Rosdahl et al. pg 3 Col. 123-127). It is preferred, without limitation, that any air from outside of the sterilization chamber that is pulled, drawn, pushed, or otherwise moved into the sterilization chamber and/or the endoscope be filtered before its entry into the sterilization chamber and endoscope. Any high efficiency filter such as a HEPA filter(s) or other filter(s) that is known to those skilled in the art and/or is acceptable in the industry may be used. The air/gas may be filtered with any type of filter acceptable to those skilled in the art before its exit from the sterilization chamber. The object or endoscope may be dried by heated and/or dehumidified air within the sterilization chamber and/or before its entry into the sterilization chamber.

The positive air/gas pressure or negative air/gas pressure is also intended, without limitation, to move the "applied agent" or substance through the interior space of the endoscope as well as through the interface and the area under the interface. It is preferred, without limitation, that if a negative air/gas pressure is supplied to the coupling that a pressure differential is established. This will cause, without limitation, the flow of air/gas and "applied agent" or substance from the sterilization chamber, to pass through the interface material, the area under the interface, the internal space within the endoscope, and into the coupling. Once in the coupling, the air/gas and/or "applied agent" flows into the attached tubes, hose, pipes, duct, tunnels, conduit, or delivery pipe, where it is eventually vented back into the sterilization chamber, or through a filter and into the outside environment.

The "applied agent" may also, without limitation, flow into the coupling under positive air/gas pressure. It is preferred, without limitation, that the "applied agent" or substance is pulled from the sterilization chamber, or a chamber where it is generated, and flowed into the coupling via the attached tubes, hose, pipes, duct, tunnels, conduit, or delivery pipe. It then flows, without limitation, out of the interface material, the area under the interface material, and through the internal space within the object or endoscope, and into the sterilization chamber. If generated in a chamber separate from the sterilization chamber, the "applied agent" or substance in this case, can without limitation, be separately delivered into the sterilization chamber.

Another embodiment of the current invention is the incorporation, positioning, or placement, of one or more biological indicator(s) and/or chemical exposure indicator(s) in or articulated with the pressure interface assembly. It is preferred in the present invention that the indicator(s) is placed or positioned inside the coupling. The indicator(s) provides a method of assuring that proper sanitization, detoxification, disinfection, high level disinfection, or sterilization has occurred within the pressure interface assembly.

An apparatus and method of another embodiment of the invention comprises the incorporation of a means to flow or circulate either filtered or unfiltered air/gas from outside of the apparatus into the sterilization chamber. This air/gas can also be flowed through the interior space, lumens, and/or channels of the endoscope inside of the sterilization chamber by using the same means that is used to supply positive or negative air/gas pressure to the pressure interface assembly that is interfaced with the endoscope. This air may be heated to remove moisture from any of the surfaces of the endoscope(s) within the sterilization chamber as well as the surfaces of their interior areas, lumen or channel(s). This activity can occur at any time including, but not limited to, before the application of the "applied agent" or substance. In addition, and without limitation, the completion of this activity at the end of the sanitization, detoxification, disinfection, high level disinfection, or sterilization cycle can reduce the entire cycle/processing time. When an "applied agent" or substance is applied, such as but not limited to an aerosol, this activity can also reduce the relative humidity in the sterilization chamber to ambient or below ambient levels. The incoming air can be, without limitation, effectively filtered with the use of any high efficiency filtering process, or other filtering means known in the art. The sterilization chamber can also be, without limitation, coupled to a filtered exhaust system to allow the incoming filtered air to replace air inside the chamber.

An apparatus and method of another embodiment of the present invention comprises the incorporation and use of any apparatus or methods know to those skilled in the art, to remove humidity from within the sterilization chamber(s) or other targeted area(s). This should not be confused with a fan or blower that was previously mentioned. The dehumidification apparatus may, without limitation, be placed or interface with or within the sterilization chamber(s) or other connected areas or spaces. The dehumidification apparatus may be operated any time after the application of the "applied agent". After the endoscope processing steps are completed and the sterilization chamber(s) or other targeted area(s) are dehumidified, the air/gas within these spaces may be filtered to remove substances such as, but not limited to, any remaining odors, chemicals, smells, vapors, aerosols, or gases. Any filtering means or level of filtering may be utilized that is known to those skilled in the art. The processed air/gas may be, without limitation, returned back to the sterilization chamber(s) or any space(s) connected to the sterilization chamber(s). This feature allows, without limitation, the system or process to be self-contained until the sterilization chamber is opened at the end of the operation cycle.

An apparatus and method of another embodiment of the present invention comprises the incorporation of a means for holding or positioning the endoscope so that all of its surfaces are exposed to the "applied agent" and drying cycle. An apparatus and method of another embodiment of the present invention comprises the inclusion of a means for holding or positioning the endoscope during the sterilization cycle. Currently many sanitization, detoxification, disinfection, high level disinfection, or sterilization systems cannot adequately address the problem with shadowing, or inadequate coverage, when one hard or impenetrable surface contacts another.

According to one embodiment of the present invention, the endoscope is held about its circumference with a loop, band or it is cradled, in one or more places with a porous, permeable, semi-permeable and/or absorbent material and the remaining material is then placed on hooks or other holding mechanisms positioned within the sterilization chamber so that the object or endoscope can hang in free space within the sterilization chamber. Without limitation, previous tests have shown that certain porous materials like glassine have shown sufficient permeability with this process to obtain a high level of disinfection on the internal side of the barrier material.

According to another embodiment of the present invention, the endoscope is placed on one or more beams or forks (hereinafter "Start Beams") that are located within the sterilization chamber. These beams or forks can be of various sizes and shapes and interplay or loosely interlock with opposing beams or forks (hereinafter "Opposing Beams") that can be of similar shape and size. During the application of the "applied agent" either the "Start Beam(s)" or "Opposing Beam(s)" move by way of various mechanical means know in the art, and take hold of the endoscope so that it is transferred from the Start Beams to the Opposing Beams or from the Opposing Beams to the Start Beams. This process can be reversed during the drying cycle(s). This process can be timed so that all surfaces receive a sufficient or efficacious exposure to both the "applied agent" and drying cycle.

According to an embodiment, it is more preferred, without limitation, that one or more endoscopes is placed within an enclosed area, chamber, or sterilization chamber, and the internal and external surfaces of the endoscope are simultaneously or non-simultaneously subjected to various combinations of activities including, but not limited to, washing, cleaning, rinsing, drying, disinfection/sterilization, in various orders, frequency, and duration. Some of these activities may not be undertaken. This embodiment improves the current methodology for the disinfection or sterilization of an endoscope.

The initial processing or cleaning of an endoscope in this embodiment incorporates activities already known to those skilled in the art. These activities may include, but are not limited to, (1) Wiping, or otherwise cleaning the endoscope in various ways known to those skilled in the art, to remove liquids, debris, contaminants, blood, mucus, feces, urine, or any other substances that are unwanted or undesirable; (2) Placing the endoscope into a chamber, washer, or other device or means for cleaning, washing, or otherwise disinfecting/sterilizing endoscopes or other objects (hereinafter called "washer"); (3) Securing or holding the endoscope within the washer, (4) Interfacing the endoscope with a hose, tube, or other delivery means known to those skilled in the art (hereinafter "supply tube") in which the supply tube enables various liquids including, but not limited to, surfactants, and high purity rinse water, to be moved through the various channels and lumen of the endoscope at various stages of the cleaning process; (5) Operating the washer to spray, cover, flood, or any combination thereof, of the inside or outside surfaces of an endoscope with liquids or compounds such as, but not limited to, surfactants or other cleaning liquids; (6) Operating the washer to subject, spray, cover, flood, or any combination thereof, various surfaces such as but not limited to, the inside and outside surfaces of the endoscope, with liquids or compounds such as, but not limited to, any liquid rinse (hereafter "rinse" or "rinse water"), which may be formed of any liquids or combination of liquids such as, but is not limited to, high purity water.

In order to improve the art and decrease the endoscope processing time, improvements are made after this particular "rinse" activity to the current art and are shown in the following embodiments. The endoscope processing or cleaning is completed in the current art by the following activities: (7) Applying a disinfectant to both the interior and exterior surfaces of the endoscope in various ways known to skilled in the art such as, but not limited to, pumping or spraying onto the various internal and external endoscope surfaces; (8) Rinsing the interior and exterior surfaces of the endoscope in various ways known to skilled in the art such as, but not limited to, pumping or spraying high purity water onto the various internal and external endoscope surfaces; (9) In many applications the endoscope surfaces may also, without limitation, be rinsed in a manner known to those skilled in the art, with a volatile solution such as, but not limited to, alcohol, and this can also replace the high purity rinse water mentioned above; (10) Drying the internal and external surfaces in a manner known to those skilled in the art; (11) Removal of the endoscope from the washer or chamber.

According to an embodiment, after the endoscope is treated with surfactant and, without limitation, rinse water, its internal and external surfaces may, without limitation, be dried before application of the "applied agent". The internal surfaces may, without limitation, be dried with air/gas flow through one or more supply tubes in a manner known to those skilled in the art, and the external surfaces may be dried with various means known to those skilled in the art. The application of the "applied agent" may be, without limitation, followed by another rinse water cycle, volatile liquid rinse cycle, and/or drying cycle. However, to further reduce processing time, it is preferred, without limitation, that the internal and external surfaces of the endoscope are dried in a final drying activity in a manner known to those skilled in the art, after the application of the "applied agent"(s). It is possible, without limitation, to skip the final rinsing activity(s) for reasons including, but not limited to, aerosols such as, but not limited to, ultrasonically derived aerosols, are able to be administered to the endoscope's surfaces as a thin film of a low concentration of peroxyacetic acid, which then breaks down into harmless components as it dries. This particular embodiment will improve the current art by significantly decreasing the overall processing time, as well as increasing the efficacy of the process.

According to an embodiment, after the endoscope is cleaned with surfactant and/or rinsed, the inside and outside surfaces of the endoscope are treated with one or more "applied agent"(s) in the form of an aerosol. It is preferred, without limitation, that the internal and external surfaces of the endoscope be dried in a manner known to those skilled in the art, before the applied agent(s) is applied. The "applied agent"(s) are created, generated, and/or administered in or into the sterilization chamber. It is preferred, without limitation, that the aerosol is any aqueous aerosol that is generated or created by any transducer or ultrasonic nebulizer of any construction and design. The "applied agent"(s) may be pushed or pulled through the endoscope with various means known to those skilled in the art. The agents may be, without limitation, first administered or deployed into the sterilization chamber and then pulled through the endoscope with a vacuum or negative air/gas pressure. This particular embodiment will improve the current art by significantly decreasing the processing time.

According to an embodiment, the "applied agents" may also be, without limitation, in the form of any gas, vapor, plasma, or aerosol. The prior art includes the use of pumping, jetting/spraying, or flowing agents as a liquid over the external surfaces as well as through the lumens and channels of an endoscope for disinfection/sterilization purposes, and are not claimed in the present invention.

According to another embodiment, after the various endoscope surfaces are treated with an agent, the internal surfaces, as well as external surfaces of the object or endoscope may be, without limitation, exposed to another rinse liquid comprising one or more liquids that include, but not limited to high purity water, all in a manner known to those skilled in the art. After the "applied agent" or final rinse liquid is applied, all of the endoscope surfaces may also, without limitation, be rinsed with a volatile solution such as, but not limited to an alcohol solution. The endoscope can then be removed from the washer and hung to dry.

According to another embodiment, and without limitation, the internal and external surfaces of the endoscope may be dried with means including but not limited to, dehumidification of the air within the chamber before the endoscope is removed from the washer. The supply tube may, without limitation, provide the air/gas that is used to dry the internal surfaces, and the various external surfaces are dried in a manner known to those skilled in the art.

An apparatus and method of an embodiment of the present invention, briefly summarized, comprises cooling or decreasing the temperature of the objects, the atmosphere in which they reside, or any or all targeted surfaces or areas, including the internal surfaces of an object(s) such as, but not limited to an endoscope, within the sterilization chamber(s). This is accomplished in the present invention via the use of one or more, or the combination of one or more, of any thermoelectric and/or refrigeration cooling system(s) to cool or chill any air or gas within the sterilization chamber, before and/or during the administration of the aerosol into the sterilization chamber(s) or other to targeted area(s). Cool air may also, without limitation, be moved through the endoscope or any other object by various means known to those skilled in the art, as well as addressed in the present invention, before or during the "applied agent" phase or applied aerosol. This cooling activity or process enables the present invention to utilize the principals of aerosol behavior to increase the efficacy or performance of the process of the present invention. Aerosol particles experience a force in the direction of decreasing temperature. By decreasing the surface temperature of the targeted surfaces, the administered aerosol, and especially an aerosol where the liquid was heated, is drawn towards those cooled surfaces forming a microfilm.

According to another embodiment of the present invention, the one or more structures, pillars, members, beams, forks, clamps, or other means to support, hold, cradle, suspend, position, or support the object(s) or endoscope(s) within the sterilization chamber, can have, without limitation, one or more means incorporated into their construction to disperse, or even pull in, any substances used for processing the object(s) or endoscope(s) such as, but not limited to, surfactant, rinse water, high purity rinse water, alcohol solution, "applied agent"(s) in any form, heated air/gas, and dehumidified air/gas. These substances may flow at any quantity, rate, or pressure. In addition, any part of the one or more structures, members, beams, forks, or other means to hold or support the endoscope(s) within the sterilization chamber can be, without limitation, effectively covered with any interface material or combination of interface materials, through which these substances may move or flow. This can help to insure that all of the surfaces of the object(s) or endoscope(s) including the interface material(s), have sufficient exposure to any substances used in the processing steps used inside of the sterilization chamber.

An apparatus and method of another embodiment of the present invention comprises a new and novel way to administer the "applied agent"(s) into one or more sterilization chamber(s) in which the object(s) or endoscope(s) are positioned. The sterilization chamber(s) can be, without limitation, effectively sealed or enclosed when used, and each has one or more valves, airlocks, or other effectively sealing door known to those skilled in the art (hereinafter called "valve(s)"). The valve(s) either directly or indirectly connect the sterilization chamber to a secondary chamber, as well as control the flow of any aerosol or "applied agent" from the secondary chamber into the sterilization chamber.

One or more object(s) or endoscope(s) are placed within the sterilization chamber(s), where they can, without limitation, be washed and dried in a manner known to those skilled in the art. The object(s) can, without limitation, also include any package(s) that are sealed, partially sealed, or hermetically sealed. The package(s) can also, without limitation, be constructed from, or include in its construction, at least an effective amount of Tyvek or other similar material. The package(s) can be, without limitation, placed on or and secured to any type of racks inside of the sterilization chamber(s). Before the application of the "applied agent" all surfaces, and environment, within the sterilization chamber(s) can be cooled to any temperature, in a manner known to those skilled in the art. Before application of the "applied agent"(s), the pressure within the sterilization chamber(s), or any connecting or shared areas or atmospheres, is reduced to a pressure including, but not limited to, any effective negative pressure, but preferably a full, or close to complete, vacuum. The sterilization chamber(s) can be, without limitation, positioned inside a larger sealed or at least effectively sealed chamber, enclosed area, or one or more interconnected areas (hereinafter called "Secondary Chamber"). The "secondary chamber" can be any size, shape, or geometry. The secondary chamber can, without limitation, be located anywhere outside of the sterilization chamber, and effectively connected to the sterilization chamber in one or more places. The pressure within this "secondary chamber" can be any pressure including, but not limited to ambient pressure.

However, it is preferred, without limitation, that the pressure within the secondary chamber is at least effectively greater than the pressure inside of the sterilization chamber(s). The pressure within the sterilization chamber may, without limitation, be maintained at any ambient or outdoor pressure, or even be slightly pressurized, and the "secondary chamber" can be effectively pressurized in addition to being filled with the "applied agent(s)". The secondary chamber is filled with the "applied agent"(s), either directly or indirectly. Any or all surfaces, or the environment, within the secondary chamber can be, without limitation, cooled with refrigerated or chilled air before, during, or after the application of the "applied agent(s)".

It is preferred, without limitation, that the "applied agent" be an aerosol containing substances including, but not limited to, any acidic oxidizer. Once the secondary chamber is sufficiently and effectively filled, the valve(s) are opened and the "applied agent"(s) is allowed to flow into and fill the sterilization chambers(s). The "applied agent"(s) can also flow, without limitation, through one or more of any filter(s) as it moves from the secondary chamber to the sterilization chamber. At this point, the air or gas pressure within the sterilization chamber(s) can be, without limitation, increased to any effective pressure. The air or gas pressure can also be increased in the secondary chamber as well. After the valve(s) are opened, additional amounts of "applied agent"(s) can, without limitation, be administered into the sterilization chamber(s) and any interconnected areas for any desired time period. The temperature of the air or gas(s) within the sterilization chamber(s) and any interconnected areas can also be increased to any effective temperature after the valve(s) are opened. Following an effective amount of time, the sterilization chamber(s) can be, without limitation, dried, dehumidified, and deodorized, before removal of the object(s) or endoscope(s).

BRIEF DESCRIPTION OF THE DRAWINGS

The drawing figures illustrate the best mode currently contemplated of practicing the present invention.

In the drawings:

FIG. 1 is a schematic view of a first embodiment of a disinfecting apparatus constructed according to the present invention;

FIG. 2 is a schematic view of a second embodiment of the disinfection apparatus of FIG. 1;

FIG. 3 is a schematic view of an aerosol generator used in the apparatus of FIG. 1;

FIG. 4 is a schematic view of a first embodiment of a sterilization chamber used in the apparatus of FIG. 1;

FIG. 5 is a schematic view of a second embodiment of a sterilization chamber used in the apparatus of FIG. 1;

FIG. 6 is a schematic view of a third embodiment of a sterilization chamber used in the apparatus of FIG. 1;

FIG. 7 is a schematic view of a fourth embodiment of a sterilization chamber used in the apparatus of FIG. 1;

FIG. 8 is a front isometric view of a first embodiment of an object holder used in the apparatus of FIG. 1;

FIG. 9 is a top isometric view of a second embodiment of an object holder used in the apparatus of FIG. 1;

FIG. 10 is a top plan view of a third embodiment of an object holder used in the apparatus of FIG. 1;

FIG. 11 is an end view of the object holder of FIG. 10;

FIG. 12 is a schematic view of a third embodiment of the apparatus of FIG. 1;

FIG. 13 is a schematic view of a fourth embodiment of the apparatus of FIG. 1;

FIG. 14 is an exploded, perspective view of a first embodiment of a pressure interface assembly utilized with the apparatus of FIG. 1;

FIG. 15 is a perspective view of the assembly of FIG. 14;

FIG. 16 is exploded, perspective view of a second embodiment of a pressure interface assembly utilized with the apparatus of FIG. 1;

FIG. 17 is a perspective view of the assembly of FIG. 16;

FIG. 18 is an exploded, perspective view of a third embodiment of a pressure interface assembly utilized with the apparatus of FIG. 1; and FIG. 19 is a perspective view of the assembly of FIG. 18.

FIG. 20 is a schematic view of a sterilization chamber with a thermoelectric air or gas cooling system(s) and/or refrigerated air or gas system(s), connected to the sterilization chamber in a loop.

FIG. 21 is a schematic view of a sterilization chamber with a dehumidification apparatus, a filter, and a thermoelectric air or gas cooling system(s) and/or refrigerated air or gas system (s), connected to the sterilization chamber in a loop.

FIG. 22 is a schematic view of a sterilization chamber with a dehumidification apparatus, a filter, a thermoelectric air or gas cooling system(s) and/or refrigerated air or gas system(s), and a separate chamber connected to the sterilization chamber.

FIG. 23 is a schematic view of a sterilization chamber illustrating a sealed door.

FIG. 24 is a top view of a pair of object supports with a plurality of openings formed therethrough.

FIG. 25 is a cross sectional view of an endoscope or object resting on object supports with an aerosol passing through a plurality of openings in the object supports.

FIG. 26 is a schematic diagram of two sterilization chambers connected to each other with a pressure valve.

FIG. 27 is a schematic diagram of two sterilization chambers connected to each with a pressure valve and a flow pipe.

FIG. 28 is a schematic diagram of a first sterilization chamber located within a second sterilization chamber.

FIG. 29 is a schematic view of a sterilization chamber with a refrigerated air system and vacuum source, connected via a flow pipe and filter, to a second chamber with a dehumidification apparatus, filter, and aerosol generator. One pipe connects the sterilization chamber to the aerosol generator forming a loop for gas/aerosol flow back to the aerosol generator.

FIG. 30 is a schematic view of a sterilization chamber with a thermoelectric air or gas cooling system(s) and/or refrigerated air or gas system(s), and vacuum source, connected via a flow pipe, to a second chamber with a dehumidification apparatus, filter, and aerosol generator, and a pressure source. One pipe connects the aerosol generator to the pressure interface assembly positioned within the sterilization chamber, while the other pipe connects the sterilization chamber to the aerosol generator forming a loop for gas/aerosol flow back to the aerosol generator.

FIG. 31 is a schematic diagram of one sterilization chamber with a dehumidification apparatus, a filter, and a thermoelectric air or gas cooling system(s) and/or refrigerated air or gas system(s). The sterilization chamber is also connected to two separate pipes. One pipe connects the aerosol generator to the pressure interface assembly positioned within the sterilization chamber, while the other pipe connects the sterilization chamber to the aerosol generator forming a loop for gas/aerosol flow back to the aerosol generator.

DETAILED DESCRIPTION OF THE PREFERRED EMBODIMENTS

Figure 1:
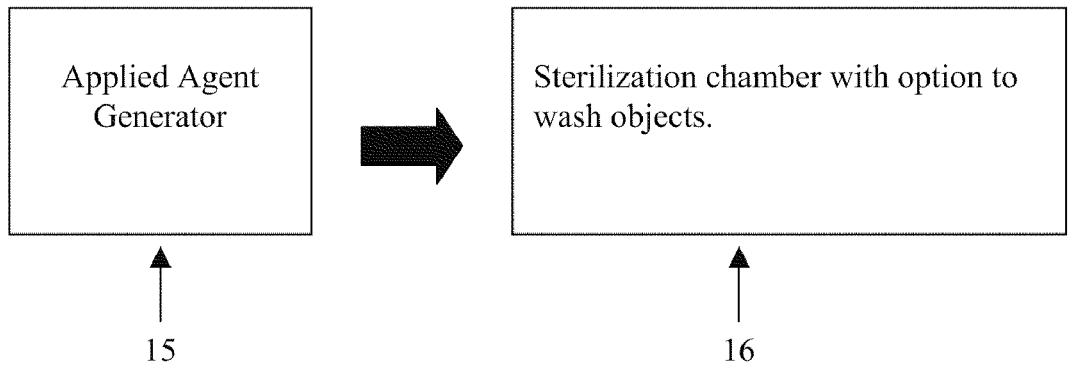
Figure 2:
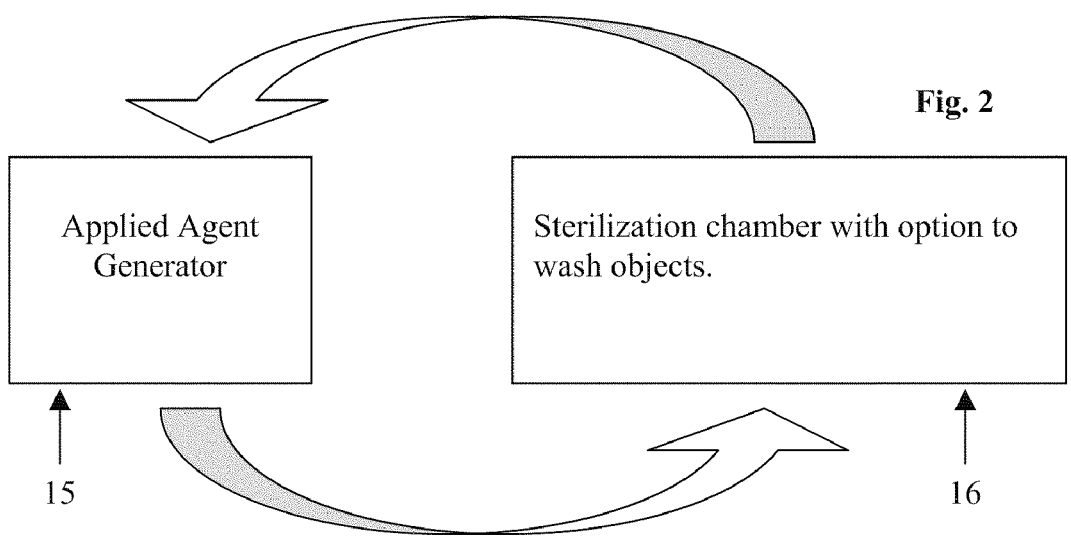

With reference now to the drawing figures in which like reference numerals designate like parts throughout the disclosure, the invention broadly comprises methods and apparatuses for the sanitization, detoxification, disinfection, high level disinfection, or sterilization of both the interior and exterior surfaces of any object such as, but not limited to, an endoscope (01) or plurality of endoscopes (01) (FIG. 5) within one or more closed space(s), closed system of space(s), or chamber(s) (herein called "sterilization chamber") (16), as well as and, without limitation, their surrounding atmosphere.

U.S. Pat. Nos. 7,641,130 and 7,871,016 both to Ricciardi et al. and U.S. patent application Ser. Nos. 12/567,428 and 12/637,310 both to Ricciardi et al. are all herein incorporated by reference in their entirety.

This is achieved or attained by the generation and/or administration of an "applied agent", or mixtures of these agent(s) or substance(s), in or into the sterilization chamber (16) in which the object(s) or endoscope(s) (01) is positioned or placed. It is more preferred, without limitation, that the "applied agent" or substance is in the form of an aqueous aerosol (65) that is generated by way of one or more ultrasonic device(s) (19), an example of which is shown in FIG. 3 and disclosed in co-pending U.S. patent application Ser. No. 11/509,332, which is incorporate herein by reference in its entirety as part of the present specification. It is also preferred, without limitation, that the aerosol be formed of an aqueous solution that contains a suitable disinfecting, sanitizing or sterilizing agent(s) or substance(s) that contains an acidic oxidizer, such as hydrogen peroxide and peroxyacetic acid. Any chemical neutralizing agent(s) or substance(s) can also, without limitation, be used and can be in any form including, but not limited to any liquid, gas, vapor, plasma, or aerosol.

One aspect of the present invention, is an improvement to the current art involving an innovative pressure interface assembly (68) (FIGS. 14-19) for the application of a positive or negative air/gas pressure to the internal space, lumens, ducts, channels or fiber optic shafts or tunnels (herein called "ducts") (08), of an object or endoscope (01), in order to apply or administer the "applied agent" or substance(s) such as but not limited to any gas, plasma, vapor, or aerosol, to the internal spaces and surfaces within these locations as well as the areas and surfaces that interface or articulate with the pressure interface assembly (68). This innovative pressure interface assembly and its interface, assures that the agent(s) or substance(s) is able to reach and coat, sanitize, detoxify, disinfect, high level disinfect, or sterilize, the entirety of the internal spaces and surfaces that are inherent to various objects including, but not limited to, endoscope designs, diameters, and especially lengths. The assembly (68) includes an interface material (02) that also assures that all of the surfaces of the object or endoscope in contact with the interface have sufficient exposure to the aerosol (65) of an "applied agent" (20) through either direct and/or indirect contact, for their sanitization, disinfection, high-level disinfection, or sterilization, depending on the agent used and the exposure time. For example and without limitation, any absorbent interface material may also indirectly deploy/transmit the "applied agent" (20) that is aerosolized, to the articulated areas and surfaces by the interaction or movement of the "applied agent" (20) through the interface material (02) formed from the selected material. The present invention also incorporates various other improvements to the current art.

It is preferred, without limitation, that the endoscope (01) is washed according to the manufacturer's recommendations or methods common or prescribed in the industry or field of art, before being placed inside of the sterilization chamber (16) and the application of the "applied agent" or substance(s) (20) to the endoscope. However, the object or endoscope can also be placed within the sterilization chamber (16) and the washing and cleaning activities can, without limitation, take place within the same sterilization chamber (16) prior to the application of the "applied agent" (20).

According to an embodiment, any gas, vapor, plasma, aerosol, or aerosol, may be utilized or applied and be created from any chemical, mixture, compound, or anti-pathogen/toxin/fungal/sporicidal agent(s) or substance(s) (hereinafter ""applied agent"(s)") (20), and it can be created, stored, produced, or generated either inside the closed space, closed system of space, sterilization chamber (16), or inside a separate chamber (15) that is connected to the closed space, system of closed space, or sterilization chamber (16) as shown in FIGS. 1-2 and FIGS. 4-5, 12-13, 20-23, 26-33.

According to another embodiment, the "applied agent" (20) may be in any form including, but not limited to, a gas, vapor, plasma, aerosol, or liquid. The "applied agent" (20) in liquid form does not include any liquid aerosols and is applied in a distinctly separate way. In particular, the "applied agent" (20) in liquid form is generally applied or administered in ways including, but not limited to, being pumped, poured, flowed, or sprayed, onto, or through various internal or external surfaces of an endoscope.

The "applied agent" (20) may be, without limitation, one or more or any combination of suitable compounds, mixtures, substances, or chemicals, in any concentration, number, size, or density. It is preferred, without limitation, that if an aerosol (65) is utilized, it is formed generally of droplets whose size is less than five microns. The aerosol (65) may have any mass concentration or density. It is further preferred, without limitation, that the aerosol (65) has droplets that are of a higher rather than lower mass concentration or density.

According to an embodiment, the atmospheric pressure within the sterilization chamber, or any connecting or shared areas or atmospheres, may be any negative pressure, including a full or close to full vacuum, before or during the deployment of any "applied agent" inside of the sterilization chamber, or through any pressure interface assembly or supply tube. This can also help to increase the efficacy of the process, and is known to those skilled in the art. Also, the "applied agent" can be either generated inside the sterilization chamber, or any separate, but connecting area to the sterilization chamber, that may or may not be controlled with a valve.

The amount of "applied agent" (20) that is generated and administered or applied can vary as necessary or desired. In addition, the application time and total exposure time of the "applied agent" (20) to the endoscope(s) (01) in the closed space or sterilization chamber (16) can also vary. The level of efficacy, result, outcome, or effect that is desired or needed, as well as the time needed to accomplish it, with the application of the "applied agent" (20) to any of the areas or surfaces within the closed space or sterilization chamber (16), pressure interface assembly (68), or endoscope (01), including, but not limited to, any exterior surfaces, any interface surfaces or areas, or any internal spaces and surfaces, can vary according to variables or any combination of variables such as, but not limited to, the total application time of the "applied agent" (20), total exposure time of the surfaces and areas to the "applied agent" (20), temperature of the "applied agent" (20), temperature of the targeted surfaces and/or areas, relative humidity within the area that the "applied agent" is deployed or administered, flow rate and velocity of the air/gas and "applied agent" (20) that are utilized, the amount or volume of "applied agent" (20) that is generated or produced, the amount of "applied agent" (20) that is applied or deployed to the targeted surfaces or areas, the properties and chemical characteristics of the "applied agent" (20), the amount of positive or negative air/gas pressure that is applied to the endoscope (01) or pressure interface assembly (68) and associated components, and the concentration, number, size, and density of the "applied agent" (20). The variables can vary, without limitation, to achieve the desired or needed results and/or processing time. Other variables may include, but are not limited to the number, shape, diameter, and length of the ducts (08), or size and number of interior spaces inside of the object or endoscope (01), and the selection of the materials used to form the interface (02) and the attributes of the interface material (02).

It is preferred, without limitation, that the aerosol (65) is generated in a separate generation (production) chamber (hereinafter "generation chamber") (15) (FIGS. 1-2) and flowed, blown, or otherwise moved into the sterilization chamber (16) via a blower, fan, or other source of pressurized air/gas (17), where it may then be recirculated back into the generation chamber (15) (FIG. 2) or, to any condenser or filter known to those skilled in the art. The respective chambers are interconnected with piping, tubing, or conduit (18), creating a common atmosphere or potential for a common atmosphere within the closed system. However, if the "applied agent" (20) is created, produced, or generated within the sterilization chamber (16), a blower, fan, or other source of pressurized air/gas, can without limitation, be used to disperse the said agent(s) or substance(s) within the sterilization chamber (16). The sterilization chamber (16) may be constructed so that it is any shape, size, or configuration and can also, without limitation, be any room, chamber, glove box, or connected system of one or more space(s) of any size that may, without limitation, be sealed or enclosed.

The purpose of the "applied agent" (20) such as, but not limited to a gas, vapor, plasma, or aerosol, in the present invention is to coat, interface, interact, envelope, or have contact with, one or more contaminants including but not limited to toxins, bacteria, virus, fungus, spores (both fungal and bacterial), prions or other protein(s), chemicals, compounds, or other structures, within a target area(s) killing bacteria, fungus, spores, or neutralizing toxins or rendering a virus, or protein structure incapable of replication or otherwise interfering with the target's cellular physiology, or destroying or neutralizing the toxin and/or chemicals or chemical structures.

It is preferred in the present invention that the aerosol (65) is generated by one or more aerosol generating ultrasonic transducers (19) located below the surface of an aqueous "applied agent" (20) in a reservoir (21), as shown in FIG. 3. Transducers (19),(22) of any design, frequency, or construction may, without limitation, be used. However, any other means to generate an aerosol, such as but not limited to, high pressure nozzle technology, (65) could potentially be used in the present invention, are not specifically set forth, but are known to those skilled in the art. The reservoir (21) may be made of any suitable material that is unaffected by the chemical action of the "applied agent" (20). One preferred "applied agent" (20) is a mixture of acidic oxidizing compounds including mainly hydrogen peroxide and peroxyacetic acid in an aqueous solution. Suitable materials for the reservoir (21) may include PVC, polypropylene, glass, and stainless steel, but many other suitable materials may be used. The aerosol (65) generated by operation of the transducers (19),(22) forms above the surface of the "applied agent" liquid (20) in the reservoir (21) and is, without limitation, transferred from the basin, reservoir, and/or chamber in which it is created, to the space (16) to be treated by a fan, blower, or other source of pressurized air/gas (17), as will be described in greater detail below.

The output of the transducers (19),(22) is either focused or directed to a point and/or an area near the surface of the "applied agent" (20) to cause a surface disturbance, which results in the formation of an aerosol (65) of the "applied agent" (20). This aerosol (65) is then blown, flowed, or otherwise moved, into the contaminated area, space, or target area, (16) in order to coat, interface, interact, envelope, or have contact with, contaminants including but not limited to toxins, bacteria, virus, fungus, spores (both fungal and bacterial), prions or other proteins, chemicals, compounds, or other structures, within a target area(s) killing the bacteria, fungus, and spores, neutralizing the toxins, or rendering the virus, or protein structure incapable of replication or otherwise interfering with the target's cellular physiology, or destroying or neutralizing the toxin and/or chemicals or chemical structures. The aerosol (65) droplets are of a defined size distribution of less than, but not limited to, 10 microns in diameter, allowing them to behave like a gas due to Brownian movement and diffusion. This enables the droplets to penetrate small cracks and crevices, and apply thin films on surfaces if desired. In addition, the aerosol (65) may effectively reach and disinfect, detoxify, high level disinfect/sterilize, areas of contamination and areas of otherwise limited accessibility. Each transducer (19),(22) used in this apparatus and method is preferably, without limitation, made from lead zirconate-titanate-four (PZT-4), or other suitable piezoelectric materials.

The present invention can include, but is not limited to, the electronic equipment mentioned in U.S. Pat. Nos. 5,878,355 and 6,102,992, which each are incorporated by reference herein in their entirety. A variable frequency oscillator is used to generate a high frequency sine or square wave. A preferred oscillator is a digital function generator/counter capable of producing sine, square, triangle, pulse and ramp waveforms. The unit has an adjustable frequency range from 0.001 hertz to 10 megahertz in seven ranges. It has variable output amplitude from 5 my to 500 Vp-p, variable symmetry/duty cycle from 5% to 95% in the ramp or pulse mode, continuous or externally controlled outputs. A D.C. offset between −10 v to +10 v can be added to any of the output waveforms. A continuous wave power amplifier amplifies the wave generated by the oscillator. The preferred amplifier is a solid-state amplifier with a frequency response from 0.001 hertz to 10 megahertz. It provides up to 2500 watts of linear power with low harmonic and intermodulation distortion, however the number of watts could also be increased in order to provide enough power to drive the desired number of transducers (19),(22).

The amplified signal from the amplifier is used to drive one or a plurality of transducer(s) (19),(22), where each transducer in the present invention is operated at a frequency range between 0.001 to 10.0 megahertz. In addition, each transducer (19),(22) has a resonant frequency between 0.001 and 10.0 megahertz.

Figure 12:
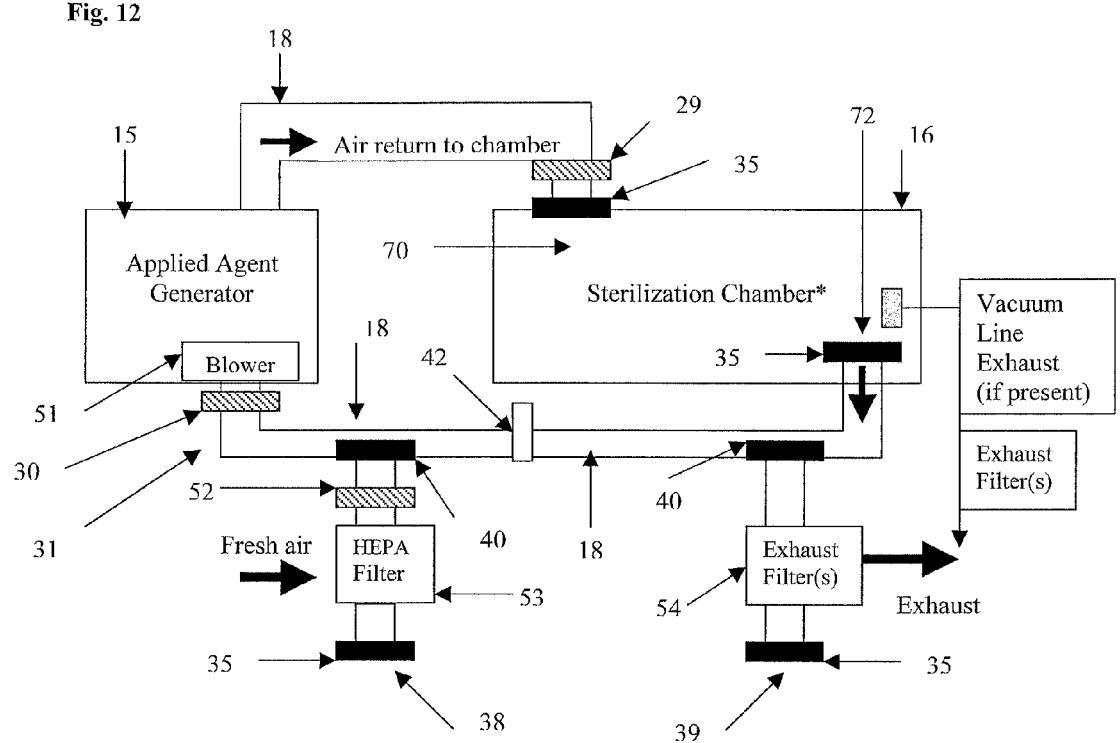

Referring to FIG. 3, there is shown an aerosol generator (15) to which the teachings of the present invention may be applied and used. A reservoir (21) contains a volume of "applied agent" (20), the level of which is controlled by a weir gate (23) operatively associated with a supply pump (24) and line (25) to maintain the level of the "applied agent" (20) at a preferred level above the transducers (19),(22) mounted on the bottom wall of the reservoir. The "applied agent" can vary in temperature when it is applied, however it has been found that the efficiency of aerosol generation is enhanced by heating the liquid "applied agent" (20) to at least 20° F. above ambient, but preferably to at least about 80° F. A heater element (26) mounted in the liquid agent supply sump (27) may be used for this purpose. The aerosolized (65) "applied agent" (20) is delivered to the space to be treated via an exit orifice (28) in one wall of the reservoir to which suitable piping or tubing (not shown) is attached for delivery. A heater element(s) (29) may, without limitation, be attached either to the exit orifice (28) or anywhere between the aerosol generator and the sterilization chamber as taught in prior art. This means for heating is intended to heat the aerosol to various temperatures as it is removed from the aerosol generator or before it reaches the closed space or sterilization chamber (16). A blower, fan, or other source of pressurized air (17) generates the air/gas flow necessary to deliver the aerosol (65), all in a manner well known in the art. As shown in FIG. 12, a return path of suitable piping or tubing (18) may also, without limitation, connect the area or sterilization chamber (16) in which the aerosol (65) is applied back to the air/gas intake of the blower (17) in order to create a closed system or common atmosphere of air/gas in order to prevent positive air/gas pressure from building in the sterilization chamber (16).

A means to radiate heat (30) may also, without limitation, be provided or otherwise operatively coupled to and/or about the outlet(s) of the sterilization chamber (16), or anywhere along the return path of the recirculated air/gas (31) and aerosol before it reenters the aerosol generator (15), in the present invention. This is shown in FIG. 12. The radiated heat provides the added benefit of heating the returning air/gas (31) and aerosol droplets to various temperatures. This may, without limitation, further reduce the diameter of the aerosol droplets (65) so as to lessen the possibility of an impact with droplets (65) within the aerosol generator (15) that would result in the coalescence and/or creation of larger droplets. The heat can vary in its temperature and intensity.

Figure 6:
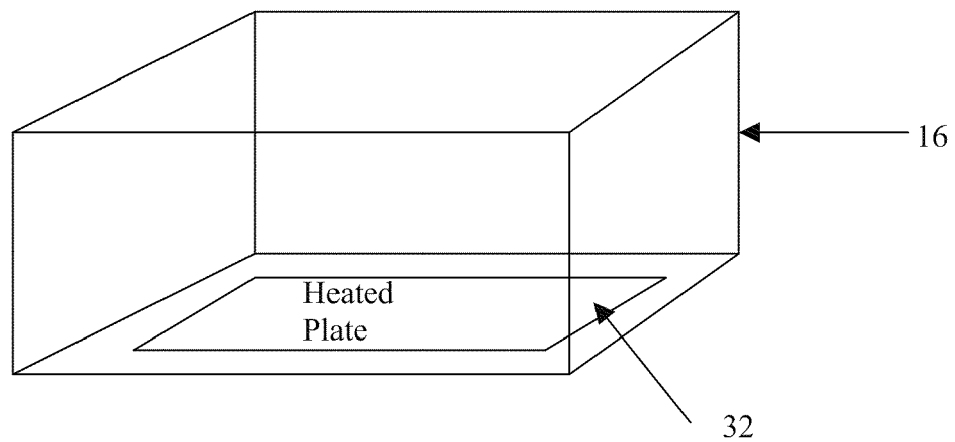

A means to heat the floor and/or bottom area (32), of the sterilization chamber (16) may also, without limitation, be added to the present invention as shown in FIG. 6. A heated plate (32) placed on the floor of the sterilization chamber (16) may also be positioned in this location. The thermal, or convective forces emitted from the heated floor or bottom area (32) of the chamber is intended, without limitation, to both repel any aerosol droplets as they settle, and delay their downward path of travel. An added benefit is that any droplets that do touch or come in close proximity to the heated floor (32) can be turned to vapor or gain additional thermal energy, which can contribute to the efficacy of the process. The means (32) to heat the floor can, without limitation, vary in its temperature and intensity.

Figure 7:
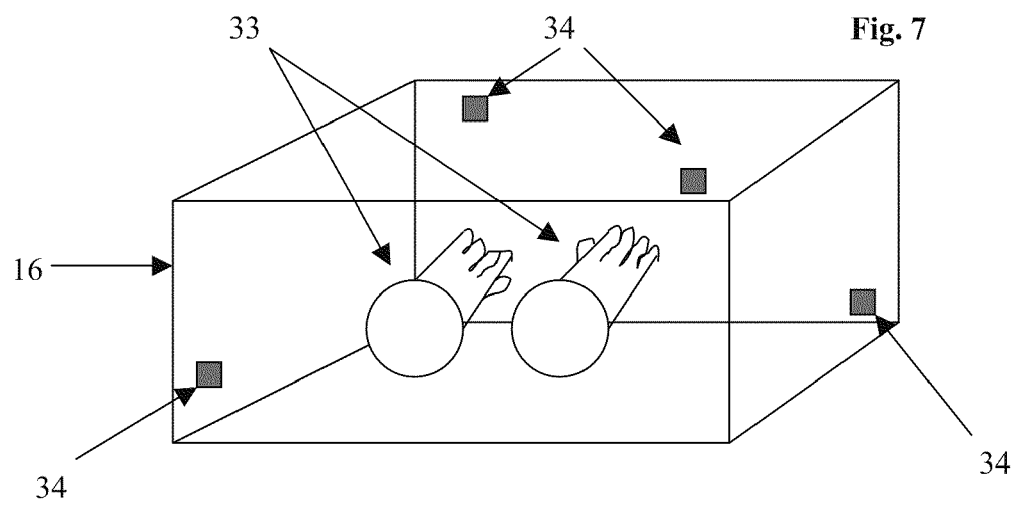

One or more polymer glove(s) or fingers(s) (33) may be incorporated into the system of closed space, and/or the sterilization chamber (16) or an area that can access these spaces, as shown in FIG. 7. They can have a broad similarity in purpose, design, and concept as gloves(s) or finger(s) (33) that are commonly found in laboratory or industrial glove boxes. They can enable an operator to handle the endoscope (01) within the sterilization chamber (16) both before and after the cleaning cycle and related activities have occurred. In addition, the operator can use the glove(s) or finger(s) (33) to handle and place the endoscope (01) into packaging such as but not limited to trays, pouches, bags, or other means to otherwise hold the endoscope (01), and then sealing the packaging so as to keep the packaged endoscope (01) free from contamination or to insure that its properties or characteristics are unaltered. This allows the operator to handle and package the sanitized, detoxified, disinfected, high level disinfected, sterilized, or otherwise cleaned endoscope (01) without having to expose the endoscope (01) to the outside environment and risk contamination.

The endoscope (01) that is placed within the sterilization chamber (16) can be packaged before or after the present invention has completed its operational cycle for the sanitization, detoxification, disinfection, high level disinfection, or sterilization, of the objects, with methods, equipment, and materials which are not specifically set forth, but known to those skilled in the art. This can include packaging methods, equipment, and materials used in industries including but not limited to medical devices, and medical related products.

According to an embodiment, any package (not shown) containing one or more of any objects (not shown) can also be processed in the present invention, for the sanitization, detoxification, disinfection, high level disinfection, or sterilization, of the interior of the package as well as its contents. The package may or may not be connected to the pressure interface assembly (68). It is preferred, without limitation, that the package is constructed of polymer, and it has at least one or more sides or walls that is constructed from materials such as, but not limited to, Tyvek or a similar type of material, glassine, or any type of permeable or semi-permeable material. The packaging materials can be made from any material or combination of materials, and be of any thickness or polarity. It is preferred, without limitation, that the package is constructed in the form of a flexible pouch containing at least one wall that is constructed from a flexible layer of Tyvek whose construction and thickness is commonly used in the medical industry and is known to those skilled in the art. The package may be, without limitation, subjected to any combination and sequence of the following operational parameters such as: (a) Any temperature before exposure to the "applied agent" (b) Any negative atmospheric pressure or vacuum before or during the deployment of any "applied agent" inside of the sterilization chamber (16), (c) any exposure times of the package to the "applied agent", (d) any amount of "applied agent" (e) any temperature during exposure to the "applied agent", (f) any positive atmospheric pressure before, during, or after the deployment of any "applied agent" inside of the sterilization chamber (16), (g) any temperature after exposure to the "applied agent", (h) any temperature and pressure to dry the contents, interior, and exterior of the package, and (i) any drying time.

As also shown in FIG. 7, one or more chemical exposure indicator(s), and/or biological indicator(s) (hereinafter "indicator") (34) can be mounted, held, hung, positioned, or placed, anywhere inside of the closed space or sterilization chamber (16). The position of the indicator(s) (43) can vary both vertically and horizontally with respect to the object(s) in the closed space or sterilization chamber (16). The indicators (34) provide a means for assuring that proper sanitization, detoxification, disinfection, high level disinfection, or sterilization has occurred for the object (01) and/or the closed space or sterilization chamber (16). A detailed description of the construction and operation of suitable chemical exposure indicator(s) and/or biological indicator(s) (34) is not specifically set forth, but is known to those skilled in the art.

Referring again to FIG. 12, one or more means (35) known to those skilled in the art may, without limitation, be operably connected to various components of the present invention to effectively close off, seal, or separate, the closed space or sterilization chamber(s) (16) from the "applied agent" (20) generation chamber(s) (15), and/or the tubes, ducting, channels, tunnels, etc. (18), that connect the "applied agent" (20) generator(s) (15) to the closed space or sterilization chamber(s) (16), at any time including, but not limited to, before or during any washing, cleaning, drying, or other processing activities of the endoscope (01). Referring to FIGS. 4, 5, and 12, a closure device (35) can, without limitation, be any cap or separating device implemented for operably sealing off various portions of the apparatus of the present invention including: a) any air/gas outlet (36) or air/gas inlet (37), or anywhere along the path, for any air/gas or "applied agent" (20) that is flowed through the pressure interface assembly (68); b) any inbound fresh air/gas inlet (38); c) any outbound or exhaust air/gas outlet (39); d) any opening, or inlet or outlet, to/from the sterilization chamber (16), including but not limited to, any air/gas inlet (70) or air/gas outlet (72) to/from the sterilization chamber (16); e) any other tubes, ducting, channels, tunnels, or other parts or components, etc., that would need, or be desired, to have a controlled connection or access, to the pressure interface assembly (68), sterilization chamber (16), or other connected or potentially connected closed space or system of closed space. The closure device (35) can be a door, flap, valve, lid, panel, or other physical means (hereafter called "valve") (35), to contain the chemicals, liquids, vapor, gases, or other substances used in the washing and/or processing activities, within the closed space or sterilization chamber(s). The valve 35 is constructed of any suitable material that is unaffected by the chemical action of the agents or substances used for the washing, cleaning, or processing activities, or the anti-pathogen/toxin/fungal/sporicidal agent(s) or substance(s) that is applied or administered. Referring to FIGS. 12-13, certain valves, covers, doors, flaps or other means known to those skilled in the art (herein called "system valve") (40) may be effectively used during the application or administration of the "applied agent" (20) in the sterilization chamber (16). Each system valve (40) can be actuated, closed, or operated to effectively stop the transfer, flow, or movement of air/gas or "applied agent" (20) through the inbound fresh air/gas inlet (38), the outbound or exhaust air/gas outlet (39), and/or the tubes, ducting, channels, tunnels, etc. (18), that connect the fresh air/gas inlet (38) or exhaust air/gas outlet (39) to the closed system of space or sterilization chamber (16). The various valves (35),(40) in the present invention can be actuated, opened, or operated so that any substances may flow through the valves (35),(40) when desired or needed. In addition, the various valves (35),(40) can be effectively utilized at various times to allow the fresh air/gas from outside of the present invention to flow through, without limitation, the inbound fresh air/gas inlet (38), the air/gas inlet(s) (37) for the air/gas that is flowed through the pressure interface assembly (68), the "applied agent" generator (15), the outbound or exhaust air/gas outlet (39), and/or the tubes, ducting, channels, tunnels, etc. (18), that connect the fresh air/gas inlet (38) or exhaust air/gas outlet (39) to the closed system of space or sterilization chamber (16). Referring to FIG. 12, an additional valve (42) can be utilized to separate the flow of inbound fresh air/gas from the outbound air, gas, or "applied agent" (20) as they are circulated through and from the closed system of space or sterilization chamber (16) and exhausted out of the present invention and into the external environment. The various valves (35),(40),(42) are designed, operationally controlled whether manually or automatically, and operationally sealed in a manner that is not specifically set forth, but known to those skilled in the art. This includes the possible operation, command, and control of the valves (35),(40),(42) via an electronic or electrical means.

Referring to FIGS. 1-2, 4-5, 12-13, 20-23, and FIGS. 26-33, the sanitization, detoxification, disinfection, high level disinfection, or sterilization of both the internal and external surfaces of an endoscope (01) begins with placing it in the closed space or sterilization chamber (16). The endoscope (01) can, without limitation, be washed, cleaned, rinsed, and/or processed after it is placed in the sterilization chamber (16), but prior to the application of the "applied agent" (20). It is preferred, without limitation, that the object or endoscope (01) is washed, cleaned, rinsed, and/or dried and processed before it is placed in the sterilization chamber (16). In either case, the washing, cleaning, rinsing, drying, and/or processing is performed according to methods that are common in the industry in which the object or endoscope (01) is used, and/or according to the recommendations of the object or endoscope's (01) manufacturer. A means for washing, cleaning, rinsing, and/or processing the object(s), such as endoscopes (01), within the sterilization chamber (16), which results in the endoscope (01) being clean, and/or removing contamination such as, but not limited to, blood, saliva, mucous, feces, or tissue, before the application of an "applied agent" (20), may also, without limitation, be added in the present invention and is known to those skilled in the art. After placing the endoscope (01) in the sterilization chamber (16), and the washing, cleaning, and/or processing steps are completed, if they were performed, an "applied agent" (20) such as, but not limited to, any gas, plasma, vapor, or aerosol, is generated and administered, moved, or blown into the closed space or sterilization chamber (16), covering all of the external and possibly the internal surfaces over time. Despite the ability of small droplets and gases to penetrate hard to reach places, it is still difficult and time consuming to disinfect or sterilize the interior surfaces of objects or instruments like endoscopes (01) due to the length and small diameter of features such as, but not limited to, their lumens or ducts (08), and their general construction. However, by using positive or negative air/gas pressure to move the "applied agent" (20) through these hard to reach areas, they can without limitation, be easily and quickly, sanitized, detoxified, disinfected, high level disinfected, or sterilized. The "applied agent" (20) may be pushed or pulled through the endoscope (01) by using the supplied positive or negative air/gas pressure for all endoscope (01)

related applications including, but not limited to, all uses related to the pressure interface assembly (68) as well as all other general endoscope (01) interfaces already known to those skilled in the art. In addition, the "applied agent" (20) may, without limitation, be administered or deployed into the sterilization chamber (16) where it is then pulled into and through the endoscope (01) that is positioned within the sterilization chamber (16).

Figure 14:
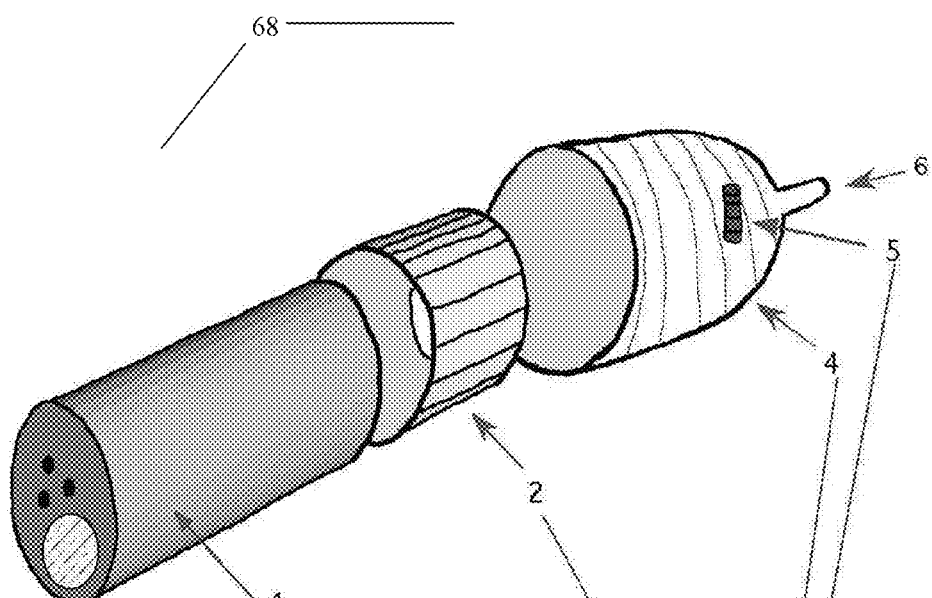
Figure 15:
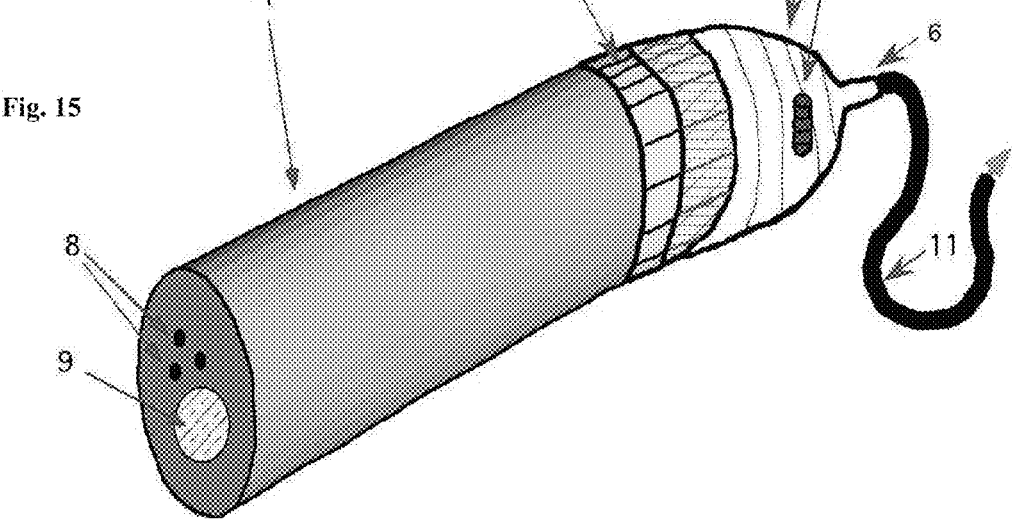

Referring now to FIGS. 14 and 15, one or more open ends or openings of an endoscope (01) are interfaced with one or more pressure interface assembly(s) (68). The open end of an endoscope (01), can include, but is not limited to, the end of the endoscope (01) where the various ducts (08), or other ports end, exit, or are made visible or accessible. This unique and innovative pressure interface assembly (68) has parts including, but not limited to, a coupling (04), and an interface or interface material (02) combination. The coupling (04) can have one or more ports or other means (hereinafter "main port") (06) for attaching one or more tubes, hose, pipes, duct, tunnels, conduit, or other means (herein called "supply tube") (11) that can supply air, gas, liquid, or the "applied agent" (20) under positive or negative pressure, to the various spaces and surfaces of the pressure interface assembly (68) and endoscope (01), including without limitation, their interfacing surfaces and internal spaces and surfaces, under positive or negative pressure. The supply tube (11) can be any size. The main port (06) can, without limitation, connect the space within the pressure interface assembly (68) to the space within the supply tube (11) so that the spaces become connected.

Looking at FIGS. 4 and 5, the supply tube (11) can, without limitation, be effectively connected anywhere to the generation chamber (15) or any other effective area, which is in turn connected to any source of pressurized air/gas or vacuum. The pressure interface assembly (68) allows for any aerosol (65), air/gas, liquid, or "applied agent" (20) to be driven, pushed, or pulled through places such as, but not limited to, both the internal space and/or ducts (08), of the endoscope (01), as well as through the interface material (02) and/or interface location, for purposes including, but not limited to, rinsing the endoscope (01), drying the endoscope (01), or the sanitization, detoxification, disinfection, high level disinfection, or sterilization of these areas and their respective surfaces. It is preferred, without limitation, that the pressure interface assembly (68) is utilized inside of the sterilization chamber (16), but it could also be used outside of the sterilization chamber (16) in applications not specifically set forth but are known to those skilled in the art.

The supply of a positive or negative air/gas pressure to the pressure interface assembly (68) may originate from any vacuum pump, air/gas pump, pressurized air source, fan, or blower (44),(17). The air/gas pressure can vary depending on the situation and particular application and can serve several functions. First, the positive and/or negative air/gas pressure can, without limitation, be applied to the pressure interface assembly (68) at the beginning and/or end of the sanitization, detoxification, disinfection, high-level disinfection, or sterilization cycle, in order to move air/gas or dry and/or heated air through the interior space of the endoscope (01). This will remove any moisture if it is still present in these areas.

Referring now to FIGS. 12 and 13, one or more heating element(s) (29),(52) placed in the air stream before or after the pressure interface assembly (68) can provide the heated air (referenced Rosdahl et al. pg 3 Col. 123-127). It is preferred, without limitation, that air from outside of the sterilization chamber (16) that is pulled, drawn, pushed, or otherwise moved into the sterilization chamber (16) and/or the endoscope (01) be first filtered before its entry into the sterilization chamber (16) and/or endoscope with one or more high efficiency filter (53) such as, but not limited to, a HEPA filter or other filter that is known to those skilled in the art or is acceptable in the industry in which it is used. The air/gas stream may also, without limitation, be filtered by one or more filters (54) before it exits from the sterilization chamber (16); and the filter is known to those skilled in the art or its use is acceptable in the industry in which it is used. The air can, without limitation, be heated within the sterilization chamber (16) and/or before its entry into the sterilization chamber (16) from areas including, but not limited to, the outside atmosphere, or the atmosphere that surrounds the outside of the sterilization chamber (16), in order to help dry the endoscope (01) at the desired time or stage during processing.

Also, the positive air/gas pressure or negative air/gas pressure is intended to move the "applied agent" (20) through the interior space of the endoscope (01). It is preferred, without limitation, that, as shown in FIG. 4, if a negative air/gas pressure is supplied to the coupling (04) that is interfaced or attached to the endoscope (01), a pressure differential is established. This results in the flow of air/gas and the "applied agent" (20) from areas such as, but not limited to, the sterilization chamber (16), through "both" the interface material (02) and internal space within the endoscope (01), and into the coupling (04). Once in the coupling (04), the air/gas and the "applied agent" (20) flows into the attached pipes, tubes, conduits, etc. (11),(118), where it is eventually vented back into the sterilization chamber (16), or through a filter (54) and into the outside environment.

The "applied agent" (20) can, without limitation, flow into the coupling (04) under positive air/gas pressure, as shown in FIG. 5. It is preferred, without limitation, that in this situation, the air/gas and "applied agent" (20) is pulled from the sterilization chamber (16), or chamber where the "applied agent" is generated (15), and flowed into the coupling (04) via the attached pipes, tubes, conduits, etc. (18),(11). It is then flowed "both" out of the interface material (02) and through the internal space within the endoscope (01), and into the sterilization chamber (16). The "applied agent" (20) in this case, can also be separately delivered into the sterilization chamber (16), if it is generated in a chamber (15) separated from the sterilization chamber (16).

Without limitation, the apparatuses and methods can be used or take place in any type of rigid, semi-rigid, flexible container, or package (herein called "container"), and the container can function as the sterilization chamber (16). The container (16) can, without limitation, have the pressure interface assembly (68) or coupling (04) integrated into its design or construction. The container (16) can, without limitation, be designed so that it can be sealed and function as effective packaging or medical quality packaging after completion of the processing steps in a manner that meets or exceeds industry and regulatory standards.

Referring to FIG. 4-5, 14-16, the coupling (04) can be constructed from various materials such as, but not limited to, stainless steel, glass, polymer, polyolefin, cellulose, or even natural or manufactured fibers that are either coated or uncoated. The coupling (04) can, without limitation, be constructed from one or more polymers that meets or exceeds industry and regulatory standards. It is preferred without limitation, that the coupling (04) is constructed from one or more polymers that can include, but is not limited to PVC, polycarbonate, polypropylene, and HDPE. The coupling (04) surfaces can, without limitation, be electrically or electrostatically charged in order to attract the "applied agent" (20). It is preferred, without limitation, that the materials used to construct the coupling (04) may be rigid, semi-rigid, or flexible. A flexible polymer or tube roll is one example of a flexible material that could be used. The pressure interface assembly (68) can be designed and constructed for single or multiple uses. It is preferred, without limitation, that the coupling (04) is designed so that one end is able to fit over an end of an endoscope (01), and the other end of the coupling (04) is substantially closed. The coupling (04) can, without limitation, be designed so that one end is able to fit over an end of an endoscope (01), and the other end of the coupling (04) is designed to interface or connect with a supply tube (11) or other means to connect the coupling (04) to a source of negative or positive air/gas pressure in a suitable manner. For example, one end of the coupling (04) can be, without limitation, open and its exterior surface can have a hose barb, or a portion of its exterior surface can be molded into a barb of sufficient size to securely interface/articulate it with a supply tube (11). The end of the coupling (04) that is designed to fit over an end of an endoscope (01), can have an opening of various sizes and shapes. This opening can control the negative or positive air/gas flow in or out of the coupling (04).

One or more main ports (06) or means to connect the coupling (04) with a supply of positive and/or negative air/gas pressure that is used to drive, push, or pull the "applied agent" (20) through both the ducts (08) of the endoscope and the interface material (02), can be located on the closed end or "air/gas pressure interfacing end" of the coupling (04). This main port(s) (06) may be connected to a positive or negative air/gas pressure supply tube (11) in order to create a positive air/gas or negative air/gas pressure within the coupling (04). In the context of the present invention, "tube" or "tubing" includes pipes, ducts, conduits, tunnels, and the like.

One or more chemical contact or biological indicators (hereinafter "indicator(s)") (05) of any size type or construction may be mounted, held, hung, positioned, or placed, anywhere inside of the pressure interface assembly (68). The pressure interface assembly (68) is designed for the addition as well as possible removal of these accessories. The indicator (05) provides a means for communicating or assuring that proper sanitization, detoxification, disinfection, high level disinfection, or sterilization has occurred within the endoscope and/or the pressure interface assembly. A detailed description of the indicator (05) is not specifically set forth, because the details are well known to those skilled in the art.

The internal dimensions of the coupling (04) help provide for an interface/articulation between the endoscope (01), the interface or interface material (02) (if it is used), and the coupling (04), that permits the creation of at least a minimum working positive or negative air/gas pressure inside of the coupling (04) and endoscope (01), but still allows "applied agent" (20) to penetrate and sanitize, detoxify, disinfect, high level disinfect, or sterilize the areas and surfaces that interface/articulate or are between the endoscope (01) and the interface material (02) (if it is used), or the coupling (04). In certain circumstances, the inner diameter of the coupling (04) in addition to its thickness can contribute to the performance of the interface (02). This can include but is not limited to, coupling (04) designs where the part of the coupling (04) that interfaces with the endoscope (01) is constructed from materials that are flexible and may or may not have elastic properties. More specifically, the inside dimensions and thickness of the coupling (04) can change in order to accommodate various variables, including, but not limited to, pressures, temperatures, sizing, shape, fit, interface integrity, interface efficiency, thickness of the interface, as well as other variables to achieve efficacy with the process. The coupling (04) may not even touch the exterior or internal surfaces of the endoscope (01).

Referring to FIGS. 14-19, the coupling (04) is preferably used in combination with an interface material (02) to interface/articulate with the external circumference or external surfaces of the endoscope (01). In addition, it is preferred that the interface material (02) is positioned between the coupling (04) and the endoscope (01). The interface material (02) can be, without limitation, porous, and/or permeable, and is constructed from materials that can provide effective performance and the desired level of efficacy for the process. The interface material (02) can be, without limitation, constructed of one or more layers of material. The interface material (02) may also have absorbent characteristics to improve its efficacy and performance. The interface material (02) is intended, without limitation, in the present invention to allow the air/gas and the "applied agent" (20) to move or flow through the interface layer at a controlled, but effectual rate, so that at least a minimum working positive or negative air/gas pressure is created or established inside of the coupling (04) and endoscope (01). This minimum working positive or negative air/gas pressure that is created or established inside of the coupling (04) and endoscope (01), moves or otherwise results in the movement or flow of the "applied agent" (20) through places such as, but not limited to, the interior space, or ducts (08), of the endoscope (01) and results in the sanitization, detoxification, disinfection, high level disinfection, or sterilization of these surfaces and areas. The minimum working positive or negative air/gas pressure that is created or established inside of the coupling (04) and endoscope (01), moves or otherwise results in the movement or flow of the "applied agent" (20) through the interface material (02) and areas of interface/articulation between the interface material (02) and endoscope (01), and results in the areas and surfaces under the interface material (02) to be exposed to, and acted upon, by the "applied agent" (20) in order to achieve the desired level of sanitization, detoxification, disinfection, high level disinfection, or sterilization. The interface material (02) can include, but is not limited to cloth, gauze, manufactured fibers, synthetic fibers, natural fibers or materials, cellulose, polymer, polyolefin, glass, metal, ceramic, carbon, combinations of these materials, or other materials know in the art. The interface material (02) can be coated with chemicals, materials, or substances including, but not limited to, polymer(s), polyolefin, wax, lipid, oil, enamel, paint, carbon, metal, combinations of these materials, or other materials known in the art. The interface material (02) as well as the coupling (04) surfaces can be electrically or electrostatically charged or uncharged in order to attract the "applied agent". The electrostatic potential or polarity of the various materials as well as the "applied agent" (20) can, without limitation, vary. Materials for the interface material (02), which are developed in the future, may be utilized to improve the efficacy of the design or its application to certain objects, endoscopes (01), or devices. The interface material (02) and its effectiveness can vary with variables including but not limited to, its size, width, surface area, shape, fit, thickness, density, hardness, elasticity, flow rate, porosity, permeability, evenness of air/gas flow, mechanical properties, physical properties, and other variables known to those skilled in the art. However, the effectiveness and efficacy of each interface material (02) can increase with attributes such as, but not limited to, the uniformity of these variables throughout the interface that is used. The interface material (02), coupling (04) and endoscope (01), can be planned, manufactured, or formed, to assure the proper placement, fit, or function of these components. The shape or physical parameters may include, but is not limited to, closing or tapering the ends of the interface material (02) to various amounts or increments, the presence of ribbings, pegs, grooves, studs, or clips, or other means known to those skilled in the art, that are indented or protrude from components including, but not limited to, the interface material (02), coupling (04) and/or endoscope (01), so that the interface material (02) can interlock or have a controlled or guided articulation/interface with the coupling (04) and/or object or endoscope (01). The interface material (02) may be connected to the coupling (04), or endoscope (01) in various ways that include, but is not limited to, welding, forming, molding, bonding, adhering, gluing, laminating, or cementing. The performance of the interface material (02) or the pressure interface assembly (68) may, without limitation, be improved by welding, forming, molding, bonding, adhering, gluing, laminating, or cementing, one or more layers of material with attributes such as, but not limited to any, width, surface area, shape, thickness, density, hardness, elasticity, flow rate, porosity, permeability, evenness of air/gas flow, mechanical properties, or physical properties, between the interface material (02) and the coupling (04), or between the endoscope (01) and the interface material (02). It is preferred, without limitation, that the material is pliable. The coupling (04) can also be constructed from, or otherwise be, the interface material (02) or interface material (02) and function as the interface (02), which negates the use of a separate interface material (02). This represents the pressure interface assembly (68) in its simplest form. In this case, the coupling (04) is designed and constructed so that it incorporates the purpose, performance, traits, attributes, and characteristics of both the interface material (02) and the coupling (04). Everything pertaining and related to the interface material (02), coupling (04), and exertion of pressure on these materials, in the present invention also pertains to this particular design/construction.

The performance of the interface material (02) is also impacted by the application, existence, and/or control of a pseudo constant or constant, and effectively distributed, pressure exerted on the interface material (02) (herein called "exerted pressure") as it contacts the endoscope (01). This exerted pressure provides, without limitation, an effective distribution of flow of the "applied agent" (20) through the interface material (02) and areas of interface/articulation between the interface material (02) and endoscope (01), and results in the areas and surfaces under the interface material (02) and surfaces of the endoscope (01) that interface/articulate with the material of the interface material (02), to be exposed to and acted upon, by the "applied agent" (20), in order to achieve the desired level of sanitization, detoxification, disinfection, high level disinfection, or sterilization. The application, existence, and/or control of a constant or relatively constant, and effectively distributed, pressure exerted on the interface material (02) as it contacts the endoscope (01), can also, without limitation, be sufficient to hold the endoscope (01) if it is suspended in the sterilization chamber (16) via the pressure interface assembly (68). The weight of the endoscope (01) and/or pressure interface assembly (68) can provide at least the minimum pressure/force needed to form and/or establish a usable and efficacious interface/articulation, and this can, without limitation, be accomplished in a manner known in the art.

It is preferred in the present invention that the exerted pressure is not only effective, but it is evenly distributed. In addition, this exerted pressure can also affect the balance of flow of the "applied agent" (20) through the interface material (02), as well as the interior space or ducts (08) of the endoscope (01). It is preferred in the present invention that the flow of air/gas and "applied agent" (20) through the interface material (02), as well as the interior space or ducts (08) of the endoscope (01), is adjusted so that a desired level of sanitization, detoxification, disinfection, high level disinfection, or sterilization can be achieved. The exerted pressure can vary due to variables related to the interface material (02), including but not limited to its, size, width, surface area, shape, fit, thickness, density, hardness, elasticity, mechanical properties, physical properties, and other variables known to those skilled in the art. The exerted pressure can also vary to control variables associated with the air/gas and "applied agent" (20), including but not limited to, flow rate, air/gas flow and pressure, permeability, and evenness of flow through the interface material (02), and balance of flow through both the interface material (02) and the interior space or ducts (08) of the endoscope (01). The exerted pressure can vary depending on the amount of force that is exerted on the interface material (02), and the amount of surface area of the interface material (02) that receives that force (force per unit area).

Figure 16:
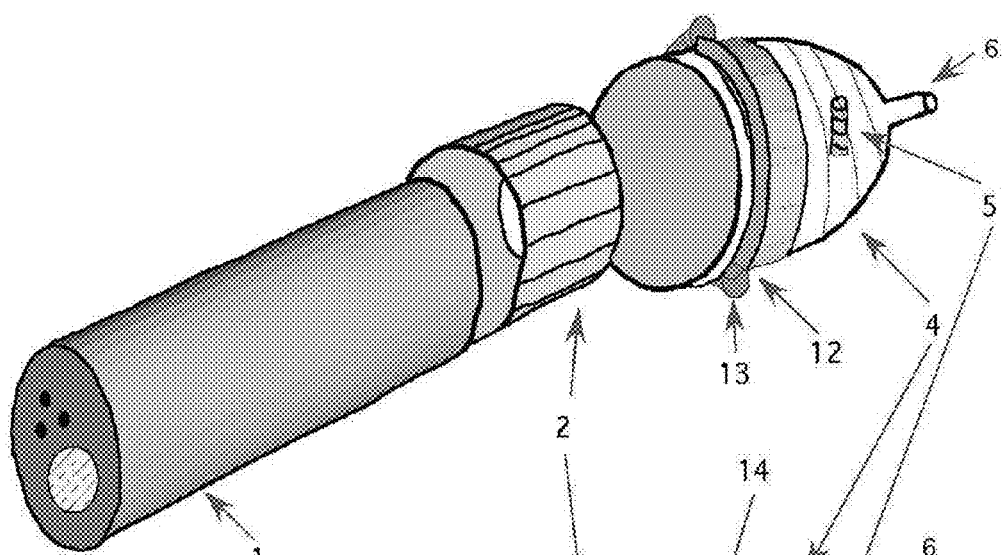
Figure 17:
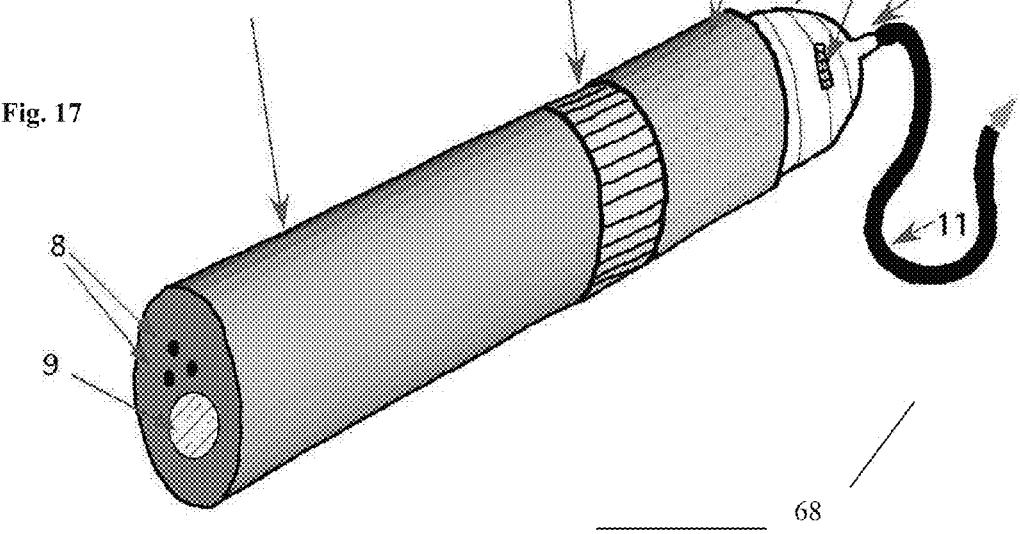

The effective pressure that is exerted on the interface material (02) can result from the articulation/interface of the coupling (04), interface material (02), and endoscope (01). This can be accomplished by ways including, but not limited to, adjusting the designs, dimensions, and properties, of the coupling (04), interface material (02), and endoscope (01), to create a loose or tight fit and/or a weak or strong friction fit, with the interface material (02) and the endoscope (01). It can be accomplished through the use of additional means to exert pressure around the coupling (04), interface material (02) and endoscope (01) in order to create an effective articulation/interface, and includes but is not limited to positioning a clamp over or around the coupling (04) and applying pressure to the coupling (04), interface material (02), and endoscope (01), which creates an effective articulation/interface. It can also be accomplished by utilizing a coupling (04) where at least the part or area of the coupling (04) that interfaces/articulates with the endoscope (01) is constructed from material that is flexible, and may or may not have elastic properties, and one or more parts or areas of this coupling (04) that interface/articulate with the endoscope (01) have dimensions, an inner diameter or inner dimensions, and width, so that an effective pressure is exerted on the interface material (02) when the coupling (04) is interfaced/articulated with the endoscope (01). As shown in FIGS. 16 and 17, this can include, but is not limited to, a coupling (04) that is completely or partially constructed from a flexible material (12), (14) and/or one or more flexible rings (13) that are either built into the flexible material (12),(14) or positioned outside and around the coupling's flexible wall material (12),(14). For example, and without limitation, an effective or sufficient interface material (02) can be provided by, without limitation, one or more rings (13) that fit over, and are utilized to apply an effective or sufficient force or pressure to, the coupling (04), interface material (02), and endoscope (01). Various attributes including, but not limited to, the dimensions, thickness, interior dimensions or interior diameter, and width, of the rings (13) have tolerances so that the rings (13) exert effective pressure on the coupling (04), interface material (02), and endoscope (01), when the pressure interface assembly (68) interfaces/articulates with the endoscope (01). This can also include, but is not limited to, a coupling (04) that is constructed from a rigid or semi-rigid polymer and one or more rings (13) are built into the coupling's (04) interior wall where they can interface/articulate with the interface material (02), and endoscope (01). Various attributes including, but not limited to, the dimensions, thickness, interior dimensions or interior diameter, and width, of the rings (13) have tolerances so that the rings (13) exert effective pressure on the coupling (04), interface material (02), and endoscope (01), when the pressure interface assembly (68) interfaces/articulates with the endoscope (01).

According to an embodiment, one or more encircling geometric shapes or rings (not shown) can also be added to the exterior of an endoscope (01) and/or to the endoscope (01) interfacing/articulating surfaces of the pressure interface assembly (68). Without limitation, these encircling geometric shapes or rings can protrude outward or inward, and can be created without limitation by cutting, carving, engraving, molding, thermoforming, or laminating, gluing, cementing, adhering, or otherwise being attached, to the pressure interface assembly (68). Without limitation, the encircling geometric shapes or rings can also be partially or fully constructed from and have the same chemical, physical, and mechanical properties of the materials that can be used to construct the endoscope (01), the coupling (04), and/or one or more of the interface materials (02) that articulates between the pressure interface assembly (68) and the endoscope (01), and can also be made from a combination of these different materials.

These shapes or rings can, without limitation, interact with each other, the interface material (02), the endoscope (01), the coupling (04), and/or the pressure interface assembly (68). They can be connected to the interface material (02) in various ways that include, but are not limited to, welding, forming, molding, bonding, adhering, gluing, laminating, or cementing, and/or they can also function as the interface material (02). The encircling geometric shapes or rings can also interact or interlock with each other to securely engage the assembly (68) with the endoscope (01). For example, without limitation, the rings can slide past or over each other and into a static position, or be turned within a grove and lock into a static position. The interaction of these encircling geometric shapes or rings can create at least the minimum pressure/force needed to form and/or establish an efficacious and usable interface material (02) and interface/articulation. The interaction of these encircling geometric shapes or rings can also be used to bear the weight of the endoscope (01) if it is suspended in the sterilization chamber (16) via the pressure interface assembly (68). The weight of the endoscope (01) and/or pressure interface assembly (68), in this instance can also provide at least the minimum pressure/force needed to form and/or establish a usable and efficacious interface material (02).

Figure 18:
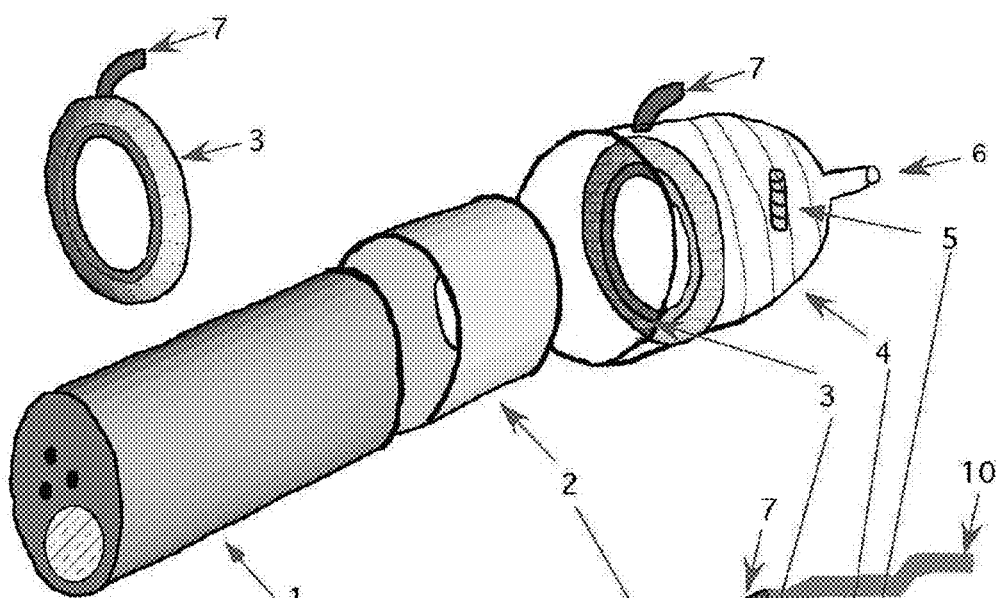
Figure 19:
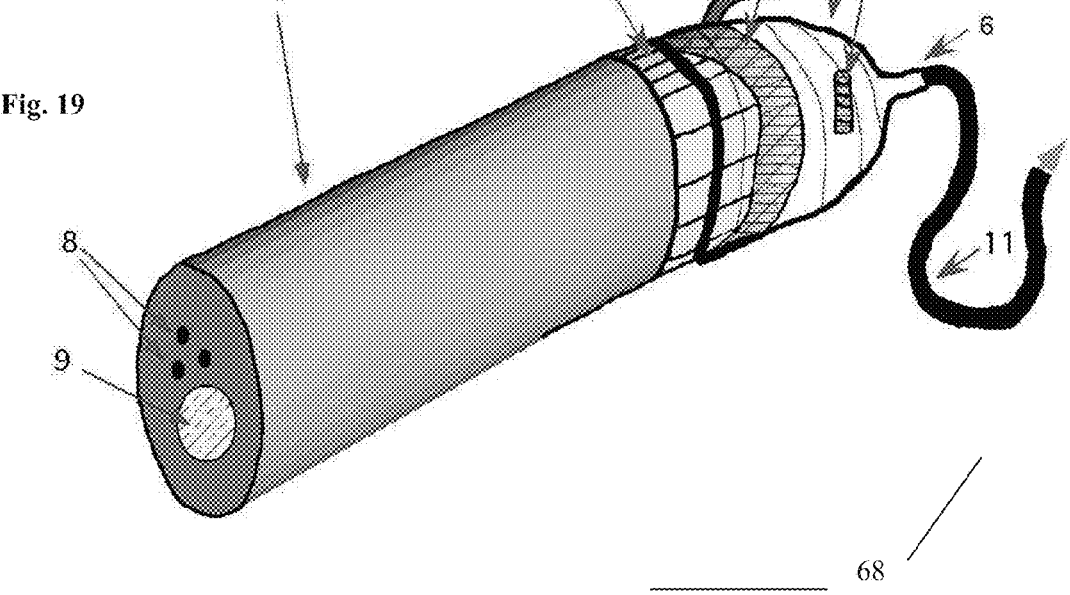
Figure 20:
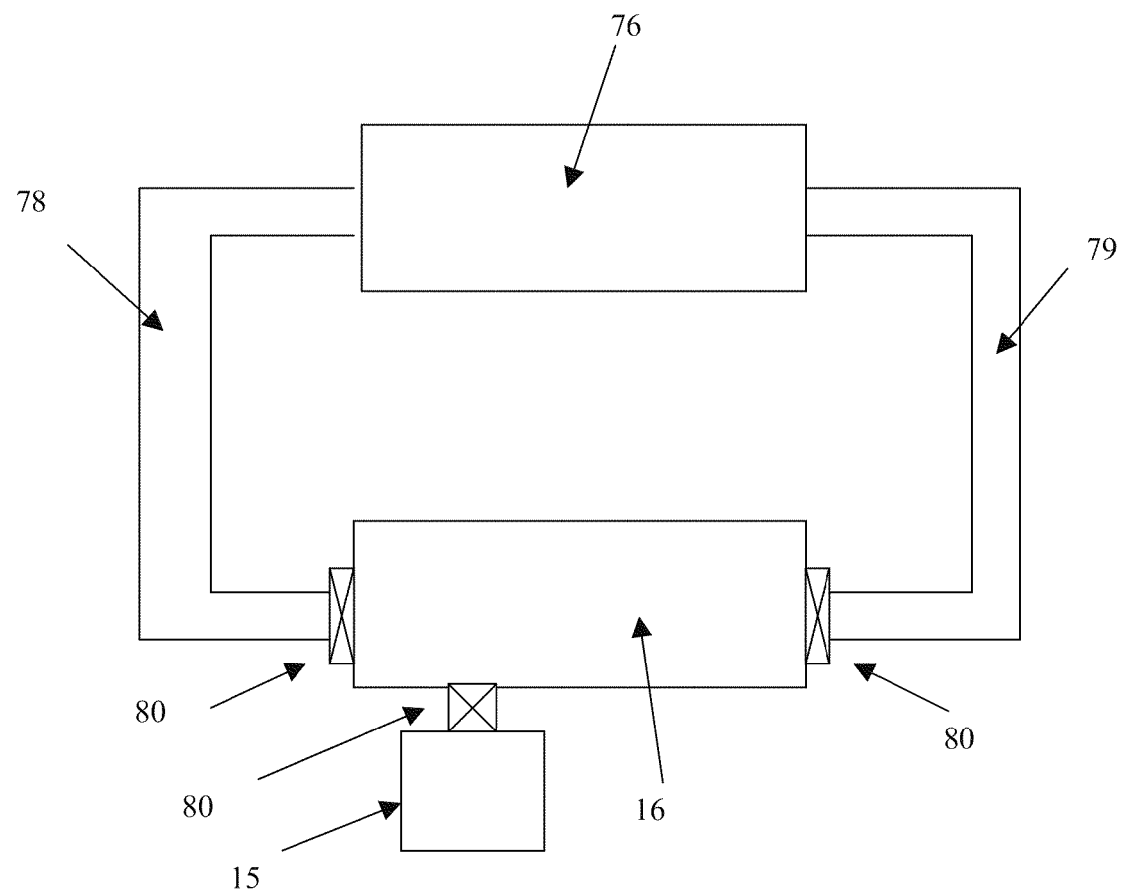
Figure 21:
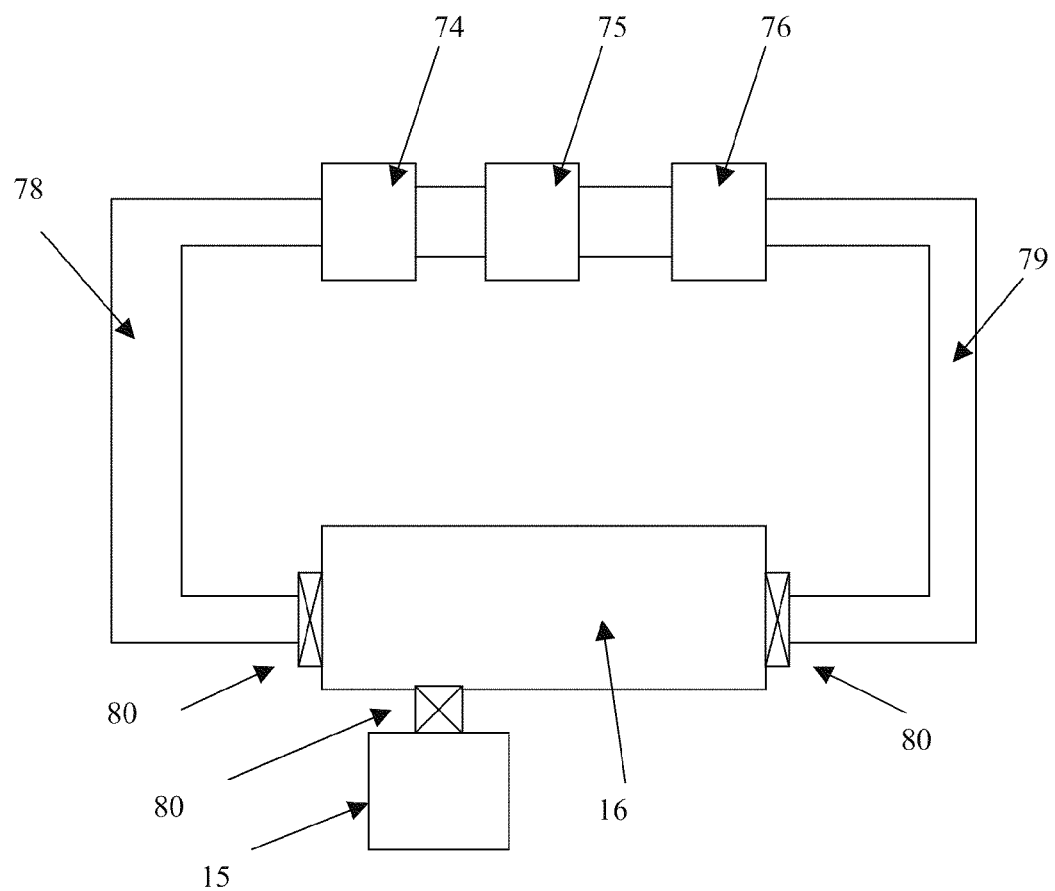
Figure 22:
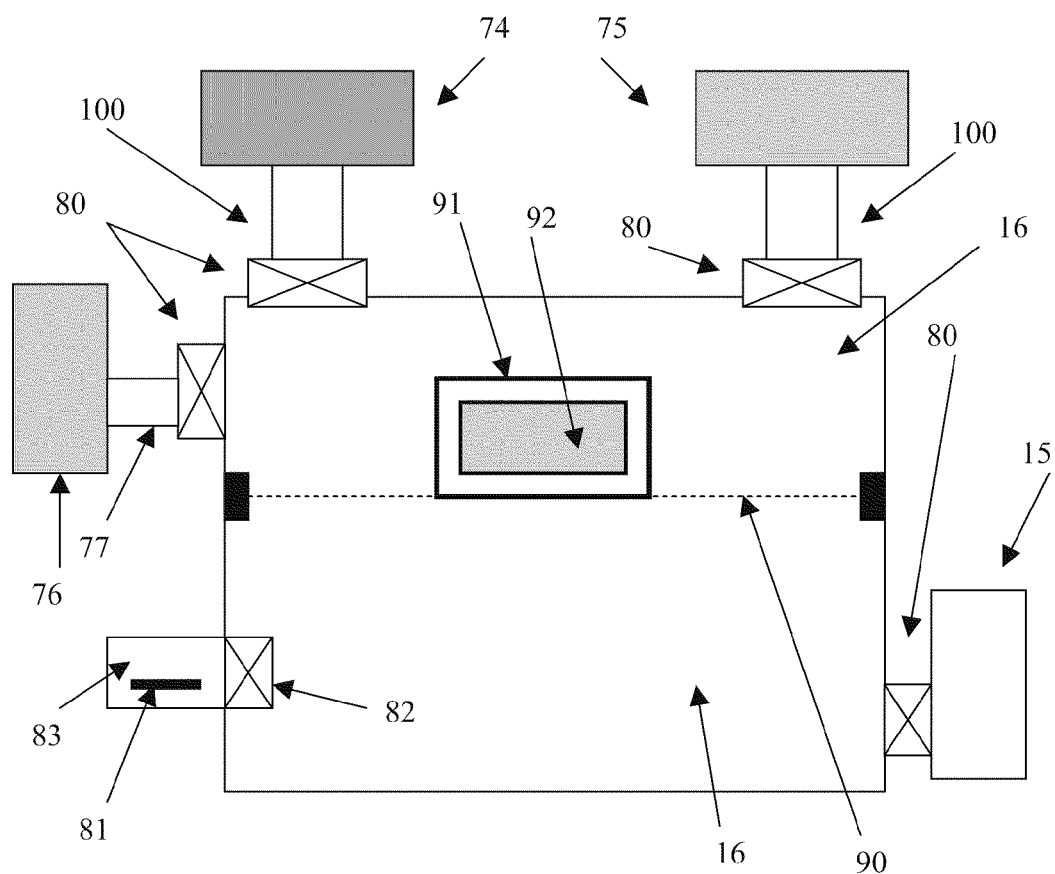
Figure 23:
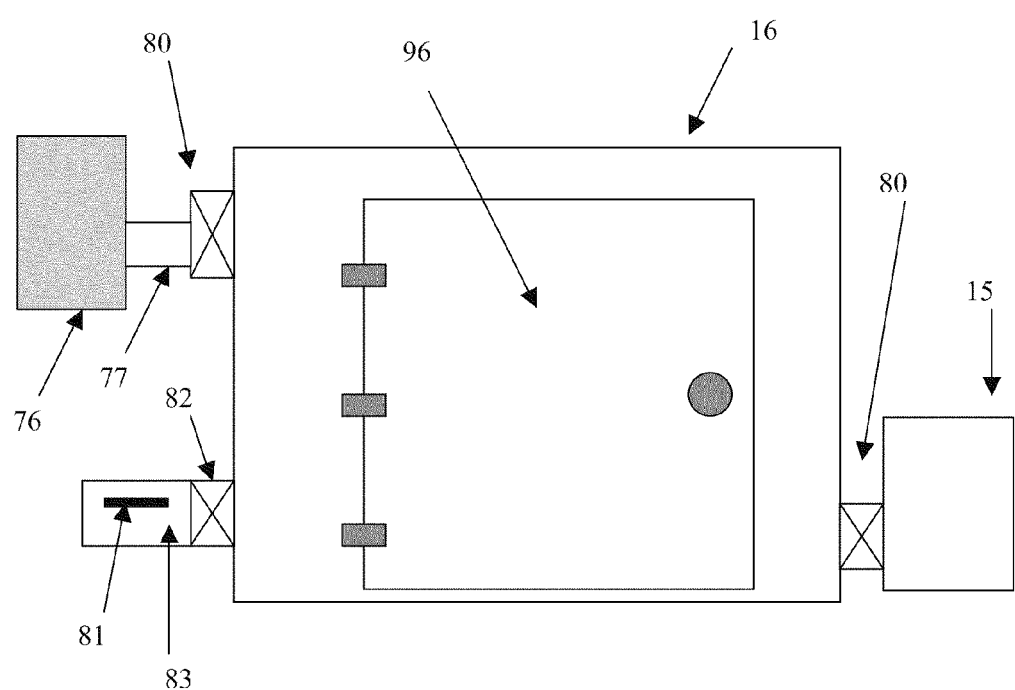

Referring to FIGS. 18-19, an inflatable pillow, balloon, bladder, reservoir, or other inflatable or expandable means or material (hereinafter "balloon") (03), can be used to exert an effective pressure on the interface material (02), as well as on the coupling (04). Varying the amount of exerted pressure inside of the balloon (03) can control the pressure that is exerted. The balloon (03) can be utilized in ways including, but not limited to, inserting or positioning the balloon (03) completely, or at varying positions or amounts, around the interface material (02), on the side of the interface material (02) that is furthest away from the endoscope (01) and closest to the interior wall of the coupling (04), and inflating the balloon (03) after the pressure interface assembly (68) is effectively positioned or has interfaced/articulated with the endoscope (01). The balloon (03) can also be positioned and effectively used inside of the coupling (04) wall material or on the exterior surfaces of the coupling (04). The size, width, thickness, inflation pressure, material of construction, and design of the balloon (03) can be influenced by many factors including, but not limited to the negative and positive pressure or air/gas pressure that can be exerted within the coupling (04), the temperatures of the "applied agent" (20), the amount of pressure that is needed inside of the balloon (03) in order to apply an effective pressure on the interface material (02), and the type of chemical interaction between substances such as, but not limited to, the "applied agent" (20), and various materials of construction. The balloon (03) may assume many different shapes including, but not limited to, a toroidal shape. The balloon (03) can also be constructed from, or have its outermost layer constructed from the interface material (02), and the balloon (03) can function as the interface material (02). The balloon (03) can have a port and/or valve (herein called "balloon port") (07) to connect with a source of pressurized fluid, and is inflated and deflated by way of a means that is known to those skilled in the art. The source of pressure can include, but is not limited to, the supply of air, gas, liquid, or foam under positive pressure. An effective pressure can also be created as the result of a chemical reaction inside of the balloon (03).

Parameters such as, but not limited to: a) the exerted pressure on the interface material (02); b) the positioning of the coupling (04) on or to the interface material (02); c) the surface area of the coupling (04) that interfaces/articulates with the interface material (02) or endoscope (01); d) any physical, chemical, or mechanical interactions between any components of the pressure interface assembly (68); d) the size, width, surface area, shape, fit, thickness, density, hardness, elasticity, flow rate, porosity, permeability, mechanical properties, physical properties, and other variables known to those skilled in the art, relative to various components of the pressure interface assembly (68) such as, but not limited to the interface material (02), the coupling (04), and endoscope (01); e) evenness of air/gas and "applied agent" flow (20); can all, without limitation, be varied and may help control the air/gas pressure differential between the outside and inside of the coupling (04). These parameters may also vary, without limitation, to help control the air/gas pressure differential between the endoscope's (01) ducts (08) and the outside and inside of the coupling (04). This in turn controls the balance of the "applied agent" (20) flow through the interface material (02) and any interfaced/articulated areas verses the interior space or ducts (08) of the endoscope (01). These variables are optimized for each endoscope (01) configuration based on the outside diameter of the endoscope (01), and the number, diameter, area, and length of the interior spaces or ducts (08), of the endoscope (01).

Referring to FIG. 4, for applications involving the movement of an "applied agent" (20), in form including but not limited to any gas, plasma, vapor, and/or aerosol, through the endoscope (01) with negative air/gas pressure (vacuum), the endoscope (01) is placed within the closed space or sterilization chamber (16), or other area within the closed system, and the pressure interface assembly (68) is interfaced with an end of the endoscope (01). The "applied agent" (20) is then generated and/or administered or applied, filling the closed space or sterilization chamber (16). The "applied agent" (20) that is in the sterilization chamber (16) is then pulled through one end of the endoscope (01), through its interior space or ducts (08) via a negative air/gas pressure (vacuum) that is created in the coupling (04). The negative air/gas pressure can vary. The "applied agent" (20) is then, without limitation, pulled through any supply tube (11) and is then, without limitation, vented into an area (36) either back into the sterilization chamber (16), or other area within the closed system. The vacuum is generated by one or more, without limitation, air/gas pump, vacuum pump, venturi apparatus, blower, fan, or other means (44),(17) that can create a negative air/gas pressure (vacuum) within the pressure interface assembly (68). The "applied agent" (20) that is pulled with vacuum can also vent into the outside environment after being filtered, if filtering is necessary. If the "applied agent" (20) is vented into the outside environment, a means to provide equalization in air/gas pressure between the closed system and the outside environment is provided and the movement of the air/gas is filtered. The resulting process is the sanitization, detoxification, disinfection, high level disinfection, or sterilization, of both the exterior of the endoscope (01) and its interior space or ducts (08).

Referring to FIG. 5, alternatively, for applications involving the movement of an "applied agent" (20) in the form including but not limited to any gas, plasma, vapor, and/or aerosol, through the object or endoscope (01) with positive air/gas pressure, the endoscope (01) is placed within the closed space or sterilization chamber (16), or other area within the closed system, and the pressure interface assembly (68) is interfaced with an end of the object or endoscope (01). The "applied agent" (20) is then generated and/or administered or applied, filling the closed space or sterilization chamber (16). The "applied agent" (20) that is in the closed space or chamber (16), or other area within the closed system, is then, without limitation, pulled through one end (37) of a tube (18) and forced out the other end of the same tube or any other connected tube(s), into the supply tube (11), under positive air/gas pressure, and then into the coupling (04) that interfaces/articulates with the endoscope (01), and then into and through the interior space or ducts (08) of the endoscope (01) where it is then vented back into the closed space, sterilization chamber (16), or other area within the closed system. The positive air/gas pressure is generated by one or more air/gas pump, vacuum pump, blower, fan, or other means (44),(17) that can create a positive air/gas pressure within the pressure interface assembly (68). The positive air/gas pressure can vary. The "applied agent" (20) in this case can also be pulled from a source that is separate from the sterilization chamber (16). The result of the whole process is the sanitization, detoxification, disinfection, high level disinfection, or sterilization, of both the exterior of the endoscope and its interior space, lumen(s), and/or channels.

The positive or negative air/gas pressure can also be supplied to the pressure interface assembly (68) and the interfaced/coupled or articulated object or endoscope (01), by one or more air/gas pump, vacuum pump, blower, fan, or other means (44),(17), at different times during the sanitization, detoxification, disinfection, high level disinfection, or sterilization cycle. For example, this can be performed, without limitation, either before or after the "applied agent" (20) is generated and/or administered or applied. The purpose is to move, without limitation, fresh filtered or non-filtered air/gas and/or dry air/gas through the interior space or ducts (08) of the endoscope (01), which removes any moisture, liquid, and/or "applied agent" (20) that is present, or cause the moisture, liquid, agent, "applied agent" (20) or substance that is present to be removed or evaporated.

One challenge with the application of an "applied agent" (20) by aerosol or other means, is that of obtaining full coverage on all surfaces of the endoscope (01) or the targeted space, areas, or surfaces. This is especially true when two surfaces touch each other, which prevents the contacted surfaces from being exposed to the "applied agent" (20). This causes a shadowing effect. Of course, this challenge does not apply to the use of ethylene oxide gas (EtO) with polymeric materials because EtO is able to penetrate that material and any shadowed surfaces over time.

Figure 30:
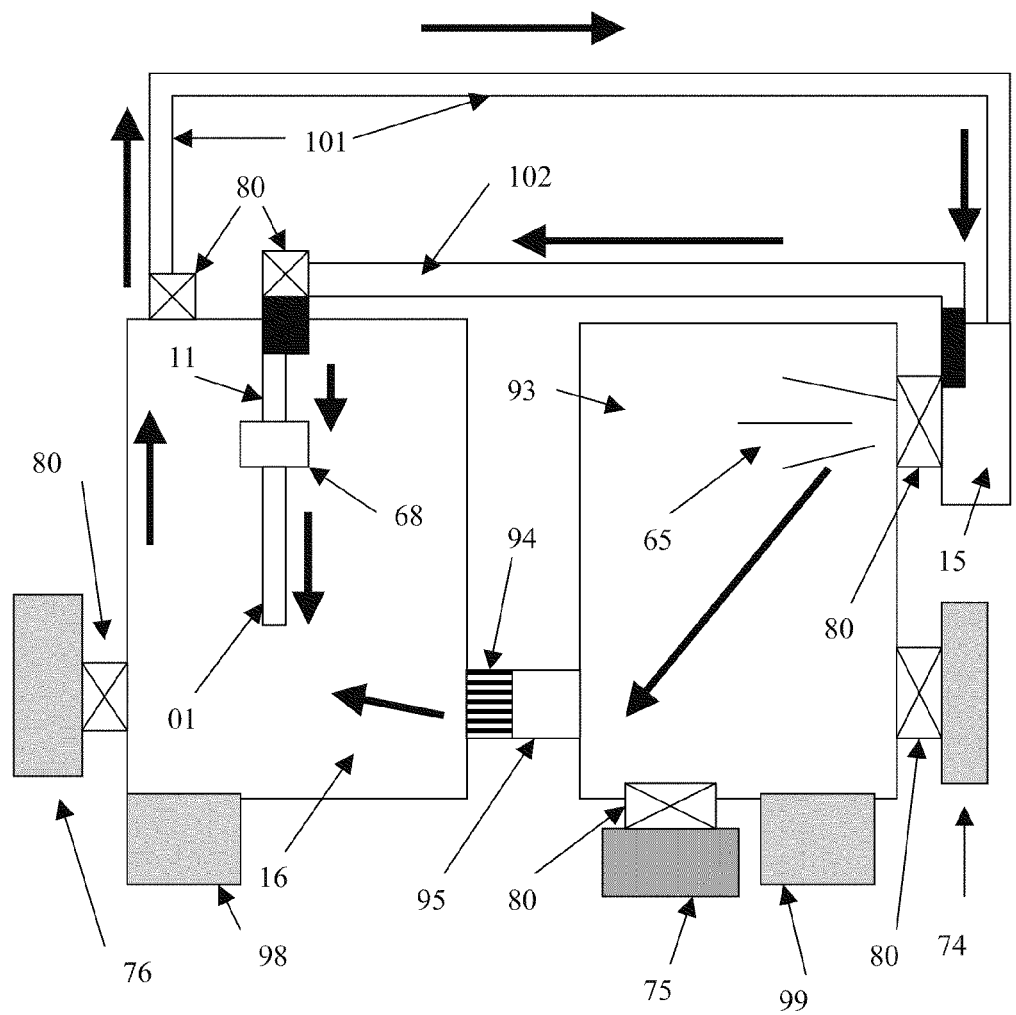

With reference to FIG. 30, the shadowing effect found with the delivery of "applied agent" (20) such as, but not limited to, aerosols (65), can be overcome in various ways. It is preferred, without limitation, that one way includes placing one or more endoscopes (01) in a sterilization chamber (16) and attaching each of them to a pressure interface assembly(s) (68) and then suspending the endoscopes (01) in the air within the sterilization chamber (16) via the pressure interface assembly(s) (68). This eliminates the chance for incomplete interaction, coating, or contact of the "applied agent" (20) with all of the surfaces of the endoscope (01). For example, the pressure interface assembly (68) may interface/articulate with either end of an endoscope (01), and the endoscope (01) may hang down toward the floor of the sterilization chamber (16) without touching anything.

Figure 8:
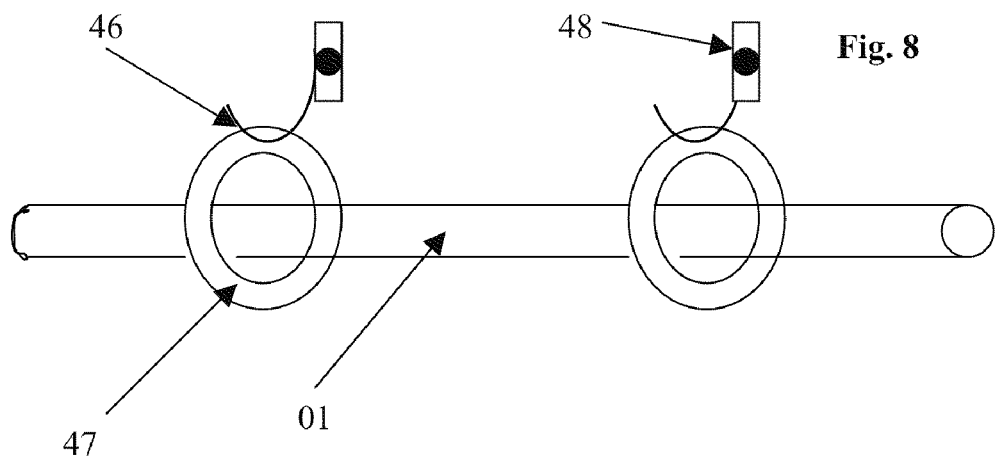
Figure 9:
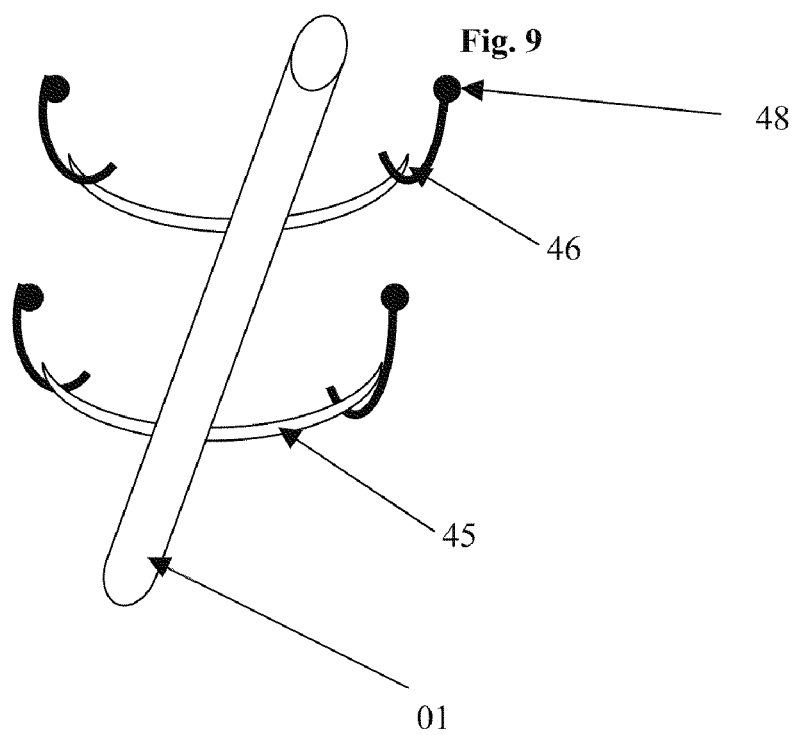

Referring to FIGS. 8-9, an alternative embodiment for suspending the endoscope (01) within the chamber (16) includes, without limitation, placing the endoscope (01) in one or more cradles (45) within the sterilization chamber (16), or encircling the endoscope (01) in one or more places with a material (47), in order to hang it within the sterilization chamber (16). In either case, the material (47) that holds the endoscope (01) should be, without limitation, as thin and narrow as possible, as well as sufficiently, porous, and permeable. The material (47) can also have, without limitation, any sufficient number of pores of any effective size. This material (47) can, without limitation, include various layers of various materials suitable for these purposes and it can also be absorbent. Some of this material (47) is then interfaced, connected, or otherwise attached to a hook(s) or other means (46), which are additionally attached using a suitable attachment member (48) to the interior of the sterilization chamber (16), in order to hold the material (47). This results in the suspension of the endoscope (01) in free space above the floor of the closed space or sterilization chamber (16) in which it is placed. The intent is to maximize the external surface area of the endoscope (01) that is exposed to "applied agent" (20) as well as allowing the "applied agent" (20) to quickly achieve its desired effect on the areas and surfaces that interface between the endoscope (01) and the material that is holding it. Previous laboratory work with an ultrasonic aerosol generator has shown that materials like glassine have shown sufficient permeability with the administration of an aerosol (65) having the preferred disinfectant or "applied agent" (20) contained therein. A high level of disinfection on the opposing side of this example barrier material (47) was achieved.

Figure 10:
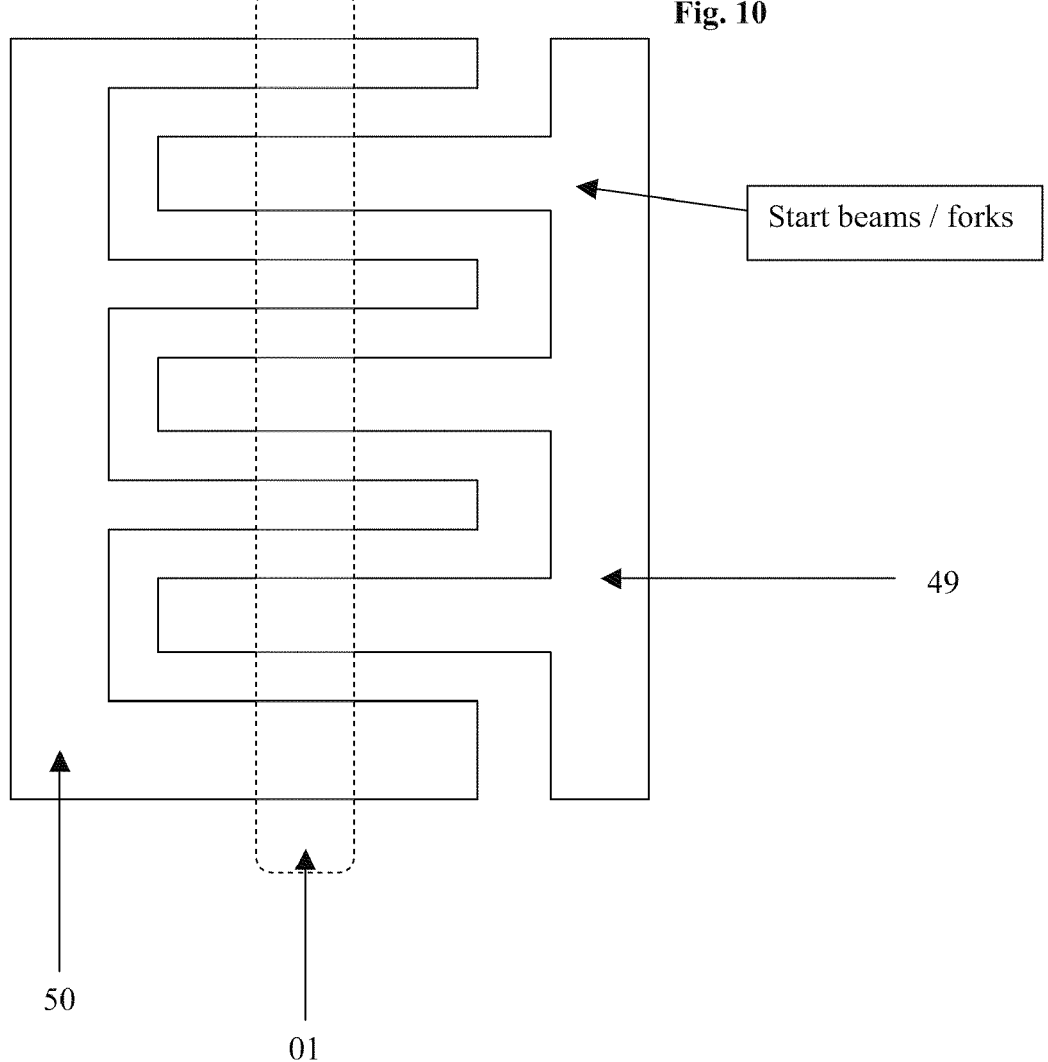
Figure 11:
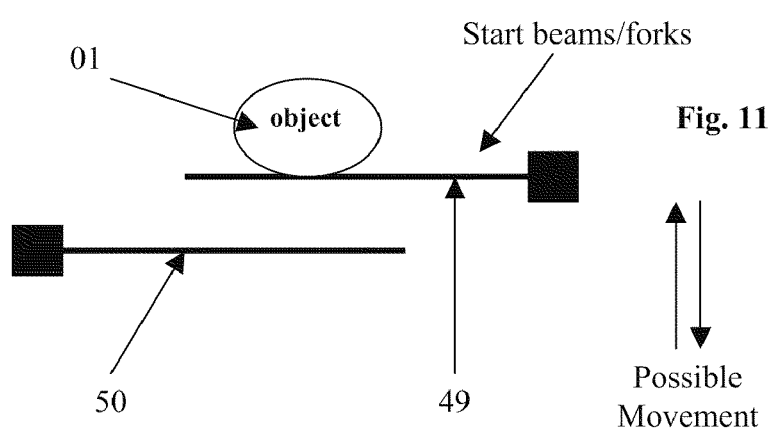

With reference to FIGS. 10-11 and 24-25, the shadowing can also be overcome by the incorporation and use of movable fork(s) or beam(s) (49),(50) within the closed space or sterilization chamber (16) of the present invention, as shown in FIGS. 10-11. The endoscope (01) is first placed or positioned on one or more beam(s) or fork(s) (herein "start beams") (49). One or more beam(s) or fork(s) (herein "opposing beams") (50) are also provided and they are intended to loosely interlock or intermesh with and/or oppose the start beams (49) without touching the start beams (49). The beams or forks (49),(50) can vary in size and shape as desired. The start beams (49) or opposing beams (50) can be designed or constructed so that the endoscope (01) will not roll or move off of the beams. In order to maintain the position of the endoscope (01) on the various beams (49),(50), they can have one or more, without limitation, indentations, ridges, bumps, or protrusions of various sizes, shapes, and heights. They may also, without limitation, slope or curve upward at various angles at locations including, but not limited to the ends of the beams (49),(50). During the application of the "applied agent" (20), the start beams (49) or opposing beams (50) move, by way of any mechanical means that are known in the art, resulting in the transfer of the endoscope(s) (01) so that it is moved from either the start beams (49) to the opposing beams (50) or from the opposing beams (50) to the start beams (49). This allows all of the endoscope (01) surfaces to be covered with the "applied agent" (20) as a result of exposing those portions of the surface of the endoscope (01) covered by the beams (49) when the endoscope (01) is moved onto the beams (50), or vice versa. These beams (49),(50) can then reverse their movement during the drying cycle to allow all of the endoscope (01) surfaces to dry if it is necessary. The beams (49), (50) can move in either direction, or reverse their motion, one or more times for various steps in any processing cycle. The movement of the beams (49),(50) can also vary, without limitation, in speed and range of motion, and are controlled in a manner well known in the art. It is preferred, without limitation, that the beams (49),(50) move at least at a speed or rate where the object can be effectively, efficaciously, or gently, transfer from one of the beams (49),(50) to the other. At least one of the beams (49), (50) moves vertically up or down relative to the other causing the object to transfer from one of the beams (49), (50) to the other and thus exposing an area of the object previously covered by one of the beams (49), (50). It is preferable that the object does not pivot or rotate, while transferred from one beam (49), (50) to the other or while resting on the beams (49), (50). Any digital or analog controller known to those skilled in the art can, without limitation, control the operation of the movable fork(s) or beam(s) (49),(50), as discussed later. A digital controller such as, but not limited to any programmable logic circuit (PLC) or other means known to those skilled in the art can, without limitation, control the operation of and be signaled the status of, the movable fork(s) or beam(s) (49),(50), all in way know. The status of the movable fork(s) or beam(s) (49),(50) can, without limitation, signal and initiate other processes such as, but not limited to, the commencement of any drying activities. The beams (49),(50) maybe constructed from the same materials used to construct the sterilization chamber (16) or pressure interface assembly (68).

The closed space, closed system of space, or sterilization chamber (16) can be purged, flowed, and/or filled with air or other gas from the outside environment (fresh filtered air) either before and/or after the "applied agent" (20) or other liquids are administered or applied in the sterilization chamber (16). The fresh air/gas is moved into the closed space, closed system of space, or sterilization chamber (16) via any air/gas pump, vacuum pump, blower, fan, or other means to move air, or source of pressurized air or gas (hereafter transfer device) (17), (51) and can move the fresh air at various volumes, rates, or speed. In either case, this can contribute to the removal of moisture, liquids, and/or "applied agent" (20) from the surfaces of the endoscope (01), and other surfaces and areas within the closed space or sterilization chamber (16). The time needed to effectively remove the moisture, liquids, and/or "applied agent" (20) that had coated, interfaced, interacted, enveloped, or had contact with the surfaces, or filled areas, within the closed area or sterilization chamber (16), is dependent on variables such as, but not limited to, the application time, temperature, relative humidity, flow rate, volume, and velocity, of the fresh air. It can also include the temperature of the targeted surfaces or endoscope (01) and/or areas. The variables can vary in order to remove the moisture, liquids, and/or "applied agent" (20) from these surfaces and areas in a manner that is as quick and effective as possible. The air/gas from the outside environment (fresh filtered air) can also be used to remove moisture, liquids, and/or "applied agent" (20) present in the interior space or ducts (08) of the endoscope (01) within the sterilization chamber (16). This can, without limitation, be accomplished by operating the same air/gas pump, vacuum pump, blower, fan, or other means (44),(17) which is used to create a positive or negative air/gas pressure within the pressure interface assembly (68) that is attached to the object or endoscope (01), in order to flow fresh air/gas through places such as, but not limited to, the interior space or ducts (08) of the object or endoscope (01). This is shown in greater detail in FIGS. 4-5. The time needed to effectively remove the moisture, liquids, and/or "applied agent" (02) from the surfaces in this application will vary and is affected by variables including but not limited to the number, shape, diameter, and length of the interior spaces or ducts (08) of the endoscope (01), as well as the application time, temperature, relative humidity, flow rate and volume, and velocity, of the applied fresh air/gas. The variables such as, but not limited to, the fresh air/gas temperature, flow rate, volume, velocity, and relative humidity, can vary in order to remove the moisture, liquids, and/or "applied agent" (20) in a manner that is as quick and effective as possible. The fresh air/gas that is used in this particular application can be sourced from either the fresh air/gas from the outside environment that is flowed or moved into the sterilization chamber (16), or it can be sourced directly from the outside environment. The air/gas from the outside environment can be treated to reduce its relative humidity and can be heated to various temperatures before it enters the closed space, sterilization chamber (16), or endoscope (01). The means to heat the air/gas (52) (29) is not specifically set forth, but known to those skilled in the art. Heating the air/gas can contribute to the accelerated removal of any moisture, liquids, and/or "applied agent" (20) from the surfaces and areas within the closed space, closed system of space, or sterilization chamber (16), in addition to the external and internal surfaces or ducts (08) of the object(s) or endoscope(s) within the closed space or sterilization chamber (16). The air/gas from the outside environment can be filtered before it enters into the closed space, sterilization chamber, or endoscope (01). The fresh air/gas can be filtered with one or more filters (53) such as but not limited to a 99.9% HEPA filter or other high efficiency filter, or with other filters or means for filtering air/gas that is not specifically set forth, but known to those skilled in the art. The filter (53) can limit or prevent the contamination of the endoscope (01) within the closed space or sterilization chamber (16). The exhaust port (39) the air/gas within the closed system of space or sterilization chamber can also be incorporated into the present invention. The exhaust system and/or outlet or exhaust port (39), can also include the use of one or more filters (54) or combination of filters (54) such as, but not limited to, a gas filtering filter, 99.9% HEPA filter or other high efficiency filter, or other filters or means for filtering (54) that is not specifically set forth, but known to those skilled in the art. The exhaust is means for exhaust (39) can help to establish a flow of fresh air/gas through the closed system of space or sterilization chamber (16) and allows the incoming fresh air/gas to fully replace the air/gas inside of these areas which can prevent the buildup of positive pressure within the closed system of space or sterilization chamber (16). The exhausted flow of air/gas also helps to remove the "applied agent" (20) from the closed system of space or sterilization chamber (16). The filter(s) (54) can prevent the contamination of objects or endoscopes (01) within the closed system of space or sterilization chamber (16) by filtering any potential backflow of air and/or gases, as well as filter and remove any "applied agent" (20), or any contaminants, in the air/gas before they are exhausted out of the present invention and into the external environment. In many situations, air and gas filtering standards are dictated or impacted by regulatory entities, or by standards set within the industry in which the present invention operates. This may also affect the type or means of air and/or gas filters (53),(54) that are used in the present invention. The fresh air/gas can also be moved into and through the closed system of space or sterilization chamber (16) by locating a means to move the air/gas such as but not limited to an air/gas pump, vacuum pump, blower, fan or other transfer device (17),(51) as earlier described, at or near the exhaust port (39). The transfer device (17),(51) moves the air/gas can be located before or after any of the filter(s) (53),(54) that filters the inbound or exhausted air/gas.

Referring to FIG. 13, in bound air from the transfer device (17),(51) is passed through the filter (53), so that the inbound air/gas cannot contaminate the endoscope (01) inside of the closed space or sterilization chamber (16). The inbound fresh air/gas may also be heated by any means that can heat air/gas (52). The devices to move, filter, and heat the air/gas can be in any order. The air/gas is then circulated, moved, or flowed into the closed space or sterilization chamber (16). The transfer device (39) is used to ventilate the air/gas and the "applied agent" (20), out of the closed system of space or sterilization chamber (16). The vented air/gas can also pass through one or more filters (54) before it is ventilated into the external environment. One or more closure device (35) is also present to effectively close off, seal, or separate, the closed system of space or sterilization chamber(s) (16) from the inbound fresh air/gas inlet (38), the transfer port (39), and/or any of the tubes, ducting, channels, tunnels, etc., that connect the fresh air/gas inlet or exhaust air/gas outlet to the closed system of space or sterilization chamber (16). The transfer device (35) can be a door, flap, valve, lid, panel, or other physical means to contain the "applied agent" (20) or any air/gas that is utilized or applied or administered, as well as the agents or substances that are used to wash the endoscopes (01) as discussed earlier.

With reference to FIGS. 21, 22 and 26-32, the at least one dehumidification apparatus (74) within the sterilization chamber(s) (16) or other area(s) where the "applied agent" (20) in aerosol form (65) is applied may also, without limitation, be located within the sterilization chamber(s) (16) or other targeted area(s), or otherwise be operatively coupled or attached to and/or about the sterilization chamber (16), or anywhere along the path of any circulated or recirculated air/gas (31) and aerosol (65), or other connected spaces. It is preferred, without limitation, that the dehumidification activity occurs any time after the application of the "applied agent" (20) in aerosol form (65), which is unique in comparison to the prior art. The prior art teaches that dehumidification is a necessary activity for achieving efficacious results before the application of certain applied agent such as, but not limited to, vaporized hydrogen peroxide, and is therefore not claimed in the present invention. However, dehumidification activities can, without limitation, take place any time during or after the processing of the endoscope in the present invention. The use of one or more dehumidification apparatus(s) (74) in the present invention is beneficial in situations that include, but are not limited to, where the air/gas and/or the "applied agent" (20) in aerosol form (65) within the sterilization chamber(s) (16) or targeted area(s) cannot be evacuated for reasons known to those skilled in the art. The dehumidification apparatus (74) is constructed and operated in a manner known to those skilled in the art, and includes, but is not limited to a dehumidification means where air/gas from the targeted environment is moved over any chilled media, to remove the humidity. The dehumidification apparatus (74) may reduce or even sustain the humidity level to any desired level or percentage of humidity, and in a manner that is known to those skilled in the art. However, it is preferred, without limitation, that if the dehumidification apparatus (74) is operated, it reduces the humidity to a level that is at least efficacious or meets standards known to those skilled in the art. It is more preferred that the humidity is reduced to a level that is equal to or less than 50% relative humidity. It is even more preferred that the humidity is reduced to a level that is equal to or less than 20% relative humidity. After the sterilization chamber (16) or other targeted area(s) are dehumidified or reach the desired humidity level, the air/gas within these spaces may be, without limitation, processed in a manner known to those skilled in the art to remove any substances such as, but not limited to, any remaining odors, chemicals, smells, vapors, aerosols, or gases. This can be accomplished in ways that include, but are not limited to, passing the air/gas in the at least one sterilization chamber (16) or other targeted area(s) through at least one filter (75) that contains carbon, charcoal, or any other applicable filtering means known to those skilled in the art. The processed air/gas can be, without limitation, returned back to the sterilization chamber (16) or any space connected to the at least one sterilization chamber (16). The removal of any odors, chemicals, smells, vapors, aerosols, or gases, can also, without limitation, take place at any time. The at least one filter (75) can also be operated simultaneously with the dehumidification apparatus (74). It is preferred, without limitation, that the at least one filter (75) is utilized after the sterilization chamber (16) or other targeted area(s) are dehumidified to a desired or effective level. Without being limited, the processing of the atmosphere within the sterilization chamber (16) or other targeted area(s), with the at least one filter (75), can also be triggered in various ways including, but not limited to using any, timers, dew point levels, or humidity levels, to start the filtering (75) process.

The effective operation of the present invention can be accomplished using any electrical and/or electronic means to control the mechanisms that the present invention depends on for its proper function. The electrical and electronic means can be programmed or electrically designed to execute, manage, monitor, or control, the present invention and are not specifically set forth, but known to those skilled in the art. This means can monitor and control the function, as well as the timing of use, of any electrically dependent components such as, but not limited to, any valves, any means used for the production of the "applied agent" (20) used in the present invention as well as any related mechanisms or systems, any means used to flow or move the air/gas and/or "applied agent" (20) within or out of the present invention, any means to heat the aerosol, air/gas, or floor of the sterilization chamber, any means used to flow or move the air/gas and/or "applied agent" (20) through the internal spaces or ducts (08) of the object or endoscope (01), any packaging equipment or related systems, as well as any other microcomputers that are used, such as but not limited to, microcomputers or printers utilized to record and report the operating parameters of each cycle of use.

According to an embodiment, the present invention also improves the current art by decreasing the processing time for the simultaneous or non-simultaneous cleaning and disinfection/sterilization of both the interior and exterior surfaces of an object or plurality of objects such as, but not limited to, an endoscope (01). It is more preferred, without limitation, that the activities such as, but not limited to, the soaking, washing, cleaning, disinfection/sterilization, rinsing, and drying, of both the interior and exterior surfaces of an endoscope (01) or plurality of endoscopes (01) take place within the same sterilization chamber (16). The pressure interface assembly (68) of the present invention may or may not be used, without limitation, in this embodiment. However, it is preferred, without limitation, that the pressure interface assembly (68) is not used in this particular embodiment, and that the endoscope (01) is connected to a pipe, hose, tube, or other delivery means that can supply any surfactant, rinse liquid, or applied agent to the endoscope (01), or otherwise a supply tube (11).

Initially, processing steps utilized in the current art are followed in this embodiment and involve the use of a washer (72) or other device or means, known to those skilled in the art, for activities including, but not limited to, cleaning, washing, or disinfecting/sterilizing endoscopes (01) (herein called "washer") (72). The washer (72) may, without limitation, be integrated into the design or construction of the enclosed area, chamber, or sterilization chamber (16) of the present invention. These steps are known to those skilled in the art and include, but are not limited to, wiping or cleaning the endoscope (01) to remove, or attempt removal of, any unwanted liquid, debris, contaminants, or other substances, and then placing the endoscope (01) into a washer (72) and interfacing it with a supply tube (11). The endoscope (01) is placed on a rack, or other means known to those skilled in the art, to hold or position the endoscope (01) within the sterilization chamber (16) and/or washer (72). The supply tube (11) enables various liquids including but not limited to, surfactant, and high purity rinse water, to be moved through the various ducts (08) of the endoscope (01) at various stages of the cleaning process. The object or endoscope (01) may be, without limitation, soaked for any effective time period within liquids or compounds such as, but not limited to, any surfactants or any other combination of various cleaning liquids, within the washer (72). The washer (72) then subjects, sprays, covers, floods, or a combination thereof, the endoscope (01) with liquids or compounds such as, but not limited to, any surfactants or other cleaning liquids, both inside and outside of the object or endoscope (01) for an effective amount of time all in a manner known to those skilled in the art. After this cycle is completed, the inside as well as outside surfaces of the object or endoscope (01) may be exposed to a liquid rinse, which preferably comprises one or more liquids that includes high purity water. It is preferred, without limitation, that the endoscope (01) is rinsed with high purity water. Any surfactant solution and rinse liquid can be used and it may be any temperature when it is used. It is preferred, without limitation, that the surfactant used in the present invention is any surfactant that meets standards acceptable to the industry in which it is used, as well as any regulatory requirements. It is preferred, without limitation, that the rinse liquid used in the present invention is any high purity rinse water that meets standards acceptable to the industry in which it is used, as well as any regulatory requirements. The cycle time for the exposure of the endoscope (01) to any surfactant and rinse liquid can vary but is at least efficacious. In order to decrease the processing time, improvements are made at this point to the current art.

According to an embodiment, any or all attributes, functions, features, or designs of the endoscope washer (72) utilized in the current art may be integrated into the sterilization chamber (16) that is previously described in the present invention.

According to another embodiment after the endoscope (01) is treated with any surfactant and/or rinse water, its internal and external surfaces may be dried. Any drying technique previously described in the present invention or known to those skilled in the art can be utilized in this embodiment. It is preferred that any air/gas that may be heated and/or filtered is flowed or otherwise moved into the sterilization chamber (16) and/or washer (72) in which the endoscope (01) is positioned in order to dry it. The creation of a vacuum within the sterilization chamber (16), of various negative atmospheric pressures, but at least an efficacious level of vacuum, may also be used for drying purposes. The level or amount of dryness can vary. The drying of the internal and external surfaces of the endoscope (01) can be done simultaneously or at different times, or it can be treated as mutually exclusive activities that can or cannot be undertaken. It is preferred, without limitation, that all of the internal and external surfaces of the endoscope (01) are dried and that this activity is done simultaneously.

The internal surfaces of the endoscope (01) can be dried, without limitation, by flowing air/gas through the supply tube (11) and then through the endoscope (01). The air/gas can be heated and/or filtered. The air/gas, or other means used for surface drying, may be applied for any length of time to any surfaces of the endoscope (01).

According to an embodiment, the supply tube (11) is, without limitation, designed, manufactured, and incorporated, into the design of the sterilization chamber (16) and/or washer (72), and the endoscope (01) in a manner known to those skilled in the art. The supply tube (11) may also be effectively connected to any supply of, including, but not limited to, air/gas, liquid surfactant, liquid for rinsing, and source of applied agents, in a manner known to those skilled in the art. The various controlled access points or the valves (35) that control the exposure of the endoscope (01) to various substances such as, but not limited to, air/gas, liquid surfactant, liquid for rinsing, and anti-pathogen/toxin/fungal/sporicidal agent(s) or substance(s), to the supply tube (11) or endoscope (01) can be, without limitation, designed and controlled in a manner known to those skilled in the art.

According to a preferred embodiment, after the endoscope (01) undergoes various activities such as, but not limited to, cleaning with surfactant, rinsing with water and optionally alcohol in separate steps, and drying (if desired), the inside and outside surfaces of the endoscope (01) are treated with an anti-pathogen/toxin/fungal/sporicidal agent(s) or substance(s) that is, in the form of any aerosol. The applied agents are created, generated, and/or administered in or into the sterilization chamber (16) and/or the washer (72) in which the endoscope (01) are placed. It is preferred that the treated surfaces are dried before the anti-pathogen/toxin/fungal/sporicidal agent(s) or substance(s) is applied, such as by passing a drying gas over the surfaces of the endoscope (01). This may enhance the efficacy or cycle time of the process. It is preferred, without limitation, that the applied agent is an aqueous aerosol (65), consisting of, but not limited to, any acidic oxidizer, generated by one or more of any transducer (22) or ultrasonic nebulizer(s) (22) of any design or construction. However, any other means for generating an effective aerosol (65) may also be used. The aerosol (65) may be of any concentration, number, size, or density, however it is preferred, without limitation, that the aerosol (65) includes a plurality of droplets whose size is five micron or less. The aerosol (65) can be generated from any liquid that is at any temperature. The aerosol (65) is delivered to the internal surfaces, areas, or ducts (08) of the endoscope (01) via a supply tube (11). This particular embodiment may improve the current art by significantly decreasing the endoscope (01) processing time.

According to an embodiment, the applied agent that is used to treat the endoscope (01) may also be in the form of any gas, plasma, or vapor. The prior art includes the use of an applied liquid agent through the various internal spaces such as, but not limited to the ducts (08) of an endoscope (01), as well as over the various external surfaces of the endoscope (01), and is therefore not claimed in the present invention.

After this cycle is completed, the ducts (08) or internal, as well as external surfaces of the endoscope (01) may be exposed or subjected to a liquid rinse, which includes one or more liquids, substances, or compounds, that includes, but is not limited to high purity water or alcohol, all in a manner known to those skilled in the art. The endoscope (01) can then be removed from the sterilization chamber (16) and/or washer (72) and hung to dry.

According to another embodiment as an alternative to hanging the endoscope (01) to dry, the inside and outside surfaces of the endoscope (01) are dried with various means such as, but not limited to, the at least one dehumidification apparatus (74), formation of a negative atmospheric pressure or vacuum in the sterilization chamber (16), or air/gas or heated air/gas, before it is removed from the sterilization chamber (16) and/or washer (72). It is preferred that the air/gas is heated. The air/gas can be heated in a manner known to those skilled in the art. The supply tube (11) may be used to supply air or heated air to the inside surfaces or ducts (08) of the endoscope (01).

According to a preferred embodiment, after the endoscope (01) undergoes various activities such as cleaning with surfactant, rinsing, drying (if desired), and the inside and outside surfaces of the endoscope (01) are then treated with an applied agent, the final rinsing activity(s) are not utilized and the endoscope is instead subjected to the final drying activity. This offers the benefit of significantly reducing processing time. It is preferred that this is conducted with an "applied agent" (20) in the form of an aqueous aerosol (65), including, but not limited to, any acidic oxidizer, generated by one or more of any transducer (22) or ultrasonic nebulizer(s) (22) of any design or construction. However, this embodiment can also pertain to any gas, plasma, vapor, and/or aerosol that is utilized.

According to an embodiment, any objects including, but not limited to endoscope(s) (01), the atmosphere in which they reside, any surfaces in the sterilization chamber (16) or any interconnected areas, can be, without limitation, cooled before, during, or after the aerosol (65) is introduced. This effect will apply to interfacing surfaces, as well as the inside surfaces of object(s) or endoscope(s) such as, but not limited, lumens or duct(s) (08). This embodiment should not be confused with what was taught by U.S. Pat. No. 4,512,951 (Koubek at al., 1983), which is incorporated herein by reference in its entirety, including any references cited therein. Koubek et al., 1983, taught a method of sterilization where a liquid of aqueous hydrogen peroxide is vaporized, and the uniformly vaporized mixed hydrogen peroxide-water vapors are delivered into an evacuated sterilizer chamber, and the articles to be sterilized are cooled prior to the introduction of the vapor (or are cooled by the evacuation of air from the sterilizing zone) to a temperature below the dew point of the entering vapors. The condensing vapor deposits as a film on the cool surfaces (col 2, line 40-51). Koubek et al., 1983, also mentions in claim 2 that the result of vaporization was a mixed "gaseous vapor" consisting of hydrogen peroxide and water vapor free of solid contaminants.

The present embodiment of "cooling" is intended to optimize the attraction of heated droplets of the "applied agent" to the targeted area in conformance with the laws of physics and not to create a condensate from a vapor as taught by Koubek. Here, the difference in temperate between the droplets and the object's surface causes the droplet to be attracted to the surface as if it were electrically charged.

Basic principles applied in this embodiment are taught in the text entitled, "Aerosol Technology" by William C. Hinds (1982), which is incorporated herein by reference in its entirety, including any references cited therein. Without limitation, the cooling of the said object(s), surfaces, or environment or atmosphere, within the sterilization chamber (16), in the present invention, can accentuate the performance or efficacy of the aerosol (65) generated by the aerosol generator (15) in the present invention. In addition, and without being limited to a mechanism or method, the aforementioned principles taught by William C. Hinds (1982), show that the efficacy, efficiency, and performance of the process in the present invention can be further enhanced by introducing an aerosol (65), consisting of a heated "applied agent" (20) into the sterilization chamber(s) (16) containing objects with cooled surfaces.

The cooling of any object(s) or endoscope(s) (01), surface(s), space(s), environment(s), or atmosphere(s), within the sterilization chamber(s) (16), can be accomplished by any means other than by decreasing the pressure or pulling a vacuum. Creating a vacuum in an enclosed area and applying an aerosol was taught in the prior art by U.S. Patent Application No. 2005/0042130 A1 (Lin et al., 2003). However, Lin et al., was silent with respect to cooling surfaces within the sterilization chamber or targeted area, and only mentioned the vaporization of the applied aerosol as being an enhancement or advantage that further vacuum past 5 torr would provide (pg. 2 paragraph 28). The vacuum utilized by Lin et al., (pg. 2 paragraph 28) to obtain data, was intended to move the aerosol through the sterilization chamber. In addition, using a vacuum to cool object(s), surfaces, or environment or atmosphere, within a enclosed area, would not be desired in this embodiment due to the complexity and expense involved in designing a chamber for the necessary vacuum and the expense of acquiring the necessary pump, which is all known to those skilled in the art. It is desired that another means for cooling object(s) or endoscope(s) (01), surfaces, or environment or atmosphere, within the sterilization chamber(s) (16), other than utilizing a vacuum, be utilized.

As shown in FIGS. 20-23 and 26-32, it is preferred, without limitation, that the sterilization chamber(s) (16) and its atmosphere, environment, objects, or any of the targeted surfaces within the sterilization chamber(s) (16), be cooled with air or gas that is cooled or chilled in a manner known to those skilled in the art. It is further preferred, without limitation, that the air or gas is cooled or chilled with one or more chill coils or refrigerated air systems (76) that are known to those skilled in the art. It is even more preferred, without limitation, that the air or gas within the sterilization chamber(s) (16), is cooled or chilled with any thermoelectric cooling means (76), or any means known in the art for reducing temperature that uses a Peltier effect (76). Any number, size, capacity, or combination, of the thermoelectric cooling system(s) (76) and/or the refrigerated air system(s) (76), which chill or cool the air or gas can be, without limitation, attached to the aerosol generating apparatus (15) in the present invention, be separate from the aerosol generating apparatus (15) and connect with at least one pipe (77) or outbound cooled air pipe(s) (78) or inbound air pipe(s) (79) that connect with the targeted area(s) or sterilization chamber(s) (16), or it can be part of, directly or indirectly connected to, or positioned anywhere within the targeted area(s) or sterilization chamber(s) (16) to be treated. It can be controlled by one or more PLC(s) or remote PLC(s) in a manner known to those skilled in the art. Without limitation, any pipe(s) that lead to (79) or from (78) the source of the thermoelectric or refrigerated cooled or chilled (76) air or gas, can be operably separated from the targeted area(s) or sterilization chamber(s) (16) with one or more of any door, valve, cap, or other separating device or valve (Herein called "valve(s)") (80) that can be controlled by one or more PLC(s) or remote PLC(s). It is preferred, without limitation, that the valve(s) (80) can effectively seal. Without limitation, one or more valve(s) (80) may also be positioned at any location between the location where the administered air/gas or aerosol enters any pipe(s) (78) (79) or targeted area(s) or sterilization chamber(s) (16) and the aerosol generating apparatus (15), and can be controlled by one or more PLC(s) or remote PLC(s). The said valve(s), pipe(s), or other related part(s) or component(s) can all be constructed from any material that is compatible, and suitable for use with the liquid (20). Without limitation, the amount or duration of air or gas that is flowed into or recirculated through the targeted area(s) or sterilization chamber(s) (16), the locations that the air or gas is flowed into or out of the targeted area(s) or sterilization chamber(s) (16), the temperature of the air or gas, as well as the temperature of the surfaces within the targeted area(s) or sterilization chamber(s) (16) can vary depending on variables such as, but not limited to, the application, the level of performance that is desired, desired application time, as well as the volume of the targeted area(s) or sterilization chamber(s) (16).

Without limitation, the temperature of the atmosphere, surfaces, or space(s) in the targeted area(s) or sterilization chamber(s) (16) can be cooled to at least nine degrees Fahrenheit below the temperature of the applied liquid (20). It is preferred, without limitation, that the temperature of the atmosphere, surfaces, or space(s) in the targeted area(s) or sterilization chamber(s) (16) be cooled to at least nine to twenty-five degrees Fahrenheit below the temperature of the applied liquid (20). However, it is more preferred, without limitation, that the temperature of the atmosphere, surfaces, or space(s) in the targeted area(s) or sterilization chamber(s) (16) be cooled to at least forty degrees Fahrenheit or lower. It is further preferred, without limitation, that the temperature of the atmosphere, surfaces, or space(s) in the targeted area(s) or sterilization chamber(s) (16) be cooled to at least thirty-two degrees Fahrenheit or lower. It is very preferred, without limitation, that the temperature of the surfaces, or space(s) within the targeted area(s) or sterilization chamber(s) (16) be cooled at least to any effective temperature approximately near or below the dew point within the targeted area(s) or sterilization chamber(s) (16). The temperature of the applied liquid (20) of which the aerosol (65) is created or the temperature to which the aerosol (65) is heated with other means, can also vary.

The internal space(s) of an object including, but not limited to any, lumen(s), channel(s), or duct(s) (08), of an object or endoscope (01), as well as the areas and surfaces that interface or articulate with the pressure interface assembly (68) can also be, without limitation, cooled with air or gas that is cooled or chilled. The cooled or chilled air or gas can be delivered with means such as, but not limited to, the pressure interface assembly (68) which can be directly or indirectly connected to the source of the cooled or chilled air or gas. The pressure interface assembly (68) can be, without limitation, separated from the source of the cooled or chilled air by any PLC controlled valve (80).

According to an embodiment, any object(s) (01) processed in the sterilization chamber(s) (16) or other connected areas, can also include, without limitation, one or more of any package that is unsealed, partially sealed, or hermetically sealed. The package(s) can have one or more of any contents. Referring to FIGS. 22 and 26-28, it is preferred, without limitation, that the package(s) be placed in the sterilization chamber (16) on perforated rack(s) (90) containing perforations of any size, shape, or construction. It is also preferred, without limitation, that the packages incorporate at least an effective or efficacious amount of any sufficiently porous or permeable materials such as, but not limited to, Tyvek, or other similar functioning material, in their design. Furthermore, the package can be, without limitation, designed in manner known to those skilled in the art, so that it can allow free passage of any quantity of air, gas, and/or any agent(s) through the package.

With reference to FIGS. 22-23, according to another embodiment, and without limitation, any product used to measure or indicate the efficacy of the one or more processing steps utilized within the sterilization chamber (16) such as, but not limited to, chemical or biological indicator(s) used for validation of high level disinfection or sterilization (herein called "indicator(s)") (81), can be located anywhere within the sterilization chamber (16). It is more preferred, without limitation, that one or more of these indicator(s) (81) be located in a indicator enclosure (83) behind one or more valve(s), door(s), cap(s), or cover(s) (herein called "door(s)) (82). It is preferred, without limitation, that the door(s) (82) effectively seal the indicator enclosure (83) in which the indicator(s) (81) are located, to prevent any unwanted damage or changes to the indicator(s) (81) from any substance(s) or condition(s) that may be used in the sterilization chamber(s) (16) during various processing steps. Referring to FIGS. 22-23, the door(s) (82) can open at any time including, but not limited to, before or during the application of the applied agent(s) (20) inside the sterilization chamber(s) (16). The door(s) (82) can be opened, closed, or maintained in their desired position, at any time and for any duration of time. The movement of the door(s) (82) at any time can be, without limitation, PLC controlled, all in a manner known to those skilled in the art.

According to an embodiment, and referring to FIGS. 24-25, it is preferred, without limitation, that various objects or endoscope(s) (01) can be, without limitation, held, supported, hung, cradled, suspended, positioned, or supported, within the sterilization chamber(s) (16) by one or more of various devices including, but not limited to any, clamp(s), fork(s) (49)(50), beam(s) (49)(50), shelve(s), rack(s) (90), member(s), hook(s), ring(s), cradle(s), or support pillar(s) (herein called "object support(s)") (84). Furthermore, these object support(s) (84) can, without limitation, be designed to have one or more opening(s) (85), which can serve as either, or both, outlet(s) or inlet(s), through which various substances or materials used to process the object(s) or endoscope(s) (01) within the sterilization chamber (16) can flow such as, but not limited to any, surfactant, rinse water, high purity rinse water, alcohol solution, "applied agent(s)", air/gas, heated air/gas. These various substances or materials may flow either out of or into the one or more opening(s) (85), where by doing so, they can directly or indirectly contact or interact with various surfaces the object(s) or endoscope(s) (01). Any number of opening(s) (85) may be utilized and positioned anywhere on the object support(s) (84), but it is preferred, without limitation, that at least an effective number of object support(s) (84) are used, and they at least effectively face various surfaces of the object or endoscope (01). The opening(s) (85) may be any size, shape, geometry, or design, known to those skilled in the art. The various substances or materials used to process the object(s) or endoscope(s) (01) within the sterilization chamber (16) can flow or move at any quantity, rate, or pressure, at any time. These materials or substances can be, without limitation, supplied to the opening(s) (85) through one or more of various supply hose(s), pipe(s), conduit(s), or channel(s) (herein called "process hose(s)") (88), and are flowed or moved in a manner known to those skilled in the art. One or more of any opening(s) (85) can be, without limitation, dedicated and plumbed (87) with an aerosol generation device (15) to flow one or more of any substance(s) or material(s) at any time, or at any designated time(s), and for any duration of time, in order to process the object(s) or endoscope(s) (01).

Figure 24:
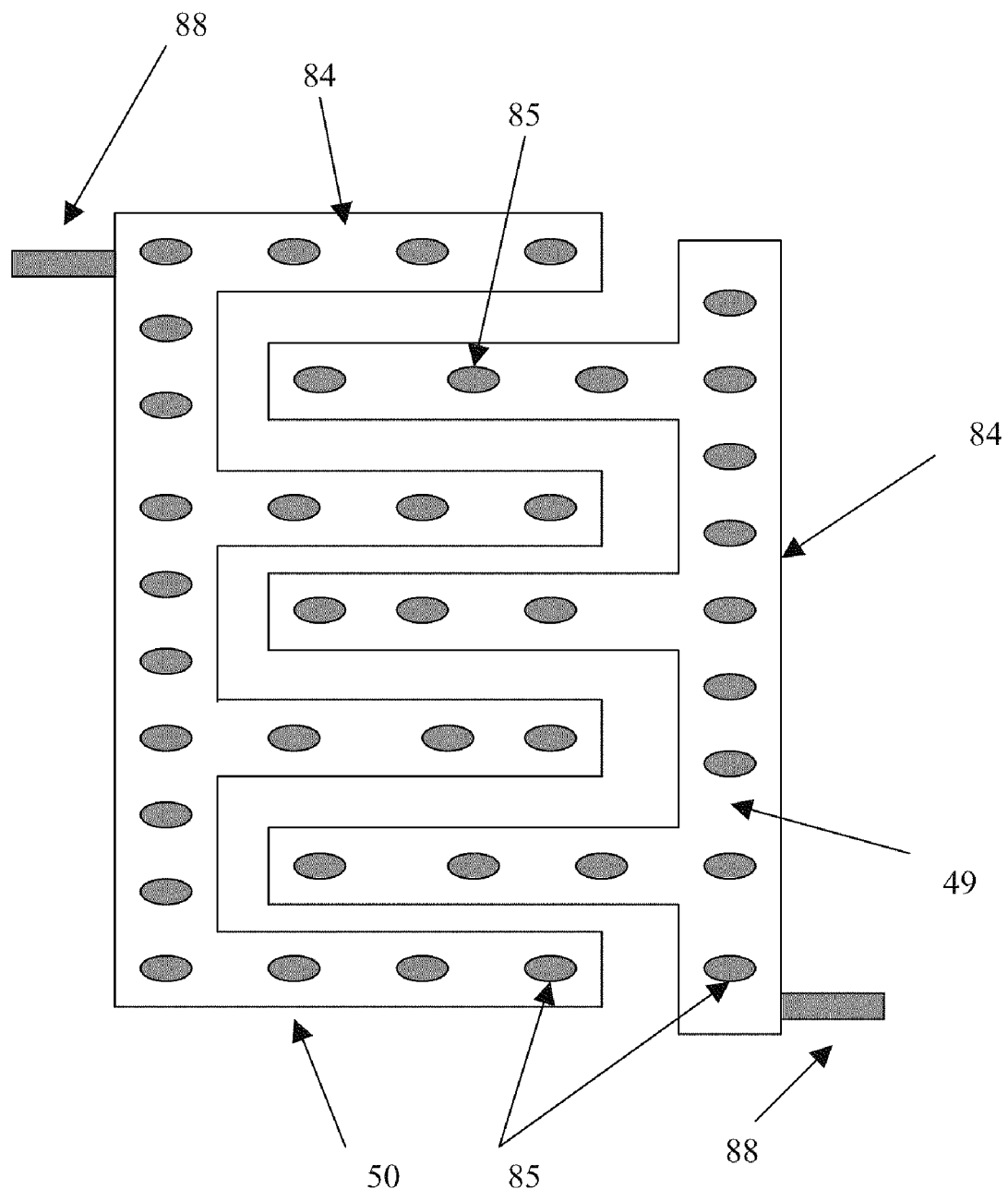
Figure 25:
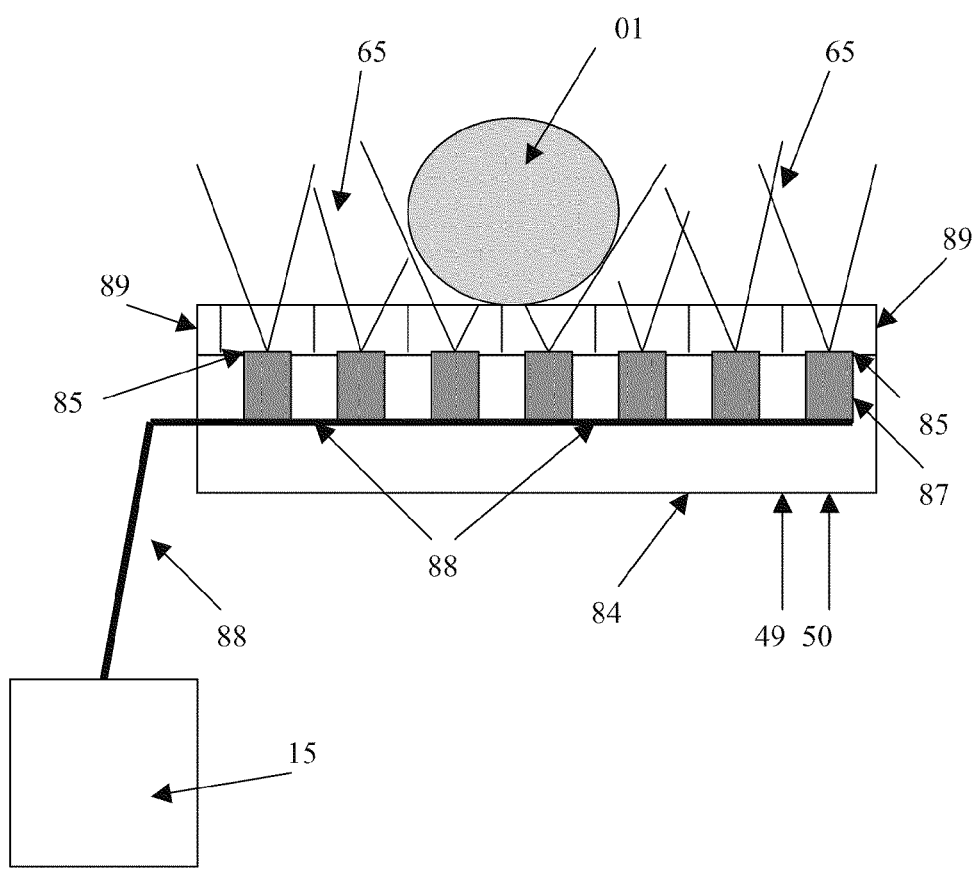

Referring to FIGS. 24-25, an object interface material (herein called "object interface") (89) may also, without limitation, be positioned or maintained between the object support(s) (84) and the object(s) or endoscope(s) (01). This assures that all of the surfaces of the object(s) or endoscope(s) (01) in contact with the object interface (89) have sufficient exposure to the aerosol (65) of an "applied agent" (20) through either direct and/or indirect contact, for their sanitization, disinfection, high-level disinfection, or sterilization, depending on the agent used and the exposure time. For example and without limitation, any absorbent object interface (89) material may also indirectly deploy/transmit the "applied agent" (20) that is aerosolized, to the articulated areas and surfaces by the interaction or movement of the "applied agent" (20) through the interface formed from the selected material.

Referring to FIG. 25, the object interface (89) can be, without limitation, porous, and/or permeable, and be constructed from materials that can provide effective performance and the desired level of efficacy for the process. The object interface (89) can be, without limitation, constructed of one or more layers of material. The object interface (89) may also have absorbent characteristics to improve its efficacy and performance. The object interface (89) is intended, without limitation, to allow the various substances or materials used to process the object(s) or endoscope(s) (01) within the sterilization chamber (16), to move or flow through the interface layer at a controlled, but effectual rate.

Referring to FIG. 25, the object interface (89) can be manufactured from a variety of materials including, but not limited to, cloth, gauze, manufactured fibers, synthetic fibers, natural fibers or materials, cellulose, polymer, polyolefin, glass, metal, ceramic, carbon, combinations of these materials, or other materials know in the art. The object interface (89) can be coated with chemicals, materials, or substances including, but not limited to, polymer(s), polyolefin, wax, silver, lipid, oil, enamel, paint, carbon, metal, combinations of these materials, or other materials known in the art. The object interface (89) can be electrically or electrostatically charged or uncharged in order to attract the "applied agent" (20). The electrostatic potential or polarity of the various materials as well as the "applied agent" (20) can, without limitation, vary. Object interface materials (89) that are developed in the future, may be utilized to improve the efficacy of the design or its application to certain objects or endoscopes (01). The object interface (89) and its effectiveness can vary with variables including but not limited to, its size, width, surface area, shape, fit, thickness, density, hardness, elasticity, flow rate, porosity, permeability, evenness of air/gas flow, mechanical properties, physical properties, and other variables known to those skilled in the art. However, the effectiveness and efficacy of each object interface (89) that is used may, without limitation, increase with attributes such as, but not limited to, the uniformity of these variables throughout the interface that is used. The object interface (89) material can be, without limitation, permanently attached to the object support(s) (84), or it can be designed to be easily removed and replaced, all in a manner known to those skilled in the art. The "object support(s) (84) can also, without limitation, be constructed either partially or completely from the same materials, and in the same manner and concept, as the object interface (89).

According to an embodiment, one or more object(s) or endoscope(s) (01) can be placed inside of, and effectively sealed within, one or more sterilization chamber(s) (16). The sterilization chamber(s) (16), can be any size, shape, or geometry. The object(s) or endoscope(s) (01) can be, without limitation, located or positioned on any racks (90), object supports (84), cradle(s), or other effective materials (47) inside the sterilization chamber(s) (16). It is preferred, without limitation that the racks (90) are preferably perforated, and the perforations can be any size, number, and construction. The object(s) or endoscope(s) (01) can be, without limitation, washed, cleaned, and dried, inside of the sterilization chamber (16), all in a manner known to those skilled in the art.

Referring to FIGS. 22, 26-29, and 32, the object(s) or endoscope(s) (01) can also, without limitation, be one or more package(s) (91) of various types and construction. It is also preferred, without limitation, that the package(s) (91) are constructed from at least an effective or efficacious amount of any sufficiently porous film, sheet, or other material, such as, but not limited to any, woven or unwoven substrate, spun-bonded olefin, or microporous material (92). Any other effective packaging materials or package designs known to those skilled in the art may also be utilized. The package can be, without limitation, designed in manner known to those skilled in the art, so that it can allow free passage of any quantity of air, gas, and/or any agent(s) through the package. This can, without limitation, enable the passage of an efficacious or effective amount of the "applied agent" (20), which is administered into the sterilization chamber(s) (16), to move into the package(s) (91) and treat or interact with the various surfaces within the package(s) (91). The package(s) (91) does not have to be washed or cleaned, unless desired or needed. However, the various object(s) or endoscope(s) (01), including any package (91) can, without limitation, undergo any processing steps or cycle(s) that includes, but it not limited to any, soaking, washing, rinsing, drying, and/or temperature decrease or cooling, before they are treated with an "applied agent" (20). The various processing steps or cycle(s), can occur or transpire for any length of time. It is preferred, without limitation that the processing steps or cycle(s), occur or transpire for at least an effective amount of time, and in any effective order. The package(s) (91) can be, without limitation, sealed, partially sealed, or hermetically sealed. The package(s) (91) can be designed in various ways known in the art. The package(s) (91) may also have any, without limitation, interior volume, wall thickness, or permeability for various substances. It is preferred, without limitation, that at least an effective interior volume, wall thickness, or permeability, is used. The packages (91), object(s) or endoscope(s) (01) can also, without limitation, be designed in a manner known to those skilled in the art, so that they contain, hold, maintain, or are integrated with, one or more of any products used to measure the efficacy of the one or more processing steps utilized within the sterilization chamber such as, but not limited to, any indicator(s) (81). In addition, the packages (91), object(s) or endoscope(s) (01) can also, without limitation, be designed in a manner known to those skilled in the art, so that the status of the indicator(s) (81) can be easily visible, or visible from outside of the package (91).

Referring to FIGS. 26-30, the sterilization chamber(s) (16) can directly or indirectly connect to one or more secondary chamber(s) (93). Both chambers (16),(93) should also be designed and constructed to withstand, without limitation, various positive and negative pressures, including pressures that are near a vacuum. The secondary chamber(s) (93) can be any size, shape, geometry, and have any number of connected areas. It is preferred, without limitation, that the secondary chamber(s) (93) is at least the same size, as the sterilization chamber(s) (16). It is more preferred that the secondary chamber(s) (93) is at least effectively larger than the than the sterilization chamber(s) (16). Without limitation, one or more of any valves, caps, airlocks, or other effectively sealing door(s) known in the art that can control the flow of any gas, (herein called "pressure valve(s)" (94)), can be positioned anywhere along the path of any moving air, gas, and/or "applied agent" (20) between the sterilization chamber(s) (16) and the secondary chamber(s) (93). One or more paths may be used to flow or move various material(s) or substance(s) including, but not limited to any, air, gas, and/or "applied agent" (20) between the sterilization chamber(s) (16) and the secondary chamber(s) (93). The pressure valve(s) (94) control the flow of any air, gas, and "applied agent" (20) between the sterilization chamber(s) (16) and the secondary chamber(s) (93). The pressure valve(s) (94) can have any effectual operation speed for opening and closing, means of sealing, size, and design. The valve(s) (94) can also be, without limitation, positioned or directly or indirectly connected anywhere on or to, the sterilization chamber (16).

Figure 26:
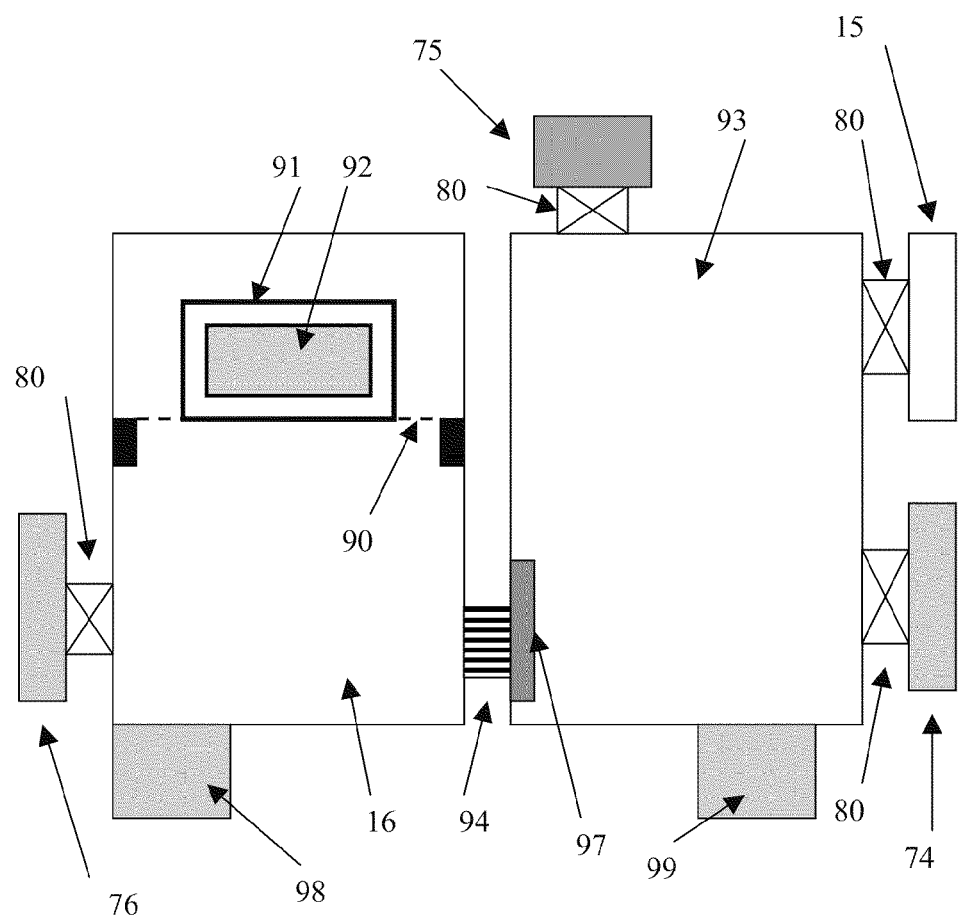
Figure 27:
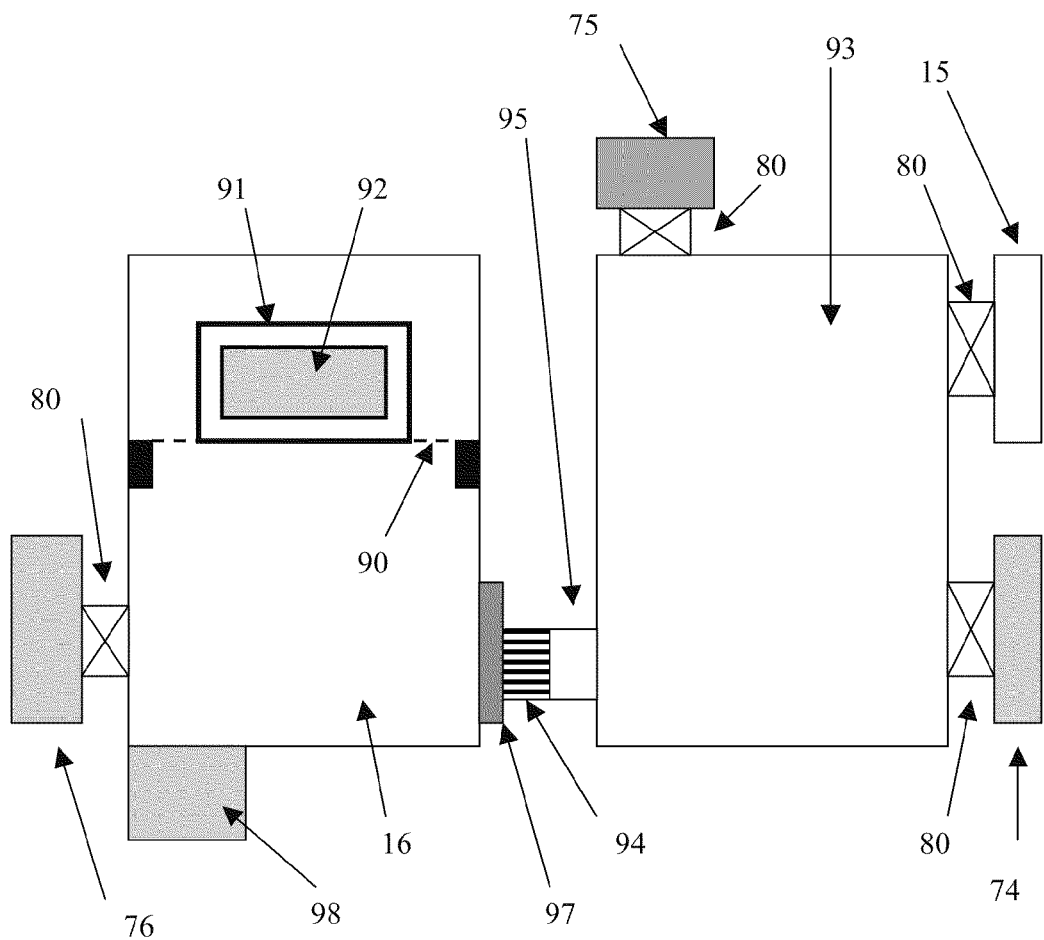
Figure 28:
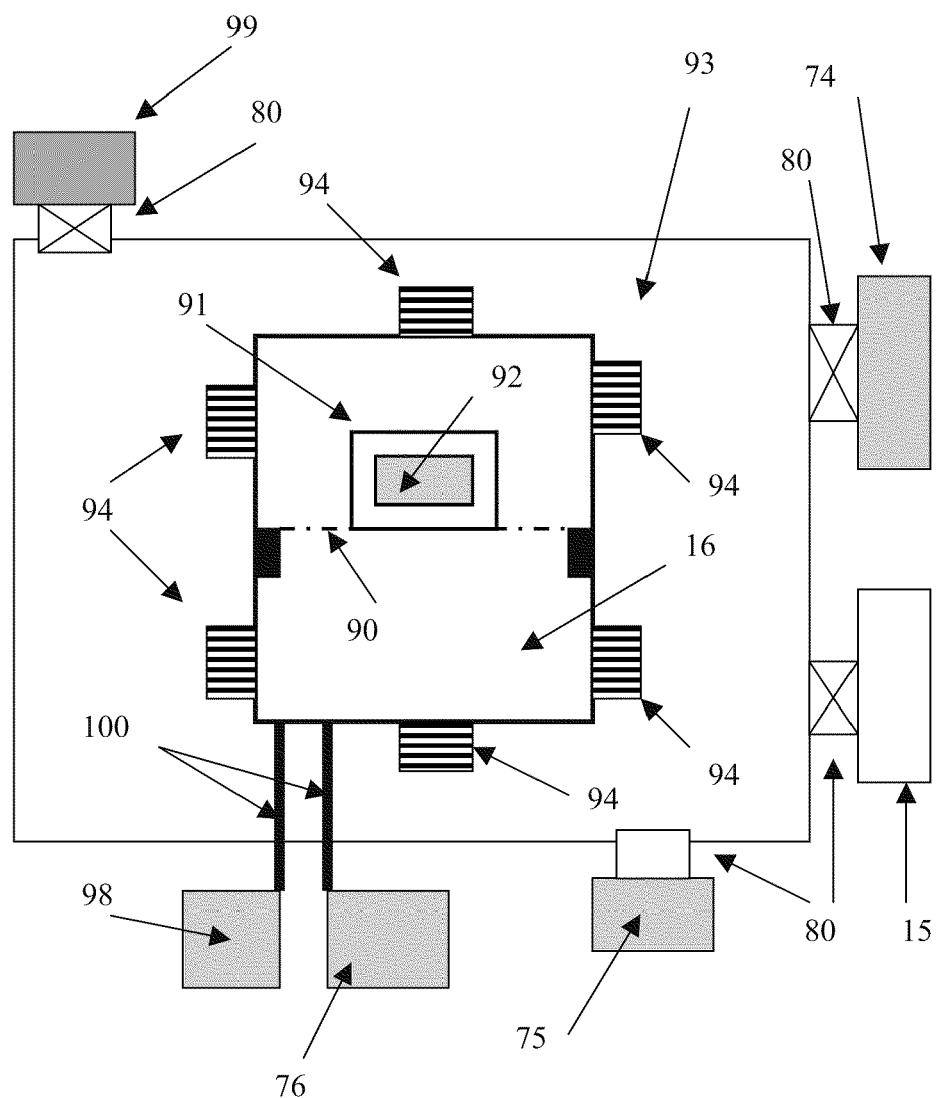
Figure 29:
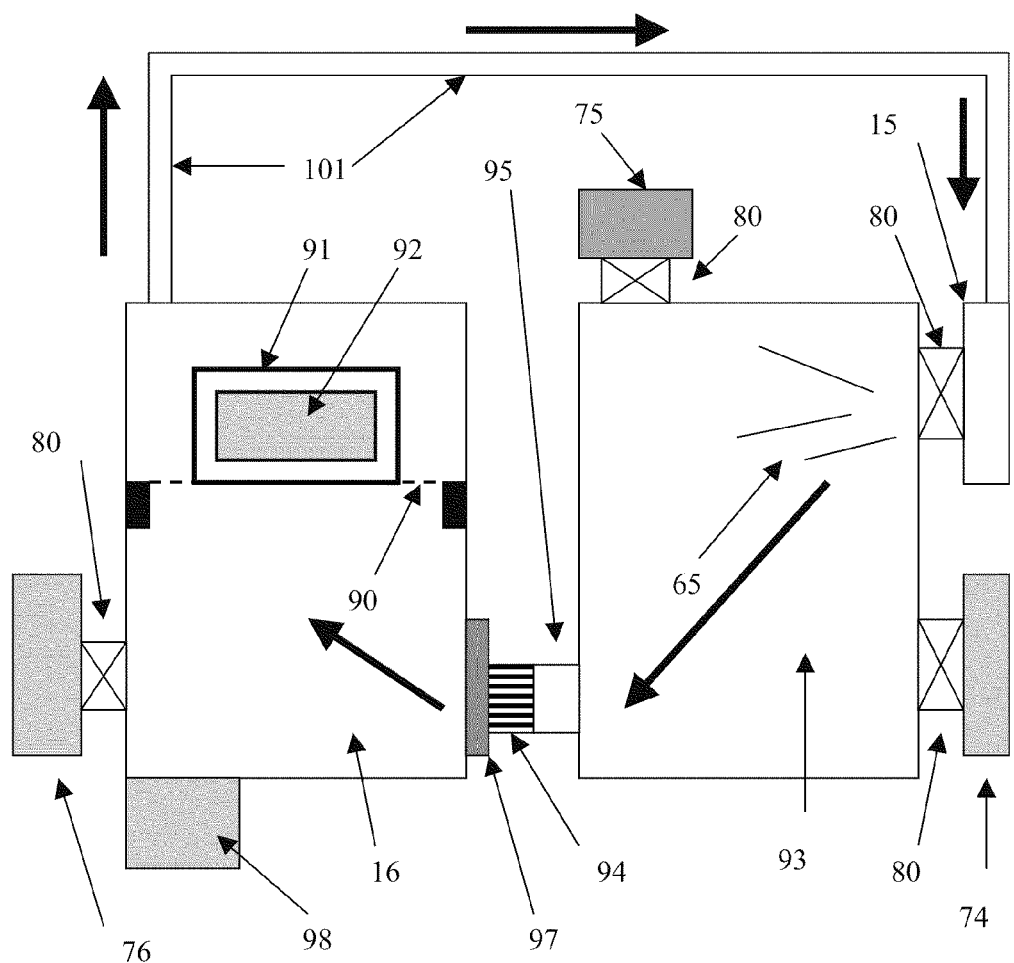

As shown in FIGS. 26-27 and 29, one or more of any filter(s) (97) of any size, filtering capacity, level of filtering, or construction, known in the art, may be, without limitation, utilized or positioned anywhere between the sterilization chamber(s) (16) and the secondary chamber(s) (93), to filter the flow of any air, gas, and "applied agent" (20). Any filter(s) (97) may be used, which may have any level of effective filtering, but is preferred, without limitation, that one or more filter(s) (97) is used that can filter out or remove airborne aerosol particles larger than or equal to, "three" micron in size. It is more preferred, without limitation, that one or more filter(s) (97) be used that can filter out or remove airborne aerosol particles larger than or equal to, "one" micron in size. It is even more preferred, without limitation, that one or more filter(s) (97) be used that can filter out or remove airborne aerosol particles larger than or equal to, "half or 0.5" micron in size. It is very preferred, without limitation, that one or more filter(s) (97) be used that can filter out or remove airborne aerosol particles larger than or equal to "a tenth or 0.1" micron in size.

As shown in FIGS. 26-27 and 29, filtering a generated or deployed aerosol was initially demonstrated by the inventors of the present invention in a public area at the Richland, Wash. Municipal Airport on Oct. 9, 2003. Staff from Washington State University, observed aerosol created by the aerosol generating apparatus described in the present invention, pass through a long tortuous path created with 150 feet of six inch diameter flex ducting, that terminated with various filter media including a HEPA filter and a furnace filter. This same system was used to dehumidify and dry the system of ductwork, after the aerosol was deployed. Any filter may also be used, without limitation, to filter any output from the means to generate and deploy the "applied agent" (20).

In a preferred part of this embodiment, the sterilization chamber(s) (16) can be located inside of a larger secondary chamber (93) that can also effectively seal. In this application, as shown in FIG. 28, it is advantageous that both chambers (16),(93) have one or more sealing doors (96), that are at least adequately sized and positioned, so that objects or endoscopes (01) may be easily moved from the sterilization chamber (16) for use.

In a very preferred part of this embodiment, and without limitation, the secondary chamber (93) can be located anywhere outside of the sterilization chamber (16), and effectively connect with the sterilization chamber (93) in one or more places. As shown in FIGS. 26-27 and 29-30, this connection can be made with one or more of various pipes, supply hose(s), conduit(s), or channel(s) (herein called "flow pipe(s)") (95). The sterilization chamber(s) (16) in this application should also have one or more sealing doors (96) that are at least adequately sized and positioned, so that objects or endoscopes (01) may be easily moved from the sterilization chamber (16) for use.

Referring to FIGS. 26 and 30, and according to an embodiment, the pressure within the sterilization chamber(s) (16) can be, without limitation, reduced with any suitable negative pressure device (98) known to those skilled in the art (such as a vacuum pump), to any effective pressure below atmospheric pressure, and more preferably near a vacuum. In comparison, the pressure within the secondary chamber(s) (93) can be, without limitation, increased with any positive pressure device (99) known to those skilled in the art (such as a positive pressure pump), to any effective pressure above standard atmospheric pressure. The secondary chamber(s) (93) is filled with the applied agent (20), and once it is effectively full or has reached an effective density, the one or more "pressure valve(s)" (94), can be opened to allow the "applied agent" (20) to flow or move into the sterilization chamber(s) (16) at any effective speed, quantity, or rate of flow to overwhelm the endoscope (01) or object in the sterilization chamber(s) (16). It is preferred, without limitation, that the one or more "pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 26 and 30, and. according to another embodiment, the pressure within the sterilization chamber(s) (16) can be, without limitation, kept effectively near standard atmospheric pressure in a manner known in the art. In comparison, the pressure within the secondary chamber(s) (93) can be, without limitation, increased with the positive pressure device (99) known to those skilled in the art, to any effective pressure above standard atmospheric pressure. The secondary chamber(s) (93) is filled with the applied agent (20), and once it is effectively full or has reached an effective density, the one or more "pressure valve(s)" (94), can be opened to allow the "applied agent" (20) to flow or move into the sterilization chamber(s) (16) at any, effective speed, quantity, or rate of flow. It is preferred, without limitation, that the one or more "pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 26-27 and 29-30 and, according to a preferred embodiment, the pressure within the sterilization chamber(s) (16) can be, without limitation, reduced with the negative pressure device (98) known to those skilled in the art, to any effective pressure below atmospheric pressure, and more preferably near a vacuum. In comparison, the pressure within the secondary chamber(s) (93) can be, without limitation, kept effectively near standard atmospheric pressure in a manner known to those skilled in the art. The secondary chamber(s) (93) is filled with the applied agent (20), and once it is effectively full or has reached an effective density, the one or more pressure valve(s) (94), can be opened to allow the "applied agent" (20) to flow or move into the sterilization chamber(s) (16) at any effective speed, quantity, or rate of flow. It is preferred, without limitation, that the one or more pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 1-2, 4-5, 12-13, 20-23, and 26-32, the applied agent (20) in these embodiments can, without limitation, continue being deployed or applied into the secondary chamber(s) (93) and/or the sterilization chamber(s) (16) until effective exposure or coverage of the surfaces in the targeted area(s) is achieved. Any amount of time can transpire after the deployment of the applied agent (20) is terminated, and the next processing step(s) or cycle(s) is started. This period of time is called the "dwell time". It is preferred, without limitation, that the dwell time is at least three minutes. It is more preferred, without limitation, that the dwell time is at least six minutes. It is even more preferred, without limitation, that the dwell time is at least ten minutes. It is very preferred, without limitation, that the dwell time is at least fifteen minutes. With reference now to FIGS. 26 and 30, after the "pressure valve(s)" (94), are opened, the pressure within either, or both, the sterilization chamber(s) (16) and/or the secondary chamber(s) (93), can be increased to any effective pressure, with the positive pressure device (99) known to those skilled in the art, for any effective period of time. In addition, after the pressure valve(s)" (94), are opened, the temperature within either, or both, the sterilization chamber(s) (16) and/or the secondary chamber(s) (93), can also be increased to any effective elevated temperature for any effective period of time using one or more means known to those skilled in the art. The sterilization chamber(s) (16) and its contents, and/or the secondary chamber(s) (93), can be, without limitation, further processed in a manner previously discussed in the present invention, including, but not limited to, any drying, dehumidification, or deodorizing activities. These various processing step(s) or cycle(s) can occur or transpire for any length of time, and in any effective order. In addition, any number of the steps or cycles in the present invention, or combination of the steps or cycles in the present invention, may without limitation, be repeated any number of times at any time, to efficaciously process the one or more object(s) (01) or package(s) (91). The one or more endoscope(s) or object(s) (01), or package(s) (91), may also, without limitation, be processed multiple times with a complete processing cycle, including various steps, in order to obtain the needed or desired level of efficacy. The one or more "pressure valve(s)" (94), can remain open or closed at any time, and for any time period that is needed, to complete the various processing steps within either, or both, the sterilization chamber(s) (16) and/or the secondary chamber(s) (93). Any components in the sterilization chamber can also, without limitation, be effectively cooled anytime before any applied agent (20) is administered. The pressure interface assembly (68) may also, without limitation, be used at any time.

Referring to FIGS. 20-23 and 26-32, and according to an embodiment, the various means used to process the object(s) or endoscope(s) (01) such as, but not limited to dehumidify with the dehumidification apparatus (74), chill or cool with any thermoelectric cooled or chilled air or gas system(s) (76) or refrigerated air or gas system(s) (76) the atmosphere, environment, objects, or any of the targeted surfaces, increase atmospheric pressure with the positive pressure pump (99) or decrease atmospheric pressure with the negative pressure pump (98), or remove substances with the filter(s) (75) such as, but not limited to, any remaining odors, chemicals, smells, vapors, or gases, within the one or more sterilization chamber(s) (16), secondary chamber(s) (93), or interconnected spaces, can be, without limitation, effectively interfaced or connected to these areas in various ways known to those skilled in the art. The thermoelectric air or gas cooling system(s) (76) and/or refrigerated air or gas system(s) (76), dehumidification apparatus (74), the filter(s) (75), the negative pressure device (98) and the positive pressure device (99) may also effectively interface or connect directly or indirectly to one or more areas such as, but not limited to any, targeted area(s) or sterilization chamber(s) (16), secondary chamber(s) (93), or connected space(s). The thermoelectric air or gas cooling system(s) (76) and/or refrigerated air or gas system(s) (76), dehumidification apparatus (74), the filter(s) (75), the negative pressure device (98) and the positive pressure device (99) may be, without limitation, separated from the one or more sterilization chamber(s) (16), secondary chamber(s) (93), or interconnected spaces with one or more valve(s) (80), that can all be controlled by one or more PLC(s) or remote PLC(s) in a manner known to those skilled in the art.

Figure 31:
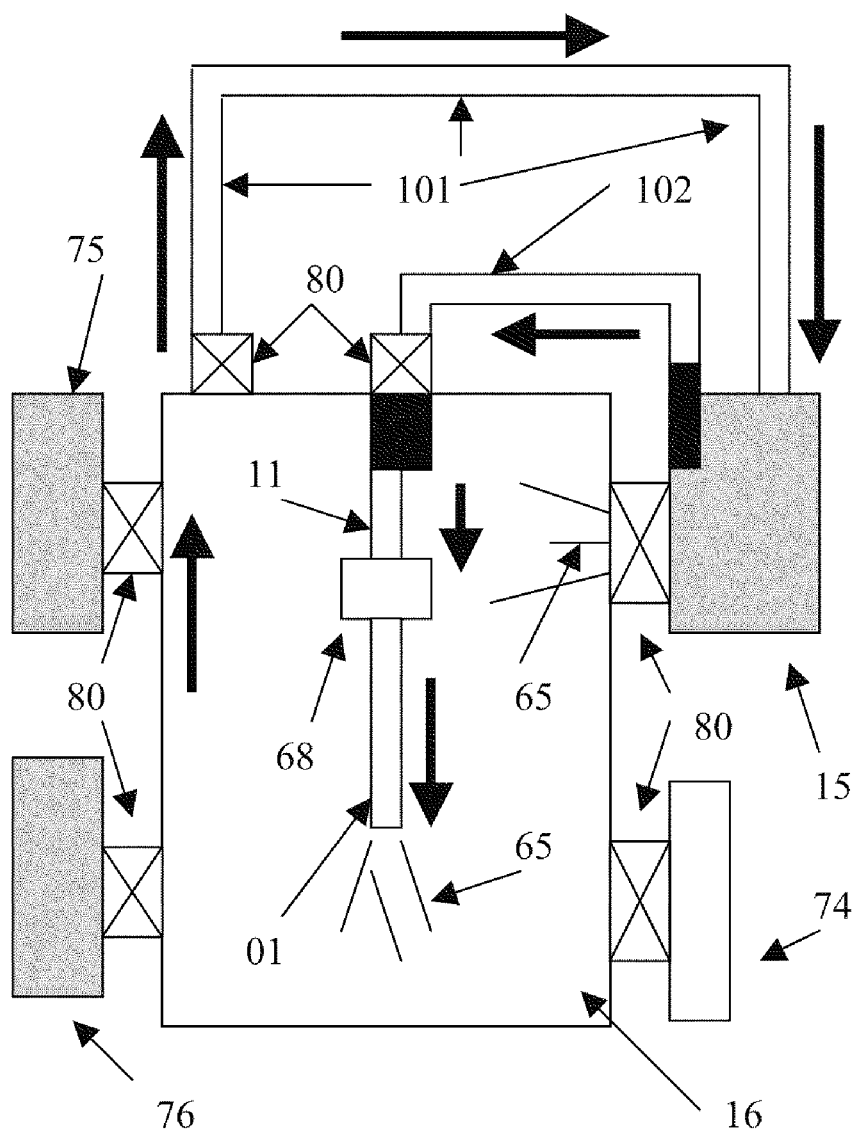
Figure 32:
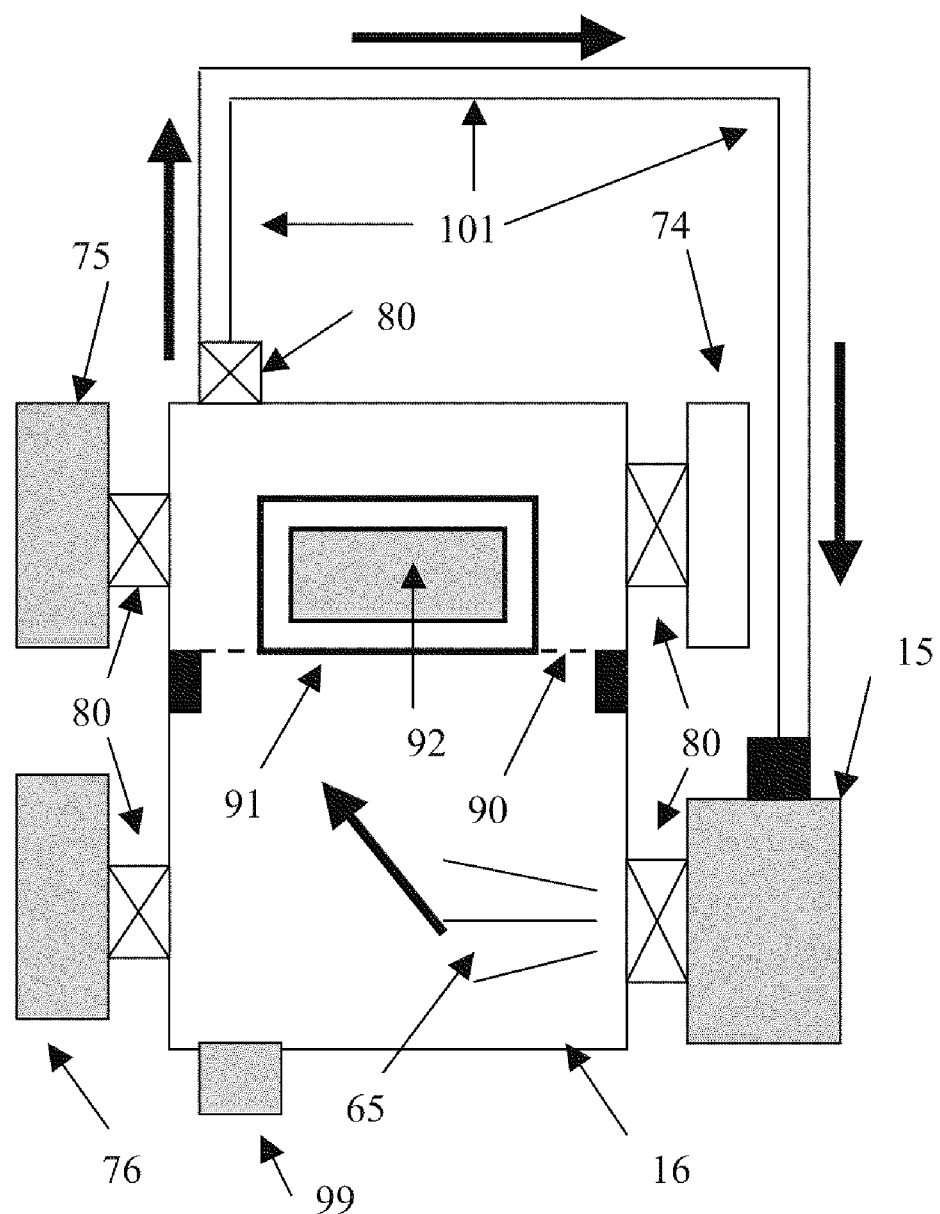
FIG. 32 is a schematic diagram of one sterilization chamber with a dehumidification apparatus, a filter, a thermoelectric air or gas cooling system(s) and/or refrigerated air or gas system(s), and a pressure source. The sterilization chamber is connected to one pipe that connects the aerosol generator directly to the sterilization chamber, forming a closed loop system for air/gas flow.

According to an embodiment, and with reference now to FIGS. 29-33, the sterilization chamber(s) (16) can, without limitation, directly or indirectly connect with the aerosol generator(s) (15) via one or more "return pipe(s)" (101). This connection can allow air/gas and any applied agent(s) (20) or aerosol(s) (65) delivered into the sterilization chamber (16) to flow or recirculate back to the aerosol generator (15) forming a loop. Referring to FIGS. 30 and 31, one or more "connector pipe(s)" (102) can also, without limitation, directly or indirectly connect with the aerosol generator (15) and one or more supply tube(s) (11) and/or one or more pressure interface assembly(s) (68) located within the sterilization chamber. It is preferred, without limitation, that the applied agent(s) (20) or aerosol(s) (65) are delivered via the connector pipe(s) (102) to the supply tube(s) (11) and/or pressure interface assembly(s) (68) from the aerosol generator (15). Without limitation, one or more valve(s) (80) may also be positioned at any location between the sterilization chamber (16) and the aerosol generator (15) for both the return pipe(s) (101), and/or the delivery pipe(s) (102). The valve(s) (80) can all be controlled by one or more PLC(s) or remote PLC(s) in a manner known to those skilled in the art.

Referring to FIGS. 26-27 and 29-30, the various gas(s), air, substances, or materials, used to process the object(s) or endoscope(s) (01) can flow or move at any quantity, rate, or pressure, at any time. These materials or substances can be, without limitation, supplied or moved through one or more of various supply hose(s), pipe(s), conduit(s), or channel(s) (herein called "process pipe(s)") (100), and are flowed or moved to or from the one or more sterilization chamber(s) (16), secondary chamber(s) (93), or interconnected spaces, to or from at least one of the thermoelectric air or gas cooling system(s) (76) and/or refrigerated air or gas system(s) (76), dehumidification apparatus (74), the filter(s) (75), the negative pressure device (98) and the positive pressure device (99) in a manner known to those skilled in the art.

According to an embodiment, it is preferred, without limitation, that the following processing steps or cycle(s), occur or transpire in the following order, for at least an effective amount of time. Delays of time may also, without limitation, exist between the various processing steps or cycle(s). If any delay of time does occur, it is preferred, without limitation, that it is at least an effective amount of time. The order of the one or more of these processing steps or cycle(s) can also, without limitation, be changed. In addition, one or more, or combinations of one or more, of these steps may also be, without limitation, utilized. One or more of these processing steps or cycle(s) can also, without limitation, be removed and not enacted. In addition, any number of the steps or cycles in the present invention, or combination of the steps or cycles in the present invention, may without limitation, be repeated any number of times at any time, to efficaciously process the one or more object(s) (01) or package(s) (91). The one or more endoscope(s) or object(s) (01), or package(s) (91), may also, without limitation, be processed multiple times with a complete processing cycle, including various steps, in order to obtain the needed or desired level of efficacy. Without being limited, the pressure interface assembly (68) can also be utilized when its application can provide an efficacious or desired outcome. The one or more processing steps or cycle(s) are as follows:

a) Soak object(s) or endoscope(s) (01) in a solution.
b) Wash object(s) or endoscope(s) (01).
c) Rinse object(s) or endoscope(s) (01).
d) Dry object(s) or endoscope(s) (01).
e) Cool or chill surfaces of object(s) or endoscope(s) (01).
f) If two interconnected chambers, separated by one or more valves(s) (94), are used, and the object(s) or endoscope(s) (01) are located within the sterilization chamber (16), and it is connected to a secondary chamber (93), the two chambers can each be subjected to various combinations of any pressure within the chambers. The one or more valve(s) (94) are opened once the secondary chamber (93) is effectively and sufficiently filled with the applied agent(s) (20).
g) Generate and deploy the applied agent(s) (20) to the various surfaces within sterilization chamber (16) for effective amount of time.
h) Terminate application of applied agent(s) (20)
i) Use effective dwell time if needed.
j) Dehumidify sterilization chamber (16) and secondary chamber (93) (if used), to obtain an effective relative humidity.
k) Filter the atmosphere within the sterilization chamber (16) and secondary chamber (93) (if used), to remove any odor(s), gase(s), or vapor(s), with an effective filtering device(s) (75).

Figure 33:
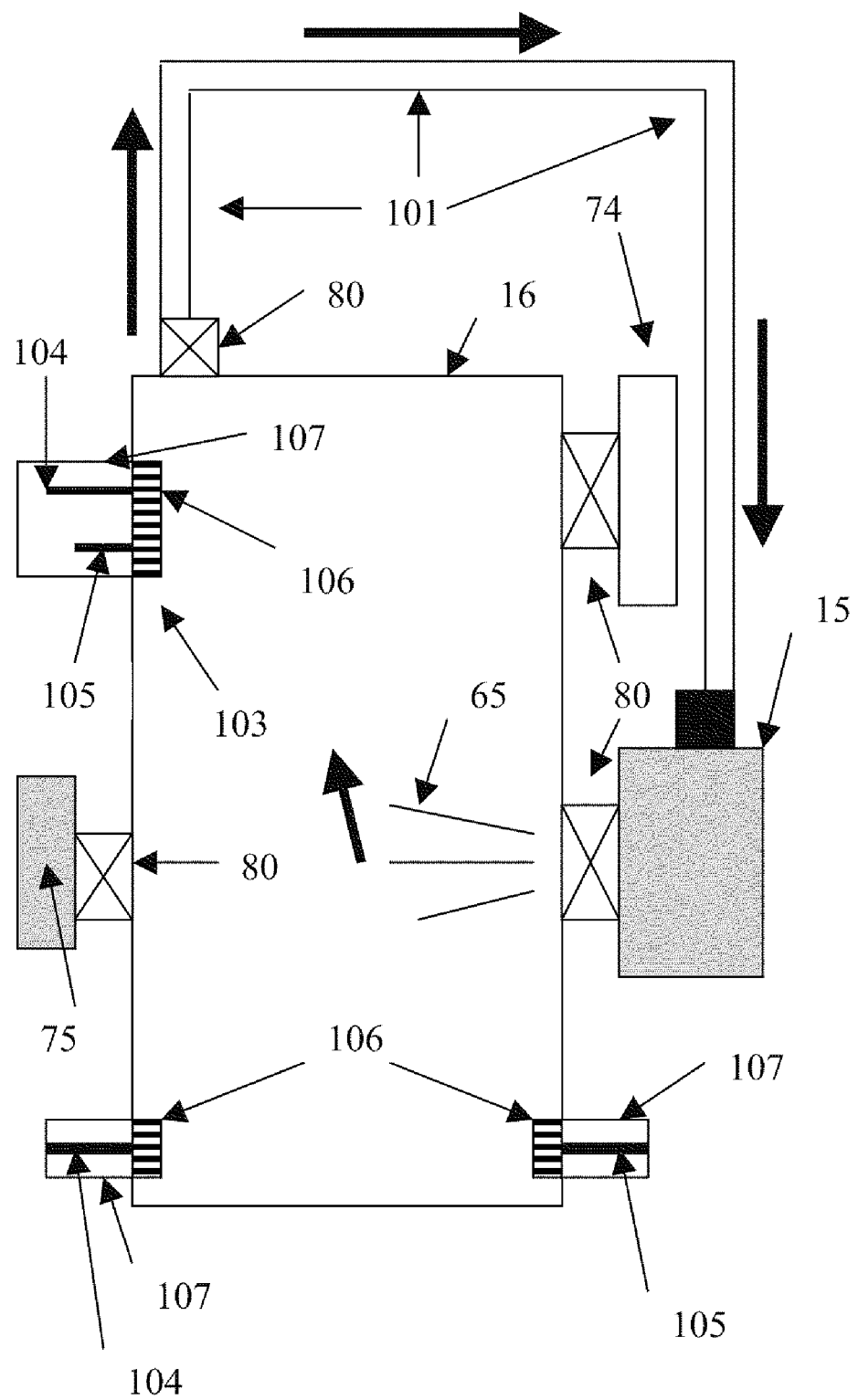
FIG. 33 is a schematic diagram of one sterilization chamber with a dehumidification apparatus, a filter, and also incorporates a sensor consisting of a light source and a light-sensing component. The sterilization chamber is connected to one pipe that connects the aerosol generator directly to the sterilization chamber, forming a closed loop system for air/gas flow.

With reference to FIG. 33, according to another embodiment, and without limitation, one or more sensors (103), or the means for indirect or direct communication with one or more sensor(s) (103) or any programmable logic circuit(s) or controller(s) which are connected to one or more sensor(s) (103), can be utilized to determine if an effective or sufficient amount of aerosol (65) has been delivered into the sterilization chamber(s) (16). This embodiment was initially taught in U.S. Pat. No. 7,871,016 and U.S. patent application Ser. No. 12/816,986, both entitled "Method and Apparatus For An Improved Aerosol Generator and Associated Uses and Equipment," which are expressly incorporated by reference herein in their entirety.

The at least one sensor(s) (103) can be located in any area that is targeted for treatment with the applied agent(s) (20) or aerosol (65). It is preferred, without limitation, that the sensor(s) (103) are located in an effective location within the sterilization chamber(s) (16). The one or more sensor(s) (103) can also be, without limitation, positioned outside of the treated area(s) or sterilization chamber(s) (16) behind any suitable window(s) (106) or in any other suitable location if they are optical sensor(s) (103), and monitor the conditions within these various areas through the window(s) (106). This can allow the sensor(s) (103) to properly function while being protected from the environment within the targeted area(s) or sterilization chamber(s) (16).

In another aspect of this embodiment, each sensor(s) (103) includes at least two parts including, but not limited to, a light source (104) and a light sensor (105), known to those skilled in the art. The light source (104) and light sensor (105) can be directly or indirectly connected, or they can be placed or positioned independent from one another. Without being limited, the distance between the light source (104) and light sensor (105) can also vary depending on the type of sensor (103) that is used. For various sensors (103) known in the art, the light source (104) and light sensor (105) can be, without limitation, separated. It is preferred, without limitation, that if sensor(s) like this are used, they are at least separated by an effective distance. It is preferred, without limitation, that the light source (104) and light sensor (105) components of sensors (103) like this are positioned at least two feet or more apart. Other types of sensor(s) (103) known in the art can also integrate both the light source (104) and the light sensor (105) into the same unit or housing (107). These types of sensor(s) (103) can also be, without limitation, utilized in the present invention. These units typically detect reflected light, and the distance between the light source (104) and light sensor (105) may not, without limitation, be an important variable for effective function since they point in a similar direction.

The emitted light or energy, or light source (104) can have, without limitation, any: (a) intensity, (b) brightness, (c) period, (d) frequency, (e) type of light, and (f) wavelength. The light source (104) can be controlled via any electronic system, programmable logic circuit, or other means known in the art. The light sensor (105) can, without limitation, vary widely in its sensitivity and ability to sense light of any: (a) intensity, (b) brightness, (c) period, (d) frequency, (e) type of light, and (f) wavelength. The means to sense the light (105) can also have various capabilities known in the art, including, without limitation, the ability to have adjustable sensitivity and trigger level(s), and the ability to communicate with any electronic system, programmable logic circuit, or other means known in the art. The light sensor(s) (105) can, without limitation, indicate or communicate with any electronic system, programmable logic circuit, or other means known in the art, if it either receives or ceases to receive a desired or set level of light stimulus, and the communication can be accomplished in various ways known in the art. It is preferred, without limitation that the electronic system, programmable logic circuit, or other means known in the art, is indicated or receives information by any means including, but not limited to, an electrical signal, lack of an electrical signal, or any analog signal, from the light sensor(s) (105) or any directly or indirectly connected hardware. This communication can result in various actions such as, but not limited to, shutting down the device used to generate and/or deploy the aerosol (65), or extending the amount of time that the aerosol generator(s) (15) operates and deploys the applied agent(s) (20) or aerosol (65) into the various areas targeted for treatment. Any amount of extended time can, without limitation, be utilized to deploy the applied agent(s) (20) or aerosol (65). It is preferred, without limitation, that the amount of extended time is at least an efficacious or effective amount of time in addition to any initial deployment time that may have been chosen or established in various ways to deploy the applied agent(s) (20) or aerosol (65).

Without limitation, an effective or sufficient amount of administered aerosol (65) in this embodiment can be indicated in various ways including, but not limited to, (a) causing the disruption, lowering, diminishment, or cessation, of the light that is emitted from the light source(s) (104) before it reaches the light sensor(s) (105), (b) causing an increased level of light as the light emitted from the light source(s) (104) is reflected by the sufficient amount of aerosol (65) back to the light sensor(s) (105), (c) causing a decreased level of the light as the light emitted from the light source(s) (104) is not reflected by a surface in front of the light source(s) (104) back to the light sensor(s) (105). The effective, sufficient amount, or specified quantity, of administered aerosol (65) can vary for intended or unintended reasons or designs, and the trigger or sensitivity levels for the light sensor(s) (105) can, without limitation, be varied, calibrated, or adjusted, for each situational circumstance.

Various other embodiments of the present invention are contemplated as being within the scope of the following claims.

We claim:

1. An apparatus for applying an agent to at least one object, comprising:
   an enclosed chamber for retaining at least one object;
   means for introducing at least one agent into said enclosed chamber;
   an interface being removably secured to the at least one object, a portion of the agent being introduced into internal areas of the at least one object through said interface, the agent material flowing through the internal portions of the at least one object; and
   an object support device including a first support member and a second support member, at least one of said first and second support members moving relative to the other causing the at least one object to transfer from one of said first and second support members to the other and thus exposing a portion of the at least one object previously covered by one of said first and second support members.

2. The apparatus for applying an agent to at least one object of claim 1, further comprising:
   at least one of a dehumidification apparatus and a deodorizing apparatus being connected to said enclosed chamber.

3. The apparatus for applying an agent to at least one object of claim 1, further comprising:
   one of a vacuum device and a positive pressure device for creating a flow of at least one of a gas and the at least one agent through the internal areas of the at least one object, the remainder of the gas and the at least one agent contacting external portions of the at least one object.

4. The apparatus for applying an agent to at least one object of claim 1 wherein:
   said interface includes a coupling and an interface material, one end of coupling being sized to receive one end of said interface material and the other end being connected to a source of the agent, the other end of the interface material being connected to the object.

5. The apparatus for applying an agent to at least one object of claim 1 wherein:
   the agent is in the form of at least one of a gas, a vapor, a plasma and an aerosol.

6. The apparatus for applying an agent to at least one object of claim 1 wherein:
   the agent is at least one of a sanitization, disinfection, detoxification, high level disinfection and sterilization material.

7. The apparatus for applying an agent to at least one object of claim 1, further comprising:
   said means for changing temperature being at least one of a thermoelectric air cooling system, a thermoelectric gas cooling system, a refrigerated air system and a refrigerated gas system.

8. The apparatus for applying an agent to at least one object of claim 1 wherein:
   at least one surface of the at least one object is reduced in temperature below a dew point of an environment surrounding the at least one object.

9. The apparatus for applying an agent to at least one object of claim 1 wherein:
   movement of said first and second support members is repeated at least two times.

10. The apparatus for applying an agent to at least one object of claim 1 wherein:
    the at least one agent and gas are flowed through a plurality of openings formed through said first and second support members at any effective density, concentration or flow rate.

11. The apparatus for applying an agent to at least one object of claim 1, further comprising:
    at least one of a chemical indicator and a biological indicator for at least one of the validation of sanitization, disinfection, high level disinfection, sterilization, and detoxification to measure the level of efficacy reached within the enclosed chamber, said at least one indicator being located behind at least one sealing device, said at least one sealing device being opened for performing the validation.

12. The apparatus for applying an agent to at least one object of claim 1 wherein:
    the at least one object in said enclosed chamber are treated by at least one of drying, exposure to at least one agent, dehumidification and deodorizing.

13. The apparatus for applying an agent to at least one object of claim 1, further comprising:
    a light source for emitting light into said enclosed chamber; and
    a light sensor for detecting the light, said light sensor detecting the amount of light to determine the amount of aerosol in said enclosed chamber.

14. The apparatus for applying an agent to at least one object of claim 1 wherein:
    the at least one object is a package containing at least one second object, the package having at least one side wall fabricated from a porous material with a sufficient dimension, a sufficient pore size, a sufficient pore density and a sufficient porosity to allow the at least one agent to achieve an efficacious result inside of the package.

15. An apparatus for applying an agent to at least one object, comprising:
    an enclosed chamber for retaining at least one object;
    means for introducing at least one agent into said enclosed chamber;
    an interface being removably secured to the at least one object, a portion of the agent being introduced into internal areas of the at least one object through said interface, the agent material flowing through the internal portions of the at least one object; and
    means for doing at least one of dehumidifying an inner portion of said enclosed chamber, deodorizing an inner portion of said enclosed chamber and changing the temperature inside of said enclosed chamber relative to temperature outside of said enclosed chamber; and
    an object support device including a first support member and a second support member, at least one of said first and second support members moving relative to the other causing the at least one object to transfer from one of said first and second support members to the other and thus exposing a portion of the at least one object previously covered by one of said first and second support members.

16. The apparatus for applying an agent to at least one object of claim 15, further comprising:
    said means for dehumidifying being a dehumidification apparatus, said dehumidification apparatus being connected to said enclosed chamber to remove humidity therefrom.

17. The apparatus for applying an agent to at least one object of claim 15, further comprising:
one of a vacuum device and a positive pressure device for creating a flow of at least one of a gas and the at least one agent through the internal areas of the at least one object, the remainder of the gas and the at least one agent contacting external portions of the at least one object.

18. The apparatus for applying an agent to at least one object of claim 15 wherein:
said interface includes a coupling and an interface material, one end of coupling being sized to receive one end of said interface material and the other end being connected to a source of the agent, the other end of the interface material being connected to the object.

19. The apparatus for applying an agent to at least one object of claim 15 wherein:
the agent is in the form of at least one of a gas, a vapor, a plasma and an aerosol.

20. The apparatus for applying an agent to at least one object of claim 15 wherein:
the agent is at least one of a sanitization, disinfection, detoxification, high level disinfection and sterilization material.

21. The apparatus for applying an agent to at least one object of claim 15, further comprising:
at least one of a thermoelectric air cooling system, a thermoelectric gas cooling system, a refrigerated air system and a refrigerated gas system for changing temperature inside of said enclosed chamber relative to temperature outside of said enclosed chamber.

22. The apparatus for applying an agent to at least one object of claim 15 wherein:
at least one surface of the at least one object is reduced in temperature below a dew point of an environment surrounding the at least one object.

23. The apparatus for applying an agent to at least one object of claim 15 wherein:
movement of said first and second support members is repeated at least two times.

24. The apparatus for applying an agent to at least one object of claim 15 wherein:
a plurality of openings or vents are formed through said first and second support members.

25. The apparatus for applying an agent to at least one object of claim 15 wherein:
the at least one agent and gas is flowed through a plurality of openings formed through said first and second support members at any effective density, concentration or flow rate.

26. The apparatus for applying an agent to at least one object of claim 15, further comprising:
at least one of a chemical indicator and a biological indicator for at least one of the validation of sanitization, disinfection, high level disinfection, sterilization, and detoxification to measure the level of efficacy reached within the enclosed chamber, said at least one indicator being located behind at least one sealing device, said at least one sealing device being opened for performing the validation.

27. The apparatus for applying an agent to at least one object of claim 15, further comprising:
a light source for emitting light into said enclosed chamber; and
a light sensor for detecting the light, said light sensor detecting the amount of light to determine the amount of aerosol in said enclosed chamber.

28. The apparatus for applying an agent to at least one object of claim 15 wherein:
the at least one object is a package containing at least one second object, the package having at least one side wall fabricated from a porous material with a sufficient dimension, a sufficient pore size, a sufficient pore density and a sufficient porosity to allow the at least one agent to achieve an efficacious result inside of the package.

29. An apparatus for applying an agent to at least one object, comprising:
an enclosed chamber for retaining at least one object;
means for introducing at least one agent into said enclosed chamber;
an interface being removably secured to the at least one object, a portion of the agent being introduced into internal areas of the at least one object through said interface, the agent material flowing through the internal portions of the at least one object; and
an object support device including a first support member and a second support member, at least one of said first and second support members moving relative to the other causing the at least one object to transfer from one of said first and second support members to the other and thus exposing a portion of the at least one object previously covered by one of said first and second support members, a plurality of openings or vents are formed through said first and second support members.

30. The apparatus for applying an agent to at least one object of claim 29, further comprising:
said means for deodorizing being a deodorizing apparatus, said deodorizing apparatus being connected to said enclosed chamber to remove odor therefrom.

31. The apparatus for applying an agent to at least one object of claim 29, further comprising:
one of a vacuum device and a positive pressure device for creating a flow of at least one of a gas and the at least one agent through the internal areas of the at least one object, the remainder of the gas and the at least one agent contacting external portions of the at least one object.

32. The apparatus for applying an agent to at least one object of claim 29 wherein:
said interface includes a coupling and an interface material, one end of coupling being sized to receive one end of said interface material and the other end being connected to a source of the agent, the other end of the interface material being connected to the object.

33. The apparatus for applying an agent to at least one object of claim 29 wherein:
the agent is at least one of a sanitization, disinfection, detoxification, high level disinfection and sterilization material.

34. The apparatus for applying an agent to at least one object of claim 29, further comprising:
means for changing temperature being at least one of a thermoelectric air cooling system, a thermoelectric gas cooling system, a refrigerated air system and a refrigerated gas system.

35. The apparatus for applying an agent to at least one object of claim 29 wherein:
the at least one object is a package containing at least one second object, the package having at least one side wall fabricated from a porous material with a sufficient dimension, a sufficient pore size, a sufficient pore density and a sufficient porosity to allow the at least one agent to achieve an efficacious result inside of the package.

* * * * *